US010973780B2

(12) United States Patent
Becker et al.

(10) Patent No.: US 10,973,780 B2
(45) Date of Patent: Apr. 13, 2021

(54) KETAMINE FORMULATION FOR SUBCUTANEOUS INJECTION

(71) Applicant: Bexson Biomedical, Inc., Santa Barbara, CA (US)

(72) Inventors: Jeffrey Becker, Santa Barbara, CA (US); Gregg Peterson, Santa Barbara, CA (US); Jason Wallach, Philadelphia, CA (US)

(73) Assignee: Bexson Biomedical, Inc., Santa Barbara, CA (US)

( * ) Notice: Subject to any disclaimer, the term of this patent is extended or adjusted under 35 U.S.C. 154(b) by 0 days.

(21) Appl. No.: 16/874,485

(22) Filed: May 14, 2020

(65) Prior Publication Data

US 2020/0360308 A1 Nov. 19, 2020

Related U.S. Application Data

(60) Provisional application No. 62/848,420, filed on May 15, 2019.

(51) Int. Cl.
*A61K 31/135* (2006.01)
*A61K 47/40* (2006.01)
*A61K 9/00* (2006.01)

(52) U.S. Cl.
CPC .......... *A61K 31/135* (2013.01); *A61K 9/0019* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,352,683 A | 10/1994 | Mayer et al. | |
| 5,403,841 A | 4/1995 | Lang et al. | |
| 6,605,635 B1 | 8/2003 | Bai et al. | |
| 7,034,013 B2 * | 4/2006 | Thompson | A61K 9/0019 514/58 |
| 2003/0055023 A1 * | 3/2003 | Rajewski | B82Y 5/00 514/58 |
| 2013/0296437 A1 | 11/2013 | Young et al. | |
| 2015/0259110 A1 | 9/2015 | Blackburn | |
| 2017/0042878 A1 | 2/2017 | Fava et al. | |
| 2017/0049780 A1 | 2/2017 | Wainer et al. | |
| 2017/0181966 A1 | 6/2017 | Charney et al. | |

FOREIGN PATENT DOCUMENTS

| | | |
|---|---|---|
| CN | 1939298 A | 4/2007 |
| WO | WO-2017180589 A1 | 10/2017 |

OTHER PUBLICATIONS

Javid et al. "Evaluation of a Low Dose Ketamine in Post Tonsillectomy Pain Relief: A Randomized Trial Comparing Intravenous and Subcutaneous Ketamine in Pediatrics," Anesth Pain. 2012; 2(2):85-89. DOI: 10.5812/aapm.4399 (Year: 2012).*
Donnelly "Stability of Diluted Ketamine Packaged in Glass Vials," CJHP—vol. 66, No. 3—May-Jun. 2013, (Year: 2013).*
Ketalar Insert 2018, https://www.nps.org.au/medicine-finder/ketalar-solution-for-injection. (Year: 2018).*
Oshima "Continuous subcutaneous injection of ketamine for cancer pain," Can. J. Anaesth. 1990/37:3/pp. 385-392; (Year: 1990).*
Mion et al. "Ketamine Pharmacology: An Update (Pharmacodynamics and Molecular Aspects, Recent Findings)," CNS Neuroscience & Therapeutics 19 (2013) 370-380. (Year: 2013).*
Stella et al. "Cyclodextrins," Toxicologic Pathology, 36:30-42, 2008. (Year: 2008).*
2020 Guidance on Captisol ("How to Solubilize a Drug with Captisol") (Year: 2020).*
MacIntosh et al. "In Vitro and In Vivo Evaluation of a Sulfobutyl Ether β-Cyclodextrin Enabled Etomidate Formulation" Journal of Pharmaceutical Sciences, vol. 93, No. 10, Oct. 2004; (Year: 2004).*
Al-Muhammed, et al. In-vivo studies on dexamethasone sodium phosphate liposomes. J Microencapsul. May-Jun. 1996;13(3):293-306.
Chiang et al.: An Fc domain protein-small molecule conjugate as an enhanced immunomodulator. J. Am. Chem. Soc. 136(9):3370-73 (2014).
Chonn, et al. Recent advances in liposomal drug-delivery systems. Curr Opin Biotechnol. Dec. 1995;6(6):698-708.
Cyclodextrins used as excipients. Eur Med Agency Comm Hum Med Prod. Oct. 2017:16.
Eide et al.: Continuous subcutaneous administration of the N-methyl-D-aspartic acid (NMDA) receptor antagonist ketamine in the treatment of post-herpetic neuralgia. Pain. 61(2):221-228 (1995).
Eyles: Oral Delivery and Fate of Poly (lactic acid) Microsphere-encapsulated Interferon in Rats J. Pharm. Pharmacol. 49:669-674 (1997).
Gilotra et al.: Efficacy of intravenous furosemide versus a novel, pH-neutral furosemide formulation administered subcutaneously in outpatients with worsening heart failure. JACC: Heart Failure, 6(1), pp. 65-70 (2017).
Graven-Nielsen et al.: Quantification of local and referred muscle pain in humans after sequential in injections of hypertonic saline. Pain, 69(1-2), pp. 111-117 (1997).
Heinemann et al.: U-100, pH-Neutral formulation of VIAject®: faster onset of action than insulin lispro in patients with type 1 diabetes. Diabetes, Obesity and Metabolism, 14(3), pp. 222-227 (2012).
Li et al.: Current drug research on PEGylation with small molecular agents. Progress in Polymer Science. 38:421-44 (2013).
Mathaes et al.: Subcutaneous injection volume of biopharmaceuticals—pushing the boundaries. Journal of pharmaceutical sciences, 105(8), pp. 2255-2259 (2016).
Matthew et al.: Ketamine for Treatment-Resistant Unipolar Depression. CNS Drugs. 26(3):189-204 (2012).

(Continued)

*Primary Examiner* — Jeffrey S Lundgren
*Assistant Examiner* — Michael J Schmitt
(74) *Attorney, Agent, or Firm* — Wilson Sonsini Goodrich & Rosati

(57) ABSTRACT

Provided herein are subcutaneous formulations of ketamine that are useful for treating a variety of disease and disorders. The subcutaneous ketamine formulations provided herein reduce injection site irritation and pain.

20 Claims, No Drawings

(56) References Cited

OTHER PUBLICATIONS

Ostro et al.: Use of liposomes as injectable-drug delivery systems; Am J. Hosp. Pharm. 46(8):1576-1587 (1989).
PCT/US2018/061121 International Search Report and Written Opinion dated Jan. 28, 2019.
Peltoniemi et al.: A Review of Clinical Pharmacokinetics and Pharmacodynamics in Anesthesia and Pain Therapy. Clin Pharmacokinet. 55(9):1059-1077 (2016).
PICKAR. Dosage Calculations. 1999.
Puskás et al.: Sulfobutylether-cyclodextrins: structure, degree of substitution and functional performance. In Cyclodextrins: Synthesis, Chemical Applications and Role in Drug Delivery (pp. 293-320). Nova Science Publishers, Hauppauge, NY (2015).
Rao. Recent developments of collagen-based materials for medical applications and drug delivery systems. J Biomater Sci Polym Ed. 1995;7(7):623-45.
Remington: The science and practice of pharmacy. 20th Edition. Gennaro, Eds. Lippincott Williams & Wilkins, 2003.
Rolan et al.: The absolute bioavailability of racemic ketamine from a novel sublingual formulation. Br J Clin Pharmacol. 77(6):1011-1016 (2013).
Wang, W.: Tolerability of hypertonic injectables. International journal of pharmaceutics, 490(1-2), pp. 308-315 (2015).
Webster et al.: Safety and Efficacy of Prolonged Outpatient Ketamine Infusions for Neuropathic Pain: Am J Ther. 13(4):300-305 (2006).
PCT/US2020/032941 International Search Report and Written Opinion dated Sep. 4, 2020.
PCT/US2020/032941 Invitation to Pay Additional Fees dated Jul. 7, 2020.

\* cited by examiner

KETAMINE FORMULATION FOR SUBCUTANEOUS INJECTION

CROSS REFERENCE

This application claims the benefit of U.S. Provisional Application No. 62/848,420 filed May 15, 2019, which application is incorporated herein by reference in its entirety.

BACKGROUND

Ketamine is an NMDA receptor antagonist that has found use in treating pain and depression and numerous other psychiatric and physical disorders. However, some of ketamine's side effects, poor bioavailability, formulation, and pharmacokinetics limit delivery options. These factors associated with off-label ketamine use present a challenge to effective treatment.

BRIEF SUMMARY OF THE INVENTION

Provided herein are formulations for subcutaneous delivery of ketamine. The formulations provided herein have numerous advantages over existing formulations of ketamine. Currently available Ketamine HCl formulations cause local tissue site irritation when injected subcutaneously. Symptoms can include erythema, itching, swelling, pain and can result in a sterile abscess. This is believed to be due to the acidic pH (<4), high osmolality, the presence of ketamine itself, or a combination of these factors. In contrast, the formulations of ketamine provided herein can avoid these undesired side effects through use of a pH closer to neutral, osmolarity closer to physiological levels, lower concentrations of ketamine, or any combination thereof. Thus, the formulations of ketamine for subcutaneous injection provided herein can reduce injection site adverse reactions, making subcutaneous delivery a clinically safe and tolerable option for patients.

In an aspect provided herein is a pharmaceutical composition, comprising:
(i) a compound of structural Formula (I):

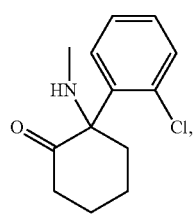

(I)

or an enantiomer, a mixture of enantiomers, or an isotopic variant thereof; or a pharmaceutically acceptable salt, solvate or hydrate thereof; and
(ii) at least one pharmaceutically acceptable excipient, wherein the pharmaceutical composition is in a form for dosing or administration by subcutaneous injection.

In some embodiments, the pharmaceutically acceptable salt comprises a diprotic or triprotic acid.

In some embodiments, the pharmaceutically acceptable salt comprises an organic acid.

In some embodiments, the pharmaceutically acceptable salt comprises an inorganic acid.

In some embodiments, the acid is a substituted or unsubstituted carboxylic acid, a substituted or unsubstituted phenol, a substituted or unsubstituted sulfonic acid, a substituted or unsubstituted alcohol, a substituted or unsubstituted thiol, a substituted or unsubstituted enol, or a carbonic acid.

In some embodiments, the acid is fumaric acid, malic acid, citric acid, tartaric acid, glutaric acid, succinic acid, maleic acid, or malonic acid.

In some embodiments, the acid is a sulfuric, sulfonic, phosphonic, or a phosphoric acid.

In some embodiments, the pharmaceutical composition further comprises a complexing agent.

In some embodiments, the complexing agent is a substituted or unsubstituted cyclodextrin.

In some embodiments, the cyclodextrin is a sulfobutyl-ether-beta-cyclodextrin (SBEBCD) or a hydroxypropyl-beta-cyclodextrin (HPBCD).

In some embodiments, the cyclodextrin is a SBEBCD.

In some embodiments, the molar ratio of SBEBCD to the compound of Formula (I) is from about 1:4 to about 1:8.

In some embodiments, the pharmaceutical composition further comprises a base, a buffer, or a combination thereof.

In some embodiments, the pharmaceutical composition does not further comprises a base, a buffer, or a combination thereof.

In some embodiments, the pharmaceutical composition further comprises an emulsifying agent, a surfactant, a solubilizing agent, a co-solvent or a combination thereof. In some embodiments, the pharmaceutical composition does not further comprise an emulsifying agent, a surfactant, a solubilizing agent, a co-solvent or a combination thereof.

In some embodiments, the co-solvent is ethanol, propylene glycol, tween 20, tween 80, or glycerin.

In some embodiments, the compound of Formula (I) is a pharmaceutically acceptable salt having structural Formula (I-A):

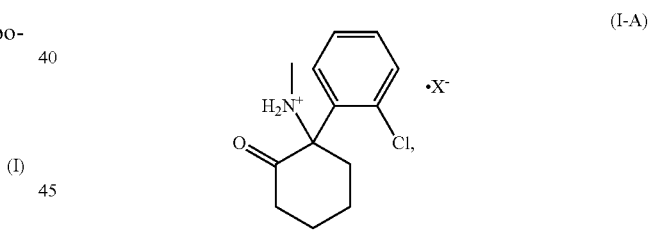

(I-A)

or an enantiomer, a mixture of enantiomers, or an isotopic variant thereof; or solvate or hydrate thereof, wherein:
$X^-$ is a counter ion, and further wherein the compound of Formula (I-A).

In some embodiments, the compound of structural Formula (I-A), or an enantiomer, a mixture of enantiomers, or an isotopic variant thereof; or solvate or hydrate thereof is partially ionized or fully ionized.

In some embodiments, the compound of structural Formula (I-A), or an enantiomer, a mixture of enantiomers, or an isotopic variant thereof; or solvate or hydrate thereof is at least about 75% ionized.

In some embodiments, $X^-$ is fumarate, malate, citrate, tartrate, glutarate, succinate, maleate, an SBEBCD, or malonate.

In some embodiments, the pharmaceutical composition further comprises a complexing agent.

In some embodiments, the complexing agent is a substituted or unsubstituted cyclodextrin.

In some embodiments, the cyclodextrin is a sulfobutyl-ether-beta-cyclodextrin (SBEBCD) or a hydroxypropyl-beta-cyclodextrin (HPBCD).

In some embodiments, the cyclodextrin is a SBEBCD.

In some embodiments, the molar ratio of SBEBCD to the compound of Formula (I-A) is from about 1:4 to about 1:8.

In some embodiments, the SBEBCD is present in an amount of about 50 mg/mL to about 600 mg/mL.

In some embodiments, the pharmaceutical composition further comprises a base, a buffer, or a combination thereof.

In some embodiments, the pharmaceutical composition further comprises an emulsifying agent, a surfactant, a solubilizing agent, an emulsifying agent, a co-solvent, or a combination thereof.

In some embodiments, the pharmaceutical composition is free of excipient emulsifying agents, complexing agents, surfactant agents, or solubilizing agents.

In some embodiments, the pharmaceutical composition has a pH>about 4.

In some embodiments, the pharmaceutical composition has a pH of about 4 to about 7.

In some embodiments, the pharmaceutical composition has a pH of about 4.5 to about 6.5.

In some embodiments, the pharmaceutical composition has an osmolality of from about 300 mOsm/kg to about 850 mOsm/kg.

In some embodiments, the pharmaceutical composition has an osmolality of about <850 mOsm/kg.

In some embodiments, the pharmaceutical composition is isotonic.

In some embodiments, the pharmaceutical composition has an osmolality of about 500 mOsm/kg.

In some embodiments, the compound of Formula (I) or an enantiomer, a mixture of enantiomers, or an isotopic variant thereof; or solvate or hydrate thereof, has a concentration of about 20 mg/mL to about 150 mg/mL.

In some embodiments, the compound of Formula (I), or an enantiomer, a mixture of enantiomers, or an isotopic variant thereof; or solvate or hydrate thereof, has a concentration of about 95 mg/mL to about 105 mg/mL.

In some embodiments, the compound of Formula (I), or an enantiomer, a mixture of enantiomers, or an isotopic variant thereof; or solvate or hydrate thereof, has a concentration of about 95 mg/mL, about 96 mg/mL, about 97 mg/mL, about 98 mg/mL, about 99 mg/mL, about 100 mg/mL, about 101 mg/mL, 102 mg/mL, about 103 mg/mL, about 104 mg/mL, or about 105 mg/mL.

In some embodiments, the pharmaceutical composition further comprises a preservative.

In some embodiments, the preservative is benzethonium chloride.

In some embodiments, the benzethonium chloride is present in an amount of about 0.1 mg/mL to about 0.5 mg/mL.

In some embodiments, provided herein, is a method of treating pain, comprising administering a therapeutically effective amount of any of the pharmaceutical compositions provided herein. In some embodiments, the pain is acute or chronic pain.

In an aspect, provided herein is a method of treating pain, comprising administering to a subject in need thereof a therapeutically effective amount of a compound of structural Formula (I):

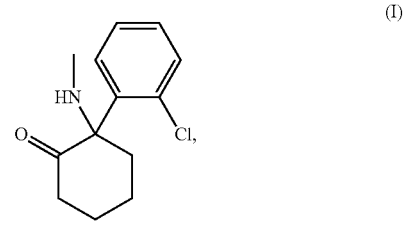 [SMILES: CNC1(c2ccccc2Cl)CCCCC1=O]

or an enantiomer, a mixture of enantiomers, or an isotopic variant thereof; or a pharmaceutically acceptable salt, solvate or hydrate thereof, wherein the compound of Formula (I) is administered by subcutaneous injection.

In some embodiments, the pain is acute pain or chronic pain.

In an aspect, provided herein is a method of treating a psychiatric disorder, a cognitive disorder, or a neurological disorder, comprising administering to a subject in need thereof a therapeutically effective amount of a compound of structural Formula (I):

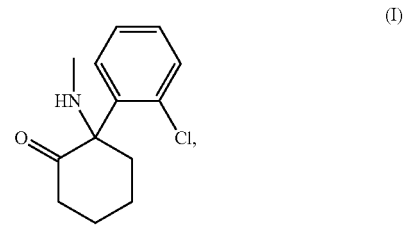 [SMILES: CNC1(c2ccccc2Cl)CCCCC1=O]

or an enantiomer, a mixture of enantiomers, or an isotopic variant thereof; or a pharmaceutically acceptable salt, solvate or hydrate thereof, wherein the compound of Formula (I) is administered by subcutaneous injection.

In some embodiments, the psychiatric disorder is major depressive disorder, treatment resistant major depressive disorder, suicidality, suicidal ideation, dysthymia or persistent depressive disorder, bipolar depressive disorder type I, bipolar depressive disorder type II, chronic pain, eating disorder NOS, pain disorder NOS, panic disorder, post-traumatic stress disorder, obsessive-compulsive disorder, complex regional pain syndrome, reflex sympathetic dystrophy, or any combination thereof.

In some embodiments, the cognitive disorder, or a neurological disorder is Huntington's disease, Parkinson's disease, frontotemporal dementia, dementia, Alzheimer's disease, amyotrophic lateral sclerosis, spinal cord trauma, stroke, diffuse traumatic brain injury, HIV-associated dementia, epilepsy, Rett syndrome, dyskinesia, unspecified dystonia, or pseudobulbar affect.

In some embodiments, the compound of Formula (I) or an enantiomer, a mixture of enantiomers, or an isotopic variant thereof; or a pharmaceutically acceptable salt, solvate or hydrate thereof, is administered by bolus injection or infusion pump. In some embodiments, the compound of Formula (I), or an enantiomer, a mixture of enantiomers, or an isotopic variant thereof; or solvate or hydrate thereof, is administered as a low volume infusion.

In one aspect, provided herein, is a method of preparing a pharmaceutical composition, comprising: mixing a free acid form of a complexing agent comprising at least one acidic functional group and a compound of structural Formula (I):

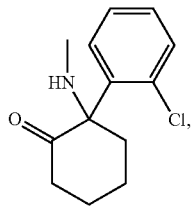

(I)

or an enantiomer, a mixture of enantiomers, or an isotopic variant thereof; or a solvate or hydrate thereof; wherein the compound of structural Formula (I) is in its freebase form. In some embodiments, the mixing occurs in an aqueous medium. In some embodiments, the pharmaceutical composition is in a form for dosing or administration by subcutaneous injection.

In some embodiments, the complexing agent comprising at least one acidic functional group is a cyclodextrin. In some embodiments, the complexing agent comprising at least one acidic functional group is a cyclodextrin substituted with one or more acidic functional groups selected from a carboxylic acid, a sulfonic acid, a sulfinic acid, a phosphonic, and a phosphinic acid, or any combination thereof.

In some embodiments, the complexing agent is a cyclodextrin of Formula (II):

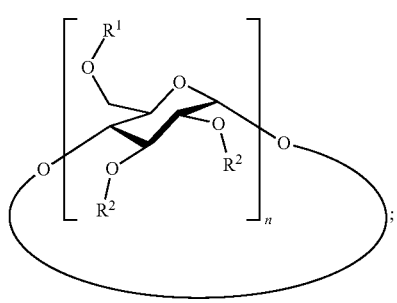

(II)

wherein: each $R^1$ is independently H, optionally substituted alkyl; each $R^2$ is independently H, optionally substituted alkyl; and n is 6, 7, or 8; or a stereoisomer, a mixture of stereoisomers, or an isotopic variant thereof; or a pharmaceutically acceptable salt, solvate or hydrate thereof.

In some embodiments, complexing agent is a sulfobutyl-ether-beta-cyclodextrin (SBEBCD).

In some embodiments, the molar ratio of acidic functional groups of the complexing agent to the compound of Formula (I) is about 1:1. In some embodiments, the molar ratio of the complexing agent to the compound of Formula (I) is from about 1:4 to about 1:10.

In some embodiments, the method further comprises adjusting the pH of the pharmaceutical composition. In some embodiments, the pH of the pharmaceutical composition is from about 4 to about 7. In some embodiments, the method further comprises adding a preservative to the composition. In some embodiments, the method further comprises adding a base, a buffer, an emulsifying agent, a surfactant, a solubilizing agent, an emulsifying agent, a co-solvent, or any combination thereof.

In some embodiments, the pharmaceutical composition has an osmolality of about <500 mOsm/kg. In some embodiments, the pharmaceutical composition has a concentration of the compound of Formula (I) of at least about 20 mg/mL.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Provided herein are, for example, compositions comprising ketamine with reduced irritant effect to subcutaneous tissues and/or dermal tissues. In certain aspects, the compositions comprising ketamine are formulated for subcutaneous administration. Also provided herein are, for example, methods of treating or preventing pain, psychiatric disorders, cognitive disorders, neurological disorders, and other various disorders.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The terms "disease," "disorder," or "condition" refer to a state of being or health status of a patient or subject capable of being treated with the compounds or methods provided herein. The disease may be a mental or psychiatric disorder. The disease may be a mood disorder. The disease may be an inflammatory disease. The disease may be a neurological condition or disorder. In some further instances, "mental or psychiatric disorder" refers to human mental or psychiatric disorders including major depressive disorder, treatment resistant major depressive disorder, Suicidality, Suicidal Ideation, bipolar I disorder, bipolar II disorder, post-traumatic stress disorder (PTSD), a substance-related disorder (e.g., *cannabis* dependence or withdrawal, barbiturate dependence or withdrawal, benzodiazepine dependence or withdrawal, amphetamine dependence or withdrawal, opioid dependence or withdrawal, alcohol dependence or withdrawal, cocaine dependence or withdrawal). In some further instances, "neurological disease or disorder" refers to human neurological diseases or disorders including chronic fatigue syndrome, chronic fatigue and immunodeficiency syndrome, neuropathy, fibromyalgia, fibromyalgia syndrome, myalgic encephalomyelitis, migraine, traumatic brain injury (TBI), stroke, dementia, amyotrophic lateral sclerosis, spinal cord injury, shingles, herpes zoster, radiculopathy, polyneuropathy, dyskinesia, dystonia, tinnitus, postherpetic neuralgia, complex regional pain syndrome, central pain syndrome, chronic pain, acute pain, phantom limb syndrome with pain, phantom limb syndrome without pain, and myelitis.

The expression "effective amount," when used to describe therapy to an individual suffering from a disorder, refers to the amount of a compound described herein that is effective to inhibit or otherwise act on NMDA receptors in the individual's tissues wherein NMDA in the disorder is active, wherein such inhibition or other action occurs to an extent sufficient to produce a beneficial therapeutic effect.

"Substantially" as the term is used herein means completely or almost completely. For example, a composition that is "substantially free" of a component either has none of the component or contains such a trace amount that any relevant functional property of the composition is unaffected by the presence of the trace amount. For example, a compound that is "substantially pure" has only negligible traces of impurities present.

All chiral, diastereomeric, and/or racemic forms of a structure are intended, unless a particular stereochemistry or isomeric form is specifically indicated. Compounds described herein can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the present disclosure.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, e.g., protium ($^1H$), deuterium ($^2H$), or tritium ($^3H$) in any combination. Similarly, any carbon atom or set thereof in a molecule can be any of the isotopic form of carbons, such as $^{11}C$, $^{12}C$, $^{13}C$, or $^{14}C$, or any nitrogen atom or set thereof in a molecule can be any of the isotopic forms of nitrogen, such as $^{13}N$, $^{14}N$, or $^{15}N$. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}S$, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}C$ and $^3H$ can be prepared using neutrons generated in a nuclear reactor. Following nuclear transformation, $^{14}C$ and $^3H$ are incorporated into precursor molecules, followed by further elaboration as needed.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, e.g., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, e.g., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Further examples of prodrugs include boronate esters which can be hydrolyzed under physiological conditions to afford the corresponding boronic acid. Conventional procedures for the selection and preparation of suitable prodrug derivatives are described, for example, in "Design of Prodrugs", ed. H. Bundgaard, Elsevier, 1985.

In various embodiments, a compound as shown in any of the Examples, or among the exemplary compounds, is provided.

Provisos may apply to any of the disclosed categories or embodiments wherein any one or more of the other above disclosed embodiments or species may be excluded from such categories or embodiments.

Isomerism in Compounds Described Herein

Optical Isomerism

It will be understood that when compounds of the present disclosure contain one or more chiral centers, the compounds may exist in, and may be isolated as pure enantiomeric or diastereomeric forms or as racemic mixtures. The present disclosure therefore includes any possible enantiomers, diastereomers, racemates or mixtures thereof of the compounds described herein.

The isomers resulting from the presence of a chiral center comprise a pair of non-superimposable isomers that are called "enantiomers." Single enantiomers of a pure compound are optically active, e.g., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking is A>B>C>D. The lowest ranking atom, D is oriented away from the viewer.

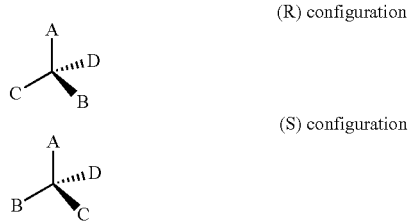

(R) configuration (S) configuration

The present disclosure is meant to encompass diastereomers as well as their racemic and resolved, diastereomerically and enantiomerically pure forms and salts thereof. Diastereomeric pairs may be resolved by known separation techniques including normal and reverse phase chromatography, and crystallisation.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound described herein, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; e.g., the R and S configurations for each asymmetric center. Therefore, single stereochemical isomers as well as enantiomeric and diastereomeric mixtures of the present compounds are within the scope of the disclosure.

"Alkyl" refers to a straight or branched hydrocarbon chain radical consisting solely of carbon and hydrogen atoms, which may optionally be unsaturated with one or more double or triple bonds, and preferably having from one to fifteen carbon atoms (i.e., $C_1$-$C_{15}$ alkyl). In certain embodiments, an alkyl comprises one to six carbon atoms (i.e., $C_1$-$C_6$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless otherwise specified, the term "alkyl" and its equivalents encompass linear, branched, and/or cyclic alkyl groups. In some instances, an "alkyl" comprises both cyclic and acyclic (linear and/or branched) alkyl components.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents may be one or more and the same or different for appropriate organic compounds.

Substituents may include any substituent, for example, a halogen, a hydroxyl, a carbonyl (such as an oxo (═O), a carboxyl, an alkoxycarbonyl, a formyl, or an acyl), a thiocarbonyl (such as a thioxo (═S), a thioester, a thioacetate, or a thioformate), an alkoxyl, a phosphoryl, a phosphate, a phosphonate, a phosphinate, an amino, an amido, an amidine, an imine, an oximo, a hydrazino, a cyano, a nitro, an azido, a sulfhydryl, an alkyl, an alkylthio, a sulfate, a sulfonate, a sulfamoyl, a sulfonamido, a sulfonyl, an aralkyl, a carbocycle, a heterocycle, a cycloalkyl, a heterocycloalkyl, an aromatic and heteroaromatic moiety.

As used herein, an "acidic functional group" or similar term (e.g. "acidic functionality") refers to a chemical moiety which contains at least one dissociable proton (or isotopic variant thereof). In certain embodiments, the dissociable proton dissociates from the chemical moiety at a pH common in aqueous systems (e.g. pHs from about 1 to about 14). In certain preferred embodiments, the dissociable proton dissociates from the chemical moiety in an aqueous system at a pH of less than 7 (e.g. having a pKa value of less than 7, such as a pKa of less than 6, less than 5, less than 4, less than 3, less than 2, or less than 1). As is understood by those in the art, whether an acidic functional group contains the dissociable proton will depend on the conditions of the system in which the chemical moiety is present (e.g., the pH of an aqueous system containing molecule with the acidic functional group or the presence of any base molecule). As such, the term "acidic functional group" (or reference to a specific acidic functional group such as a carboxylic acid or a sulfonic acid) as used herein is intended to cover the protonated version of the moiety, the deprotonated version of the moiety, and any salt of the moiety, unless otherwise specified.

Unless otherwise stated, structures depicted herein are also meant to include compounds which differ only in the presence of one or more isotopically enriched atoms (e.g., isotopic variant(s)). For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

A "salt," as is well known in the art, includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. The terms "pharmaceutically acceptable salts" and/or or "pharmacologically acceptable salts" are meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In certain embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of a compound to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, complexing agents (e.g. cyclodextrins), binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilisers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "treating" or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In certain embodiments, treating is preventing. In certain embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (e.g., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In certain embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of an inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described herein. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means subcutaneous (i.e., "SC," "subQ," or "SQ") administration, oral administration, administration as a suppository, topical contact or administration, intravenous, parenteral, intraperitoneal, intramuscular, intraosseous, intralesional, intrathecal, intracranial, intranasal, epidural, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). The compound of the disclosure can be administered alone or can be coadministered to the patient. Coadministration is meant to include simultaneous or sequential administration of the compound individually or in combination (more than one compound or agent). Thus, the preparations can also be combined, when desired, with other active substances (e.g., to reduce metabolic degradation). The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, e.g., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present disclosure can also be delivered as nanoparticles.

By "co-administer" it is meant that a composition described herein is administered at the same time, just prior to, or just after the administration of one or more additional therapies. The compounds of the disclosure can be administered alone or can be coadministered to the patient. Coadministration is meant to include simultaneous or sequential administration of the compounds individually or in combination (more than one compound). The compositions of the present disclosure can be delivered transdermally, by a topical route, or formulated as applicator sticks, solutions, suspensions, emulsions, gels, creams, ointments, pastes, jellies, paints, powders, and aerosols.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating a mental or psychiatric disorder, a mood disorder, a neurological condition or disorder, a metabolic disorder (e.g., type 2 diabetes mellitus and/or complications thereof), endometriosis, glaucoma, pain, or an inflammatory disorder.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, e.g., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for infections (e.g. bacterial infections), inflammation, and/or vasodilation.

The compounds described herein can be administered to treat a metabolic disease or disorder (e.g., type 2 diabetes mellitus and/or complications thereof), a mental or psychiatric disorder, a mood disorder, a neurological condition or disorder, endometriosis, glaucoma, pain, or an inflammatory disorder. In this regard, the compounds disclosed herein may be administered either alone to treat such diseases or disorders or may be co-administered with another therapeutic agent to treat such diseases or disorders.

The compounds disclosed herein may be co-administered with other active agents including but not limited to antidepressants, antipsychotics, anti-inflammatories, anxiolytics, and/or analgesics.

The inhibitors (e.g., NMDA inhibitors, etc.) disclosed herein may be administered once daily until study reached endpoint. The inhibitors disclosed herein may be administered at least three times but in some studies four or more times depending on the length of the study and/or the design of the study.

The term "bioavailability (F)," as used herein, refers to the fraction of a dose of drug (e.g., epinephrine) that is absorbed from its site of administration and reaches, in an unchanged form, the systemic circulation. The term "absolute bioavailability" is used when the fraction of absorbed drug is related to its I.V. bioavailability. It may be calculated using the following formula:

$$F = \frac{AUC_{extravascular}}{AUC_{intravenous}} \times \frac{Dose_{intravenous}}{Dose_{extravascular}}$$

The term relative bioavailability ($F_{rel}$) is used to compare two different extravascular routes of drug administration and it may be calculated using the following formula:

$$F_{rel} = \frac{AUC_{extravascular\,1}}{AUC_{extravascular\,2}} \times \frac{Dose_{extravascular\,2}}{Dose_{extravascular\,1}}$$

The term "clearance (CL)," as used herein, refers to the rate at which a drug is eliminated divided by its plasma concentration, giving a volume of plasma from which drug is completely removed per unit of time. CL is equal to the elimination rate constant ($\lambda$) multiplied by the volume of distribution ($V_d$), wherein "$V_d$" is the fluid volume that would be required to contain the amount of drug present in the body at the same concentration as in the plasma. The term "apparent clearance (CL/F)," as used herein, refers to clearance that does not take into account the bioavailability of the drug. It is the ratio of the dose over the AUC.

The term "ketamine," as used herein, refers to a compound of the following structure:

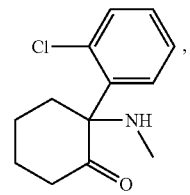 [SMILES: CNC1(c2ccccc2Cl)CCCCC1=O]

or a stereoisomer, pharmaceutically acceptable salt, hydrate, or solvate thereof. The CAS registry number for ketamine is 6740-88-1. Other names for ketamine include, but are not limited to 2-(2-chlorophenyl)-2-(methylamino)cyclohexanone.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

Generally, dosage levels of ketamine in the compositions can range from about 5 µg/kg to about 10 mg/kg, from about 0.5 mg/kg to about 5 mg/kg, from about 1 mg/kg to about 3 mg/kg, or a fixed dose from about 10-100 mg, or 20-75 mg, or 3-60 mg, or 10-250 mg, or 10-400 mg, or an amount greater than 400 mg.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., MAP kinase pathway).

As defined herein, the terms "activation," "activate," "activating," and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc., refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like.

The term "osmolality" as described herein is defined as the number of osmoles (Osm) of solute per kilogram of solvent (osmol/kg or Osm/kg).

The term "osmolarity" as described herein is defined is defined as the number of osmoles of solute per liter (L) of solution (osmol/L or Osm/L).

Osmolarity may be calculated from osmolality as follows: osmolarity=osmolality×$(\rho_{sol}-c_a)$; where $\rho_{sol}$ is the density of the solution in g/mL and $c_a$ is the (anhydrous) solute concentration in g/mL. Unless expressly stated otherwise, osmolarity is calculated using osmolality according to the preceding formula. Alternatively, osmolarity may be calculated experimentally.

II. Compositions

Provided herein are pharmaceutical formulations of ketamine suitable for dosing or administration by subcutaneous injection. Subcutaneously deliverable ketamine has the advantage over other forms of ketamine (e.g. IV or IM delivery) in that it can be used outside of a hospital or clinical setting, such as at home by the subject. Other formulations of ketamine suitable for at home use, such as oral or nasal delivery formulations, tend to require higher doses to achieve comparable clinical effects, which carries risks, including bladder dysfunction due to the higher dosing and dissociative effects. Additionally, oral or sublingual administration is often unreliable due to the presence of food or chyme in the stomach or proximal small intestines and substantial first pass metabolism. Intranasal administration can cause allergic or irritation rhinitis, epistaxis (nosebleeds), or bacterial or viral sinusitis.

In some embodiments, the pharmaceutical formulation provided herein are able to combine a high concentration of ketamine (e.g. >20 mg/mL) with additional characteristics of the formulation making it ideally suited to subcutaneous injection. These additional characteristics may include osmolality near physiological levels and pH near physiological levels while maintaining stability of the formulation and solubility of ketamine. In some embodiments, these desired properties are achieved through use of a complexing agent, particularly cyclodextrins, which act enhance the solubility of ketamine at elevated pHs (e.g. pHs as high as about 5.5). In some embodiments, these attributes are further enhanced through the use modified cyclodextrins, particularly cyclodextrins modified by additional polar groups (e.g. hydroxypropyl-beta-cyclodextrin (HPBCD)) or by sulfonate salt (e.g. sodium salt) functional groups (e.g. a sulfobutyl-ether-beta-cyclodextrin (SBEBCD). In some embodiments, use of a cyclodextrin modified to replace the sodium in the sodium sulfonate salt functional groups to form sulfonic acid functional groups (e.g. SBEBCD) is particularly advantageous, as the sulfonic acidic functional groups can act as the counter-anion to protonate the non-ionized or freebase form of ketamine. In such embodiments, a low osmolality in a high concentration ketamine formulation is achieved because additional salts and counterions can be omitted from the formulation. Thus, high concentrations of ketamine at pH levels compatible with subcutaneous injection can be achieved at osmolalities comparable to physiological levels (~300 mOsm/kg), thus enabling the subcutaneous administration of ketamine without side effects such as pain or injection site irritation.

In an aspect provided herein is a pharmaceutical composition, comprising:
(i) a compound of structural Formula (I):

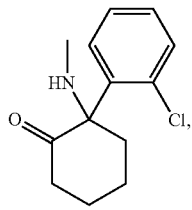

or an enantiomer, a mixture of enantiomers, or an isotopic variant thereof; or a pharmaceutically acceptable salt, solvate or hydrate thereof; and
(ii) at least one pharmaceutically acceptable excipient, wherein the pharmaceutical composition is in a form for dosing or administration by subcutaneous injection.

In an aspect provided herein is a pharmaceutical composition, comprising:
(i) a compound of structural Formula (I):

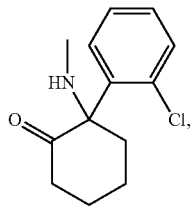

or an enantiomer, a mixture of enantiomers, or an isotopic variant thereof; or a pharmaceutically acceptable salt, solvate or hydrate thereof; and
(ii) at least one pharmaceutically acceptable excipient, wherein the pharmaceutical composition comprises from about 50 mg/mL to about 150 mg/mL of a compound of structural Formula (I), or an enantiomer, a mixture of enantiomers, or an isotopic variant thereof; or a pharmaceutically acceptable salt, solvate or hydrate thereof.

In an aspect provided herein is a pharmaceutical composition, comprising:
(i) a compound of structural Formula (I):

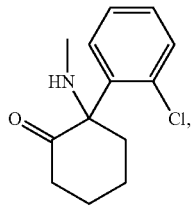

or an enantiomer, a mixture of enantiomers, or an isotopic variant thereof; or a pharmaceutically acceptable salt, solvate or hydrate thereof; and
(ii) at least one pharmaceutically acceptable excipient, wherein the pH pf pharmaceutical composition is from about 4 to about 7.

In some embodiments, the compound of structural Formula (I) (e.g., ketamine) or an enantiomer, a mixture of enantiomers, or an isotopic variant thereof; or a pharmaceutically acceptable salt, solvate or hydrate thereof, is racemic. In some embodiments, the compound of structural Formula (I) (e.g., ketamine) or an enantiomer, a mixture of enantiomers, or an isotopic variant thereof; or a pharmaceutically acceptable salt, solvate or hydrate thereof, is the S-enantiomer. In some embodiments, the compound of structural Formula (I) (e.g., ketamine) or an enantiomer, a mixture of enantiomers, or an isotopic variant thereof; or a pharmaceutically acceptable salt, solvate or hydrate thereof, is the R-enantiomer.

In some embodiments, the pharmaceutically acceptable salt comprises a diprotic or triprotic acid.

In some embodiments, the pharmaceutically acceptable salt comprises an organic acid.

In some embodiments, the pharmaceutically acceptable salt comprises an inorganic acid.

In some embodiments, the acid is a substituted or unsubstituted carboxylic acid, a substituted or unsubstituted phenol, a substituted or unsubstituted sulfonic acid, a substituted or unsubstituted alcohol, a substituted or unsubstituted thiol, a substituted or unsubstituted enol, or a carbonic acid.

In some embodiments, the acid is fumaric acid, malic acid, citric acid, tartaric acid, glutaric acid, succinic acid, maleic acid, or malonic acid.

In some embodiments, the acid is a sulfuric, sulfonic, phosphonic, or a phosphoric acid.

In some embodiments, the pharmaceutically acceptable salt comprises a cyclodextrin substituted with at least one acidic functional group. In some embodiments, the at least one acidic functional group is a carboxylic acid, sulfonic acid, sulfinic acid, phosphonic acid, or phosphinic acid, or any combination thereof. In some embodiments, the cyclodextrin is substituted with at least 1, at least 2, at least 3, at least 4, at least 5, or at least 6 acidic functional groups. In some embodiments, the cyclodextrin is substituted with 3 to 8 acidic functional groups, 3 to 7 acidic functional groups, 4 to 8 acidic functional groups, 4 to 7 acidic functional groups, 5 to 8 acidic functional groups, 6 to 8 acidic functional groups, or 7 to 8 acidic functional groups.

In some embodiments, the pharmaceutical composition further comprises a complexing agent.

In some embodiments, the complexing agent is a substituted or unsubstituted cyclodextrin. In some cases, substituted cyclodextrins provided herein are complex mixtures wherein individual cyclodextrin molecules may comprise different numbers of substituents from other individual cyclodextrin molecules. In such cases, the number of substituents (e.g. the number of acidic functional groups) described as being present on the cyclodextrins provided herein may refer to an average degree of substitution of the mixture. For example, when a cyclodextrin is described as substituted with 3 to 8 acidic functional groups, it is intended that a complex mixture of cyclodextrins having an average degree of substitution from 3 to 8 acidic functional groups is covered. The average degree of substitution need not be an integer value and will often be a decimal value. For example, commercially available SBEBCD has an average degree of substitution of about 6.5.

In some embodiments, the complexing agent is a substituted cyclodextrin. In some embodiments, the substituted cyclodextrin is substituted with one or more acidic functional groups, or a pharmaceutically acceptable salt thereof. In some embodiments, the substituted cyclodextrin is substituted with one or more carboxylic acid, sulfonic acid, sulfinic acid, phosphonic acid, or phosphinic acid. In some embodiments, the cyclodextrin is substituted with at least 1, at least 2, at least 3, at least 4, at least 5, or at least 6 acidic functional groups. In some embodiments, the cyclodextrin is substituted with 3 to 8 acidic functional groups, 3 to 7 acidic functional groups, 4 to 8 acidic functional groups, 4 to 7 acidic functional groups, 5 to 8 acidic functional groups, 6 to 8 acidic functional groups, or 7 to 8 acidic functional groups.

In some embodiments, the molar ratio of the cyclodextrin to the compound of Formula (I) is from about 1:4 to about 1:8. In some embodiments, the molar ratio of the cyclodextrin to the compound of Formula (I) is from about 1:4 to about 1:10. In some embodiments, the molar ratio of the cyclodextrin to the compound of Formula (I) is from about 1:5 to about 1:7. In some embodiments, the molar ratio of the cyclodextrin to the compound of Formula (I) is about 1:4. In some embodiments, the molar ratio of the cyclodextrin to the compound of Formula (I) is about 1:5. In some embodiments, the molar ratio of the cyclodextrin to the compound of Formula (I) is about 1:6. In some embodiments, the molar ratio of the cyclodextrin to the compound of Formula (I) is about 1:7. In some embodiments, the molar ratio of the cyclodextrin to the compound of Formula (I) is about 1:8. In some embodiments, the molar ratio of the cyclodextrin to the compound of Formula (I) is about 1:9. In some embodiments, the molar ratio of the cyclodextrin to the compound of Formula (I) is about 1:10

In some embodiments, molar ratio of acidic functional groups of the complexing agent to the compound of Formula (I) is from about 2:1 to about 1:2. In some embodiments, molar ratio of acidic functional groups of the complexing agent to the compound of Formula (I) is from about 1.75:1 to about 1:1.75. In some embodiments, molar ratio of acidic functional groups of the complexing agent to the compound of Formula (I) is from about 1.5:1 to about 1:1.5. In some embodiments, molar ratio of acidic functional groups of the complexing agent to the compound of Formula (I) is from about 1.4:1 to about 1:1.4. In some embodiments, molar ratio of acidic functional groups of the complexing agent to the compound of Formula (I) is from 1.3:1 to about 1:1.3. In some embodiments, molar ratio of acidic functional groups of the complexing agent to the compound of Formula (I) is from about 1.25:1 to about 1:1.25. In some embodiments, molar ratio of acidic functional groups of the complexing agent to the compound of Formula (I) is from about 1.2:1 to about 1:1.2. In some embodiments, molar ratio of acidic functional groups of the complexing agent to the compound of Formula (I) is from about 1.15:1 to about 1:1.15. In some embodiments, molar ratio of acidic functional groups of the complexing agent to the compound of Formula (I) is from about 1.1:1 to about 1:1.1. In some embodiments, molar ratio of acidic functional groups of the complexing agent to the compound of Formula (I) is from about 1.05:1 to about 1:1.05. In some embodiments, molar ratio of acidic functional groups of the complexing agent to the compound of Formula (I) is about 1:1.

In some embodiments, the cyclodextrin is present in an amount of about 50 mg/mL to about 600 mg/mL. In some embodiments, the cyclodextrin is present in an amount of about 50 mg/mL to about 600 mg/mL. In some embodiments, the cyclodextrin is present in an amount of about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 200 mg/mL to about 300 mg/mL, about 200 mg/mL to about 400 mg/mL, about 200 mg/mL to about 500 mg/mL, about 200 mg/mL to about 600 mg/mL, about 300 mg/mL to about 400 mg/mL, about 300 mg/mL to about 500 mg/mL, about 300 mg/mL to about 600 mg/mL, about 400 mg/mL to about 500 mg/mL, about 400 mg/mL to about 600 mg/mL, or about 500 mg/mL to about 600 mg/mL. In some embodiments, the cyclodextrin is present in an amount of about 50 mg/mL, about 100 mg/mL, about 200 mg/mL, about 300 mg/mL, about 400 mg/mL, about 500 mg/mL, or about 600 mg/mL. In some embodiments, the cyclodextrin is present in an amount of at least about 50 mg/mL, about 100 mg/mL, about 200 mg/mL, about 300 mg/mL, about 400 mg/mL, or about 500 mg/mL. In some embodiments, the cyclodextrin is present in an amount of at most about 100 mg/mL, about 200 mg/mL, about 300 mg/mL, about 400 mg/mL, about 500 mg/mL, or about 600 mg/mL.

In some embodiments, the cyclodextrin is a compound of Formula (II):

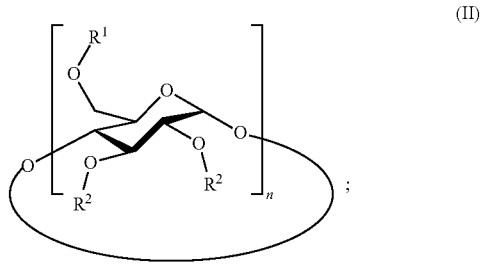

wherein:

each $R^1$ is independently H, optionally substituted alkyl;

each $R^2$ is independently H, optionally substituted alkyl; and n is 6, 7, or 8;

or a stereoisomer, a mixture of stereoisomers, or an isotopic variant thereof; or a pharmaceutically acceptable salt, solvate or hydrate thereof.

In some embodiments, each $R^1$ is independently H or alkyl optionally substituted with a polar functional group. In some embodiments, the polar functional group is an amido functional group, an acidic functional group, an ester functional group, a hydroxyl functional group, an alkoxy functional group, or a poly(alkylene oxide) functional group. In some embodiments, each $R^1$ is independently H or alkyl optionally substituted with an acidic functional group or a hydroxyl functional group.

In some embodiments, each $R^1$ is independently H or alkyl optionally substituted with an acidic functional group. In some embodiments, each $R^1$ is independently H or alkyl substituted with an acidic functional group. In some embodiments, each $R^1$ is independently H or $C_1$-$C_6$ alkyl substituted with an acidic functional group. In some embodiments, each $R^1$ is independently H or $C_1$-$C_6$ alkyl substituted with an acidic functional group selected from a carboxylic acid, a sulfonic acid, a sulfinic acid, a phosphonic acid, or a phosphinic acid. In some embodiments, each $R^1$ is independently H,

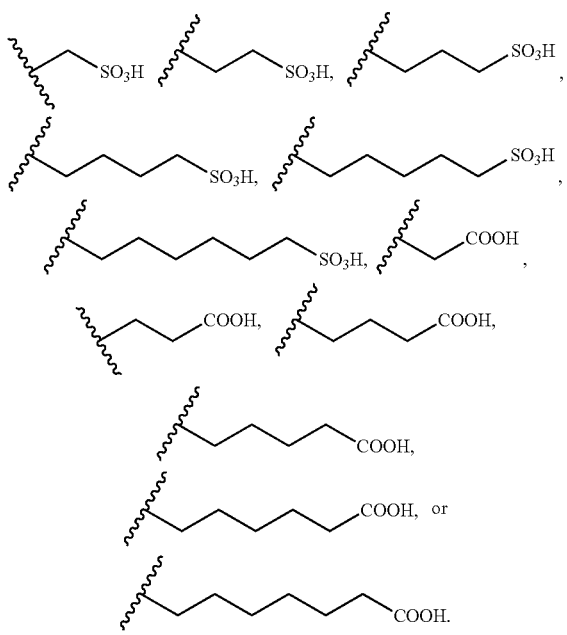

In some embodiments, each $R^1$ is independently H,

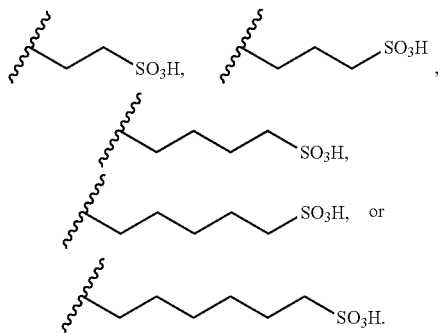

In some embodiments wherein $R^1$ comprises an acidic functional group, each $R^2$ is H or acetyl. In some embodiments wherein $R^1$ comprises an acidic functional group, each $R^2$ is H.

In some embodiments, each $R^1$ is independently H or alkyl optionally substituted with a hydroxyl functional group. In some embodiments, each $R^1$ is independently H or alkyl substituted with a hydroxyl functional group. In some embodiments, each $R^1$ is independently H or $C_1$-$C_6$ alkyl substituted with a hydroxyl functional group. In some embodiments, each $R^1$ is independently H or hydroxypropyl, hydroxybutyl, hydroxypentyl, or hydroxyhexyl. In some embodiments, each $R^1$ and $R^2$ is independently H or hydroxypropyl, hydroxybutyl, hydroxypentyl, or hydroxyhexyl.

In some embodiments, each $R^2$ is independently H or alkyl optionally substituted with a polar functional group. In some embodiments, each $R^2$ is independently H or alkyl optionally substituted with a hydroxyl functional group. In some embodiments, each $R^2$ is independently H or alkyl substituted with a hydroxyl functional group. In some embodiments, each $R^2$ is independently H or $C_1$-$C_6$ alkyl substituted with a hydroxyl functional group. In some embodiments, each $R^2$ is independently H or hydroxypropyl, hydroxybutyl, hydroxypentyl, or hydroxyhexyl. In some embodiments, each $R^2$ is H. In some embodiments, each $R^2$ is H or acetyl.

In some embodiments, n is 6 or 7. In some embodiments, n is 7 or 8. In some embodiments, n is 6. In some embodiments, n is 7. In some embodiments, n is 8.

In some embodiments, the cyclodextrin is a sulfobutyl-ether-beta-cyclodextrin (SBEBCD) or a hydroxypropyl-beta-cyclodextrin (HPBCD).

In some embodiments, the cyclodextrin is a SBEBCD. In some embodiments, the SBEBCD is the free acid form of SBEBCD.

In some embodiments, the molar ratio of SBEBCD to the compound of Formula (I) is from about 1:4 to about 1:8. In some embodiments, the molar ratio of SBEBCD to the compound of Formula (I) is from about 1:4 to about 1:10. In some embodiments, the molar ratio of SBEBCD to the compound of Formula (I) is from about 1:5 to about 1:7. In some embodiments, the molar ratio of SBEBCD to the compound of Formula (I) is about 1:4. In some embodiments, the molar ratio of SBEBCD to the compound of Formula (I) is about 1:5. In some embodiments, the molar ratio of SBEBCD to the compound of Formula (I) is about 1:6. In some embodiments, the molar ratio of SBEBCD to the compound of Formula (I) is about 1:7. In some embodiments, the molar ratio of SBEBCD to the compound of Formula (I) is about 1:8. In some embodiments, the molar ratio of SBEBCD to the compound of Formula (I) is about 1:9. In some embodiments, the molar ratio of SBEBCD to the compound of Formula (I) is about 1:10. In some embodiments, the molar ratio of SBEBCD to the compound of Formula (I) is about 1:2 to about 1:10. In some embodiments, the molar ratio of SBEBCD to the compound of Formula (I) is about 1:2 to about 1:3, about 1:2 to about 1:4, about 1:2 to about 1:5, about 1:2 to about 1:6, about 1:2 to about 1:7, about 1:2 to about 1:8, about 1:2 to about 1:9, about 1:2 to about 1:10, about 1:3 to about 1:4, about 1:3 to about 1:5, about 1:3 to about 1:6, about 1:3 to about 1:7, about 1:3 to about 1:8, about 1:3 to about 1:9, about 1:3 to about 1:10, about 1:4 to about 1:5, about 1:4 to about 1:6, about 1:4 to about 1:7, about 1:4 to about 1:8, about 1:4 to about 1:9, about 1:4 to about 1:10, about 1:5 to about 1:6, about 1:5 to about 1:7, about 1:5 to about 1:8, about 1:5 to about 1:9, about 1:5 to about 1:10, about 1:6 to about 1:7, about 1:6 to about 1:8, about 1:6 to about 1:9, about 1:6 to about 1:10, about 1:7 to about 1:8, about 1:7 to about 1:9, about 1:7 to about 1:10, about 1:8 to about 1:9, about 1:8 to about 1:10, or about 1:9 to about 1:10. In some embodiments, the molar ratio of SBEBCD to the compound of Formula (I) is about 1:2, about 1:3, about 1:4, about 1:5, about 1:6, about 1:7, about 1:8, about 1:9, or about 1:10. In some embodiments, the molar ratio of SBEBCD to the compound of Formula (I) is at least about 1:2, about 1:3, about 1:4, about 1:5, about 1:6, about 1:7, about 1:8, or about 1:9. In some embodiments, the molar ratio of SBEBCD to the compound of Formula (I) is at most about 1:3, about 1:4, about 1:5, about 1:6, about 1:7, about 1:8, about 1:9, or about 1:10.

In some embodiments, the pharmaceutical composition further comprises a base, a buffer, or a combination thereof.

In some embodiments, the pharmaceutical composition does not comprise a base, a buffer, or a combination thereof.

In some embodiments, the co-solvent is ethanol, propylene glycol, tween 20, tween 80, glycerin, or a combination thereof.

In some embodiments, the compound of Formula (I) is a pharmaceutically acceptable salt having structural Formula (I-A):

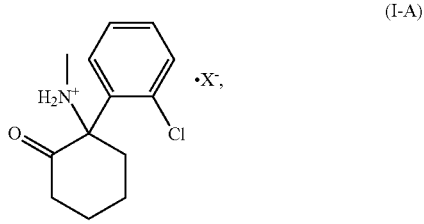 [SMILES: C[NH2+]C1(c2ccccc2Cl)CCCCC1=O]

or an enantiomer, a mixture of enantiomers, or an isotopic variant thereof; or solvate or hydrate thereof, wherein: X⁻ is a counter ion, and further wherein the compound of Formula (I-A).

In some embodiments, the compound of structural Formula (I-A), or an enantiomer, a mixture of enantiomers, or an isotopic variant thereof; or solvate or hydrate thereof is partially ionized or fully ionized.

In some embodiments, the compound of structural Formula (I-A), or an enantiomer, a mixture of enantiomers, or an isotopic variant thereof; or solvate or hydrate thereof is at least about 75% ionized. In some embodiments, the compound of structural Formula (I-A), or an enantiomer, a mixture of enantiomers, or an isotopic variant thereof; or solvate or hydrate thereof is at least about 80% ionized. In some embodiments, the compound of structural Formula (I-A), or an enantiomer, a mixture of enantiomers, or an isotopic variant thereof; or solvate or hydrate thereof is at least about 85% ionized. In some embodiments, the compound of structural Formula (I-A), or an enantiomer, a mixture of enantiomers, or an isotopic variant thereof; or solvate or hydrate thereof is at least about 90% ionized. In some embodiments, the compound of structural Formula (I-A), or an enantiomer, a mixture of enantiomers, or an isotopic variant thereof; or solvate or hydrate thereof is at least about 91% ionized. In some embodiments, the compound of structural Formula (I-A), or an enantiomer, a mixture of enantiomers, or an isotopic variant thereof; or solvate or hydrate thereof is at least about 92% ionized. In some embodiments, the compound of structural Formula (I-A), or an enantiomer, a mixture of enantiomers, or an isotopic variant thereof; or solvate or hydrate thereof is at least about 93% ionized. In some embodiments, the compound of structural Formula (I-A), or an enantiomer, a mixture of enantiomers, or an isotopic variant thereof; or solvate or hydrate thereof is at least about 94% ionized. In some embodiments, the compound of structural Formula (I-A), or an enantiomer, a mixture of enantiomers, or an isotopic variant thereof; or solvate or hydrate thereof is at least about 95% ionized. In some embodiments, the compound of structural Formula (I-A), or an enantiomer, a mixture of enantiomers, or an isotopic variant thereof; or solvate or hydrate thereof is at least about 96% ionized. In some embodiments, the compound of structural Formula (I-A), or an enantiomer, a mixture of enantiomers, or an isotopic variant thereof; or solvate or hydrate thereof is at least about 97% ionized. In some embodiments, the compound of structural Formula (I-A), or an enantiomer, a mixture of enantiomers, or an isotopic variant thereof; or solvate or hydrate thereof is at least about 98% ionized. In some embodiments, the compound of structural Formula (I-A), or an enantiomer, a mixture of enantiomers, or an isotopic variant thereof; or solvate or hydrate thereof is at least about 99% ionized. In some embodiments, the compound of structural Formula (I-A), or an enantiomer, a mixture of enantiomers, or an isotopic variant thereof; or solvate or hydrate thereof is at least about 99.1% ionized. In some embodiments, the compound of structural Formula (I-A), or an enantiomer, a mixture of enantiomers, or an isotopic variant thereof; or solvate or hydrate thereof is at least about 99.2% ionized. In some embodiments, the compound of structural Formula (I-A), or an enantiomer, a mixture of enantiomers, or an isotopic variant thereof; or solvate or hydrate thereof is at least about 99.3% ionized. In some embodiments, the compound of structural Formula (I-A), or an enantiomer, a mixture of enantiomers, or an isotopic variant thereof; or solvate or hydrate thereof is at least about 99.4% ionized. In some embodiments, the compound of structural Formula (I-A), or an enantiomer, a mixture of enantiomers, or an isotopic variant thereof; or solvate or hydrate thereof is at least about 99.5% ionized. In some embodiments, the compound of structural Formula (I-A), or an enantiomer, a mixture of enantiomers, or an isotopic variant thereof; or solvate or hydrate thereof is at least about 99.6% ionized. In some embodiments, the compound of structural Formula (I-A), or an enantiomer, a mixture of enantiomers, or an isotopic variant thereof; or solvate or hydrate thereof is at least about 99.7% ionized. In some embodiments, the compound of structural Formula (I-A), or an enantiomer, a mixture of enantiomers, or an isotopic variant thereof; or solvate or hydrate thereof is at least about 99.8% ionized. In some embodiments, the compound of structural Formula (I-A), or an enantiomer, a mixture of enantiomers, or an isotopic variant thereof; or solvate or hydrate thereof is at least about 99.9% ionized.

In some embodiments, X⁻ is fumarate, malate, citrate, tartrate, glutarate, succinate, maleate, an SBEBCD, or malonate. In some embodiments, X⁻ is a substituted cyclodextrin. In some embodiments, X⁻ is a cyclodextrin substituted with a deprotonated acidic residue. In some embodiments, the deprotonated acidic residue is a carboxylate, a sulfonate, a sulfonate, a phosphonate, or a phosphinate. In some embodiments, the deprotonated acidic residue is a sulfonate. In some embodiments, X⁻ is a compound of Formula (II).

In some embodiments, the pharmaceutical composition further comprises a complexing agent.

In some embodiments, the complexing agent is a substituted or unsubstituted cyclodextrin. In some cases, substituted cyclodextrins provided herein are complex mixtures wherein individual cyclodextrin molecules may comprise different numbers of substituents from other individual cyclodextrin molecules. In such cases, the number of substituents (e.g. the number of acidic functional groups) described as being present on the cyclodextrins provided herein may refer to an average degree of substitution of the mixture. For example, when a cyclodextrin is described as substituted with 3 to 8 acidic functional groups, it is intended that a complex mixture of cyclodextrins having an average degree of substitution from 3 to 8 acidic functional groups is covered.

In some embodiments, the complexing agent is a substituted cyclodextrin. In some embodiments, the substituted cyclodextrin is substituted with one or more acidic functional groups, or a pharmaceutically acceptable salt thereof. In some embodiments, the substituted cyclodextrin is substituted with one or more carboxylic acid, sulfonic acid, sulfonic acid, phosphonic acid, or phosphonic acid. In some embodiments, the cyclodextrin is substituted with at least 1, at least 2, at least 3, at least 4, at least 5, or at least 6 acidic functional groups. In some embodiments, the cyclodextrin is substituted with 3 to 8 acidic functional groups, 3 to 7 acidic functional groups, 4 to 8 acidic functional groups, 4 to 7 acidic functional groups, 5 to 8 acidic functional groups, 6 to 8 acidic functional groups, or 7 to 8 acidic functional groups.

In some embodiments, the molar ratio of the cyclodextrin to the compound of Formula (I-A) is from about 1:4 to about 1:8. In some embodiments, the molar ratio of the cyclodextrin to the compound of Formula (I-A) is from about 1:4 to about 1:10. In some embodiments, the molar ratio of the cyclodextrin to the compound of Formula (I-A) is from about 1:5 to about 1:7. In some embodiments, the molar ratio of the cyclodextrin to the compound of Formula (I-A) is about 1:4. In some embodiments, the molar ratio of the cyclodextrin to the compound of Formula (I-A) is about 1:5. In some embodiments, the molar ratio of the cyclodextrin to the compound of Formula (I-A) is about 1:6. In some embodiments, the molar ratio of the cyclodextrin to the compound of Formula (I-A) is about 1:7. In some embodiments, the molar ratio of the cyclodextrin to the compound of Formula (I-A) to the cyclodextrin is about 1:8. In some embodiments, the molar ratio of the cyclodextrin to the compound of Formula (I-A) to the cyclodextrin is about 1:9. In some embodiments, the molar ratio of the cyclodextrin to the compound of Formula (I-A) to the cyclodextrin is about 1:10.

In some embodiments, molar ratio of acidic functional groups of the complexing agent to the compound of Formula (I-A) is from about 2:1 to about 1:2. In some embodiments, molar ratio of acidic functional groups of the complexing agent to the compound of Formula (I-A) is from about 1.75:1 to about 1:1.75. In some embodiments, molar ratio of acidic functional groups of the complexing agent to the compound of Formula (I-A) is from about 1.5:1 to about 1:1.5. In some embodiments, molar ratio of acidic functional groups of the complexing agent to the compound of Formula (I-A) is from about 1.4:1 to about 1:1.4. In some embodiments, molar ratio of acidic functional groups of the complexing agent to the compound of Formula (I-A) is from about 1.3:1 to about 1:1.3. In some embodiments, molar ratio of acidic functional groups of the complexing agent to the compound of Formula (I-A) is from about 1.25:1 to about 1:1.25. In some embodiments, molar ratio of acidic functional groups of the complexing agent to the compound of Formula (I-A) is from about 1.2:1 to about 1:1.2. In some embodiments, molar ratio of acidic functional groups of the complexing agent to the compound of Formula (I-A) is from about 1.15:1 to about 1:1.15. In some embodiments, molar ratio of acidic functional groups of the complexing agent to the compound of Formula (I-A) is from about 1.1:1 to about 1:1.1. In some embodiments, molar ratio of acidic functional groups of the complexing agent to the compound of Formula (I-A) is from about 1.05:1 to about 1:1.05. In some embodiments, molar ratio of acidic functional groups of the complexing agent to the compound of Formula (I-A) is about 1:1.

In some embodiments, the cyclodextrin is present in an amount of about 50 mg/mL to about 600 mg/mL. In some embodiments, the cyclodextrin is present in an amount of about 50 mg/mL to about 600 mg/mL. In some embodiments, the cyclodextrin is present in an amount of about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 200 mg/mL to about 300 mg/mL, about 200 mg/mL to about 400 mg/mL, about 200 mg/mL to about 500 mg/mL, about 200 mg/mL to about 600 mg/mL, about 300 mg/mL to about 400 mg/mL, about 300 mg/mL to about 500 mg/mL, about 300 mg/mL to about 600 mg/mL, about 400 mg/mL to about 500 mg/mL, about 400 mg/mL to about 600 mg/mL, or about 500 mg/mL to about 600 mg/mL. In some embodiments, the cyclodextrin is present in an amount of about 50 mg/mL, about 100 mg/mL, about 200 mg/mL, about 300 mg/mL, about 400 mg/mL, about 500 mg/mL, or about 600 mg/mL. In some embodiments, the cyclodextrin is present in an amount of at least about 50 mg/mL, about 100 mg/mL, about 200 mg/mL, about 300 mg/mL, about 400 mg/mL, or about 500 mg/mL. In some embodiments, the cyclodextrin is present in an amount of at most about 100 mg/mL, about 200 mg/mL, about 300 mg/mL, about 400 mg/mL, about 500 mg/mL, or about 600 mg/mL.

In some embodiments, the cyclodextrin is a compound of Formula (II).

In some embodiments, the cyclodextrin is a sulfobutyl-ether-beta-cyclodextrin (SBEBCD) or a hydroxypropyl-beta-cyclodextrin (HPBCD).

In some embodiments, the cyclodextrin is a SBEBCD. In some embodiments, the SBEBCD is the free acid form of SBEBCD.

In some embodiments, the molar ratio of SBEBCD to the compound of Formula (I-A) is from about 1:4 to about 1:8. In some embodiments, the molar ratio of SBEBCD to the compound of Formula (I-A) is from about 1:4 to about 1:10. In some embodiments, the molar ratio of SBEBCD to the compound of Formula (I-A) is from about 1:5 to about 1:7. In some embodiments, the molar ratio of SBEBCD to the compound of Formula (I-A) is about 1:4. In some embodiments, the molar ratio of SBEBCD to the compound of Formula (I-A) is about 1:5. In some embodiments, the molar ratio of SBEBCD to the compound of Formula (I-A) is about 1:6. In some embodiments, the molar ratio of SBEBCD to the compound of Formula (I-A) is about 1:7. In some embodiments, the molar ratio of SBEBCD to the compound of Formula (I-A) is about 1:8. In some embodiments, the molar ratio of SBEBCD to the compound of Formula (I-A) is about 1:9. In some embodiments, the molar ratio of SBEBCD to the compound of Formula (I-A) is about 1:10. In some embodiments, the molar ratio of SBEBCD to the compound of Formula (I-A) is about 1:2 to about 1:10. In some embodiments, the molar ratio of SBEBCD to the compound of Formula (I-A) is about 1:2 to about 1:3, about 1:2 to about 1:4, about 1:2 to about 1:5, about 1:2 to about 1:6, about 1:2 to about 1:7, about 1:2 to about 1:8, about 1:2 to about 1:9, about 1:2 to about 1:10, about 1:3 to about 1:4, about 1:3 to about 1:5, about 1:3 to about 1:6, about 1:3 to about 1:7, about 1:3 to about 1:8, about 1:3 to about 1:9, about 1:3 to about 1:10, about 1:4 to about 1:5, about 1:4 to about 1:6, about 1:4 to about 1:7, about 1:4 to about 1:8, about 1:4 to about 1:9, about 1:4 to about 1:10, about 1:5 to about 1:6, about 1:5 to about 1:7, about 1:5 to about 1:8, about 1:5 to about 1:9, about 1:5 to about 1:10, about 1:6 to about 1:7, about 1:6 to about 1:8, about 1:6 to about 1:9, about 1:6 to about 1:10, about 1:7 to about 1:8, about 1:7 to about 1:9, about 1:7 to about 1:10, about 1:8 to about 1:9, about 1:8 to about 1:10, or about 1:9 to about 1:10. In some embodiments, the molar ratio of SBEBCD to the compound of Formula (I-A) is about 1:2, about 1:3, about 1:4, about 1:5, about 1:6, about 1:7, about 1:8, about 1:9, or about 1:10.

In some embodiments, the molar ratio of SBEBCD to the compound of Formula (I-A) is at least about 1:2, about 1:3, about 1:4, about 1:5, about 1:6, about 1:7, about 1:8, or about 1:9. In some embodiments, the molar ratio of SBEBCD to the compound of Formula (I-A) is at most about 1:3, about 1:4, about 1:5, about 1:6, about 1:7, about 1:8, about 1:9, or about 1:10.

In some embodiments, the SBEBCD (or other cyclodextrin compound) is present in an amount of about 50 mg/mL to about 600 mg/mL. In some embodiments, the SBEBCD is present in an amount of about 50 mg/mL to about 600 mg/mL. In some embodiments, the SBEBCD is present in an amount of about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 200 mg/mL to about 300 mg/mL, about 200 mg/mL to about 400 mg/mL, about 200 mg/mL to about 500 mg/mL, about 200 mg/mL to about 600 mg/mL, about 300 mg/mL to about 400 mg/mL, about 300 mg/mL to about 500 mg/mL, about 300 mg/mL to about 600 mg/mL, about 400 mg/mL to about 500 mg/mL, about 400 mg/mL to about 600 mg/mL, or about 500 mg/mL to about 600 mg/mL. In some embodiments, the SBEBCD is present in an amount of about 50 mg/mL, about 100 mg/mL, about 200 mg/mL, about 300 mg/mL, about 400 mg/mL, about 500 mg/mL, or about 600 mg/mL. In some embodiments, the SBEBCD is present in an amount of at least about 50 mg/mL, about 100 mg/mL, about 200 mg/mL, about 300 mg/mL, about 400 mg/mL, or about 500 mg/mL. In some embodiments, the SBEBCD is present in an amount of at most about 100 mg/mL, about 200 mg/mL, about 300 mg/mL, about 400 mg/mL, about 500 mg/mL, or about 600 mg/mL.

In some embodiments, the pharmaceutical composition further comprises a base, a buffer, or a combination thereof.

In some embodiments, the pharmaceutical composition further comprises an emulsifying agent, a surfactant, a solubilizing agent, an emulsifying agent, a co-solvent, or a combination thereof.

In some embodiments, the pharmaceutical composition is free of excipient emulsifying agents, complexing agents, surfactant agents, or solubilizing agents.

In some embodiments, the pharmaceutical composition is a solution. In some embodiments, the pharmaceutical composition is a solid. In some embodiments, the pharmaceutical composition has a pH>about 4.

In some embodiments, the pharmaceutical composition has a pH of about 4 to about 7. In some embodiments, the pharmaceutical composition has a pH of about 4 to about 7. In some embodiments, the pharmaceutical composition has a pH of about 4 to about 4.5, about 4 to about 5, about 4 to about 5.5, about 4 to about 6, about 4 to about 6.5, about 4 to about 7, about 4.5 to about 5, about 4.5 to about 5.5, about 4.5 to about 6, about 4.5 to about 6.5, about 4.5 to about 7, about 5 to about 5.5, about 5 to about 6, about 5 to about 6.5, about 5 to about 7, about 5.5 to about 6, about 5.5 to about 6.5, about 5.5 to about 7, about 6 to about 6.5, about 6 to about 7, or about 6.5 to about 7. In some embodiments, the pharmaceutical composition has a pH of about 4, about 4.5, about 5, about 5.5, about 6, about 6.5, or about 7. In some embodiments, the pharmaceutical composition has a pH of at least about 4, about 4.5, about 5, about 5.5, about 6, or about 6.5. In some embodiments, the pharmaceutical composition has a pH of at most about 4.5, about 5, about 5.5, about 6, about 6.5, or about 7.

In some embodiments, the pharmaceutical composition has a pH of about 4.5 to about 6.5.

In some embodiments, the pharmaceutical composition has an osmolality of from about 250 mOsm/kg to about 850 mOsm/kg. In some embodiments, the pharmaceutical composition has an osmolality of from about 275 mOsm/kg to about 850 mOsm/kg. In some embodiments, the pharmaceutical composition has an osmolality of from about 300 mOsm/kg to about 850 mOsm/kg. In some embodiments, the pharmaceutical composition has an osmolality of from about 325 mOsm/kg to about 850 mOsm/kg. In some embodiments, the pharmaceutical composition has an osmolality of from about 350 mOsm/kg to about 850 mOsm/kg. In some embodiments, the pharmaceutical composition has an osmolality of from about 375 mOsm/kg to about 850 mOsm/kg. In some embodiments, the pharmaceutical composition has an osmolality of from about 400 mOsm/kg to about 850 mOsm/kg. In some embodiments, the pharmaceutical composition has an osmolality of from about 300 mOsm/kg to about 450 mOsm/kg. In some embodiments, the pharmaceutical composition has an osmolality of from about 475 mOsm/kg to about 850 mOsm/kg. In some embodiments, the pharmaceutical composition has an osmolality of from about 500 mOsm/kg to about 850 mOsm/kg.

In some embodiments, the pharmaceutical composition has an osmolality of at least about 250 mOsm/kg. In some embodiments, the pharmaceutical composition has an osmolality of at least about 275 mOsm/kg. In some embodiments, the pharmaceutical composition has an osmolality of at least about 300 mOsm/kg. In some embodiments, the pharmaceutical composition has an osmolality of at least about 325 mOsm/kg. In some embodiments, the pharmaceutical composition has an osmolality of at least about 350 mOsm/kg. In some embodiments, the pharmaceutical composition has an osmolality of at least about 375 mOsm/kg. In some embodiments, the pharmaceutical composition has an osmolality of at least about 400 mOsm/kg. In some embodiments, the pharmaceutical composition has an osmolality of at least about 425 mOsm/kg. In some embodiments, the pharmaceutical composition has an osmolality of at least about 450 mOsm/kg. In some embodiments, the pharmaceutical composition has an osmolality of at least about 475 mOsm/kg. In some embodiments, the pharmaceutical composition has an osmolality of at least about 500 mOsm/kg.

In some embodiments, the pharmaceutical composition has an osmolality of about <850 mOsm/kg. In some embodiments, the pharmaceutical composition has an osmolality of about <825 mOsm/kg. In some embodiments, the pharmaceutical composition has an osmolality of about <800 mOsm/kg. In some embodiments, the pharmaceutical composition has an osmolality of about <775 mOsm/kg. In some embodiments, the pharmaceutical composition has an osmolality of about <750 mOsm/kg. In some embodiments, the pharmaceutical composition has an osmolality of about <725 mOsm/kg. In some embodiments, the pharmaceutical composition has an osmolality of about <700 mOsm/kg. In some embodiments, the pharmaceutical composition has an osmolality of about <675 mOsm/kg. In some embodiments, the pharmaceutical composition has an osmolality of about <650 mOsm/kg. In some embodiments, the pharmaceutical composition has an osmolality of about <625 mOsm/kg. In some embodiments, the pharmaceutical composition has an osmolality of about <600 mOsm/kg. In some embodiments, the pharmaceutical composition has an osmolality of about <575 mOsm/kg. In some embodiments, the pharmaceutical composition has an osmolality of about <550 mOsm/kg. In some embodiments, the pharmaceutical composition has an osmolality of about <525 mOsm/kg. In some embodiments, the pharmaceutical composition has an osmolality of about <500 mOsm/kg. In some embodiments, the pharmaceutical composition has an osmolality of about <450 mOsm/kg. In some embodiments, the pharmaceutical composition has an osmolality of about <400 mOsm/kg. In some embodiments, the pharmaceutical composition has an osmolality of about <350 mOsm/kg.

In some embodiments, the pharmaceutical composition has an osmolality of about 300 mOsm/kg to about 850 mOsm/kg. In some embodiments, the pharmaceutical composition has an osmolality of about 300 mOsm/kg to about 350 mOsm/kg, about 300 mOsm/kg to about 400 mOsm/kg, about 300 mOsm/kg to about 450 mOsm/kg, about 300 mOsm/kg to about 500 mOsm/kg, about 300 mOsm/kg to about 550 mOsm/kg, about 300 mOsm/kg to about 600 mOsm/kg, about 300 mOsm/kg to about 650 mOsm/kg, about 300 mOsm/kg to about 700 mOsm/kg, about 300 mOsm/kg to about 750 mOsm/kg, about 300 mOsm/kg to about 800 mOsm/kg, about 300 mOsm/kg to about 850 mOsm/kg, about 350 mOsm/kg to about 400 mOsm/kg, about 350 mOsm/kg to about 450 mOsm/kg, about 350 mOsm/kg to about 500 mOsm/kg, about 350 mOsm/kg to about 550 mOsm/kg, about 350 mOsm/kg to about 600 mOsm/kg, about 350 mOsm/kg to about 650 mOsm/kg, about 350 mOsm/kg to about 700 mOsm/kg, about 350 mOsm/kg to about 750 mOsm/kg, about 350 mOsm/kg to about 800 mOsm/kg, about 350 mOsm/kg to about 850 mOsm/kg, about 400 mOsm/kg to about 450 mOsm/kg, about 400 mOsm/kg to about 500 mOsm/kg, about 400 mOsm/kg to about 550 mOsm/kg, about 400 mOsm/kg to about 600 mOsm/kg, about 400 mOsm/kg to about 650 mOsm/kg, about 400 mOsm/kg to about 700 mOsm/kg, about 400 mOsm/kg to about 750 mOsm/kg, about 400 mOsm/kg to about 800 mOsm/kg, about 400 mOsm/kg to about 850 mOsm/kg, about 450 mOsm/kg to about 500 mOsm/kg, about 450 mOsm/kg to about 550 mOsm/kg, about 450 mOsm/kg to about 600 mOsm/kg, about 450 mOsm/kg to about 650 mOsm/kg, about 450 mOsm/kg to about 700 mOsm/kg, about 450 mOsm/kg to about 750 mOsm/kg, about 450 mOsm/kg to about 800 mOsm/kg, about 450 mOsm/kg to about 850 mOsm/kg, about 500 mOsm/kg to about 550 mOsm/kg, about 500 mOsm/kg to about 600 mOsm/kg, about 500 mOsm/kg to about 650 mOsm/kg, about 500 mOsm/kg to about 700 mOsm/kg, about 500 mOsm/kg to about 750 mOsm/kg, about 500 mOsm/kg to about 800 mOsm/kg, about 500 mOsm/kg to about 850 mOsm/kg, about 550 mOsm/kg to about 600 mOsm/kg, about 550 mOsm/kg to about 650 mOsm/kg, about 550 mOsm/kg to about 700 mOsm/kg, about 550 mOsm/kg to about 750 mOsm/kg, about 550 mOsm/kg to about 800 mOsm/kg, about 550 mOsm/kg to about 850 mOsm/kg, about 600 mOsm/kg to about 650 mOsm/kg, about 600 mOsm/kg to about 700 mOsm/kg, about 600 mOsm/kg to about 750 mOsm/kg, about 600 mOsm/kg to about 800 mOsm/kg, about 600 mOsm/kg to about 850 mOsm/kg, about 650 mOsm/kg to about 700 mOsm/kg, about 650 mOsm/kg to about 750 mOsm/kg, about 650 mOsm/kg to about 800 mOsm/kg, about 650 mOsm/kg to about 850 mOsm/kg, about 700 mOsm/kg to about 750 mOsm/kg, about 700 mOsm/kg to about 800 mOsm/kg, about 700 mOsm/kg to about 850 mOsm/kg, about 750 mOsm/kg to about 800 mOsm/kg, about 750 mOsm/kg to about 850 mOsm/kg, or about 800 mOsm/kg to about 850 mOsm/kg. In some embodiments, the pharmaceutical composition has an osmolality of about 300 mOsm/kg, about 350 mOsm/kg, about 400 mOsm/kg, about 450 mOsm/kg, about 500 mOsm/kg, about 550 mOsm/kg, about 600 mOsm/kg, about 650 mOsm/kg, about 700 mOsm/kg, about 750 mOsm/kg, about 800 mOsm/kg, or about 850 mOsm/kg. In some embodiments, the pharmaceutical composition has an osmolality of at least about 300 mOsm/kg, about 350 mOsm/kg, about 400 mOsm/kg, about 450 mOsm/kg, about 500 mOsm/kg, about 550 mOsm/kg, about 600 mOsm/kg, about 650 mOsm/kg, about 700 mOsm/kg, about 750 mOsm/kg, or about 800 mOsm/kg. In some embodiments, the pharmaceutical composition has an osmolality of at most about 350 mOsm/kg, about 400 mOsm/kg, about 450 mOsm/kg, about 500 mOsm/kg, about 550 mOsm/kg, about 600 mOsm/kg, about 650 mOsm/kg, about 700 mOsm/kg, about 750 mOsm/kg, about 800 mOsm/kg, or about 850 mOsm/kg.

In some embodiments, the pharmaceutical composition is isotonic.

In some embodiments, the pharmaceutical composition has an osmolality of about 500 mOsm/kg.

In some embodiments, the compound of Formula (I) or an enantiomer, a mixture of enantiomers, or an isotopic variant thereof; or solvate or hydrate thereof, has a concentration of about 20 mg/mL to about 150 mg/mL. In some embodiments, the compound of Formula (I) or an enantiomer, a mixture of enantiomers, or an isotopic variant thereof; or solvate or hydrate thereof, has a concentration up to about 150 mg/mL. In some embodiments, the compound of Formula (I) or an enantiomer, a mixture of enantiomers, or an isotopic variant thereof; or solvate or hydrate thereof, has a concentration at least about 20 mg/mL.

In some embodiments, the compound of Formula (I), or an enantiomer, a mixture of enantiomers, or an isotopic variant thereof; or solvate or hydrate thereof, has a concentration of about 80 mg/mL to about 120 mg/mL.

In some embodiments, the compound of Formula (I), or an enantiomer, a mixture of enantiomers, or an isotopic variant thereof; or solvate or hydrate thereof, has a concentration of about 95 mg/mL to about 105 mg/mL.

In some embodiments, the compound of Formula (I), or an enantiomer, a mixture of enantiomers, or an isotopic variant thereof; or solvate or hydrate thereof, has a concentration of about 20 mg/mL. In some embodiments, the compound of Formula (I), or an enantiomer, a mixture of enantiomers, or an isotopic variant thereof; or solvate or hydrate thereof, has a concentration of about 25 mg/mL. In some embodiments, the compound of Formula (I), or an enantiomer, a mixture of enantiomers, or an isotopic variant thereof; or solvate or hydrate thereof, has a concentration of about 30 mg/mL. In some embodiments, the compound of Formula (I), or an enantiomer, a mixture of enantiomers, or an isotopic variant thereof; or solvate or hydrate thereof, has a concentration of about 35 mg/mL. In some embodiments, the compound of Formula (I), or an enantiomer, a mixture of enantiomers, or an isotopic variant thereof; or solvate or hydrate thereof, has a concentration of about 40 mg/mL. In some embodiments, the compound of Formula (I), or an enantiomer, a mixture of enantiomers, or an isotopic variant thereof; or solvate or hydrate thereof, has a concentration of about 45 mg/mL. In some embodiments, the compound of Formula (I), or an enantiomer, a mixture of enantiomers, or an isotopic variant thereof; or solvate or hydrate thereof, has a concentration of about 50 mg/mL. In some embodiments, the compound of Formula (I), or an enantiomer, a mixture of enantiomers, or an isotopic variant thereof; or solvate or hydrate thereof, has a concentration of about 55 mg/mL. In some embodiments, the compound of Formula (I), or an enantiomer, a mixture of enantiomers, or an isotopic variant thereof; or solvate or hydrate thereof, has a concentration of about 60 mg/mL. In some embodiments, the compound of Formula (I), or an enantiomer, a mixture of enantiomers, or an isotopic variant thereof; or solvate or hydrate thereof, has a concentration of about 65 mg/mL. In some embodiments, the compound of Formula (I), or an enantiomer, a mixture of enantiomers, or an isotopic variant thereof; or solvate or hydrate thereof, has a concentration of about 70 mg/mL. In some embodiments, the compound of Formula (I), or an enantiomer, a mixture of enantiomers, or an isotopic variant thereof; or solvate or hydrate thereof, has a concentration of about 75 mg/mL. In some embodiments, the compound of Formula (I), or an enantiomer, a mixture of enantiomers, or an isotopic variant thereof; or solvate or hydrate thereof, has a concentration of about 80 mg/mL. In some embodiments, the compound of Formula (I), or an enantiomer, a mixture of enantiomers, or an isotopic variant thereof; or solvate or hydrate thereof, has a concentration of about 85 mg/mL. In some embodiments, the compound of Formula (I), or an enantiomer, a mixture of enantiomers, or an isotopic variant thereof; or solvate or hydrate thereof, has a concentration of about 90 mg/mL. In some embodiments, the compound of Formula (I), or an enantiomer, a mixture of enantiomers, or an isotopic variant thereof; or solvate or hydrate thereof, has a concentration of about 95 mg/mL. In some embodiments, the compound of Formula (I), or an enantiomer, a mixture of enantiomers, or an isotopic variant thereof; or solvate or hydrate thereof, has a concentration of about 100 mg/mL. In some embodiments, the compound of Formula (I), or an enantiomer, a mixture of enantiomers, or an isotopic variant thereof; or solvate or hydrate thereof, has a concentration of about 105 mg/mL. In some embodiments, the compound of Formula (I), or an enantiomer, a mixture of enantiomers, or an isotopic variant thereof; or solvate or hydrate thereof, has a concentration of about 110 mg/mL. In some embodiments, the compound of Formula (I), or an enantiomer, a mixture of enantiomers, or an isotopic variant thereof; or solvate or hydrate thereof, has a concentration of about 115 mg/mL. In some embodiments, the compound of Formula (I), or an enantiomer, a mixture of enantiomers, or an isotopic variant thereof; or solvate or hydrate thereof, has a concentration of about 120 mg/mL. In some embodiments, the compound of Formula (I), or an enantiomer, a mixture of enantiomers, or an isotopic variant thereof; or solvate or hydrate thereof, has a concentration of about 125 mg/mL. In some embodiments, the compound of Formula (I), or an enantiomer, a mixture of enantiomers, or an isotopic variant thereof; or solvate or hydrate thereof, has a concentration of about 130 mg/mL. In some embodiments, the compound of Formula (I), or an enantiomer, a mixture of enantiomers, or an isotopic variant thereof; or solvate or hydrate thereof, has a concentration of about 135 mg/mL. In some embodiments, the compound of Formula (I), or an enantiomer, a mixture of enantiomers, or an isotopic variant thereof; or solvate or hydrate thereof, has a concentration of about 140 mg/mL. In some embodiments, the compound of Formula (I), or an enantiomer, a mixture of enantiomers, or an isotopic variant thereof; or solvate or hydrate thereof, has a concentration of about 145 mg/mL. In some embodiments, the compound of Formula (I), or an enantiomer, a mixture of enantiomers, or an isotopic variant thereof; or solvate or hydrate thereof, has a concentration of about 150 mg/mL.

In some embodiments, the compound of Formula (I), or an enantiomer, a mixture of enantiomers, or an isotopic variant thereof; or solvate or hydrate thereof, has a concentration of about 95 mg/mL, about 96 mg/mL, about 97 mg/mL, about 98 mg/mL, about 99 mg/mL, about 100 mg/mL, about 101 mg/mL, 102 mg/mL, about 103 mg/mL, about 104 mg/mL, or about 105 mg/mL.

In some embodiments, the compound of Formula (I) or an enantiomer, a mixture of enantiomers, or an isotopic variant thereof; or solvate or hydrate thereof, has a concentration of about 20 mg/mL to about 150 mg/mL. In some embodiments, the compound of Formula (I) or an enantiomer, a mixture of enantiomers, or an isotopic variant thereof; or solvate or hydrate thereof, has a concentration of about 20 mg/mL to about 40 mg/mL, about 20 mg/mL to about 60 mg/mL, about 20 mg/mL to about 80 mg/mL, about 20 mg/mL to about 100 mg/mL, about 20 mg/mL to about 120 mg/mL, about 20 mg/mL to about 140 mg/mL, about 20 mg/mL to about 150 mg/mL, about 40 mg/mL to about 60 mg/mL, about 40 mg/mL to about 80 mg/mL, about 40 mg/mL to about 100 mg/mL, about 40 mg/mL to about 120 mg/mL, about 40 mg/mL to about 140 mg/mL, about 40 mg/mL to about 150 mg/mL, about 60 mg/mL to about 80 mg/mL, about 60 mg/mL to about 100 mg/mL, about 60 mg/mL to about 120 mg/mL, about 60 mg/mL to about 140 mg/mL, about 60 mg/mL to about 150 mg/mL, about 80 mg/mL to about 100 mg/mL, about 80 mg/mL to about 120 mg/mL, about 80 mg/mL to about 140 mg/mL, about 80 mg/mL to about 150 mg/mL, about 100 mg/mL to about 120 mg/mL, about 100 mg/mL to about 140 mg/mL, about 100 mg/mL to about 150 mg/mL, about 120 mg/mL to about 140 mg/mL, about 120 mg/mL to about 150 mg/mL, or about 140 mg/mL to about 150 mg/mL. In some embodiments, the compound of Formula (I) or an enantiomer, a mixture of enantiomers, or an isotopic variant thereof; or solvate or hydrate thereof, has a concentration of about 20 mg/mL, about 40 mg/mL, about 60 mg/mL, about 80 mg/mL, about 100 mg/mL, about 120 mg/mL, about 140 mg/mL, or about 150 mg/mL. In some embodiments, the compound of Formula (I) or an enantiomer, a mixture of enantiomers, or an isotopic variant thereof; or solvate or hydrate thereof, has a concentration of at least about 20 mg/mL, about 40 mg/mL, about 60 mg/mL, about 80 mg/mL, about 100 mg/mL, about 120 mg/mL, or about 140 mg/mL. In some embodiments, the compound of Formula (I) or an enantiomer, a mixture of enantiomers, or an isotopic variant thereof; or solvate or hydrate thereof, has a concentration of at most about 40 mg/mL, about 60 mg/mL, about 80 mg/mL, about 100 mg/mL, about 120 mg/mL, about 140 mg/mL, or about 150 mg/mL.

In some embodiments, the pharmaceutical composition further comprises a preservative. In some embodiments, the preservative is benzethonium chloride. In some embodiments, the benzethonium chloride is present in an amount of about 0.1 mg/mL to about 0.5 mg/mL. In some embodiments, the preservative is benzethonium chloride, benzalkonium chloride, or chloroxylenol. Other preservatives include benzyl alcohol, methyl parabens, ethyl or n-propyl, and p-hydroxybenzoate. In some embodiments, preservatives are antimicrobial agents, including, but not limited to: Phenol, Meta-cresol, Benzyl alcohol, parabens (methyl, propyl, or butyl), benzalkonium chloride, benzethonium chloride, chlorobutanol, Myristyl gamma picolinium chloride, 2-phenoxyethanol, Phenethyl alcohol, Sorbates (sorbic acid, sodium sorbate), Ethanol, and/or Propylene glycol. In some embodiments, the preservative is present in an amount of about 0.1 mg/mL to about 1 mg/mL. In some embodiments, the preservative is present in an amount of about 0.1 mg/mL to about 0.2 mg/mL, about 0.1 mg/mL to about 0.3 mg/mL, about 0.1 mg/mL to about 0.4 mg/mL, about 0.1 mg/mL to about 0.5 mg/mL, about 0.1 mg/mL to about 0.6 mg/mL, about 0.1 mg/mL to about 0.7 mg/mL, about 0.1 mg/mL to about 0.8 mg/mL, about 0.1 mg/mL to about 0.9 mg/mL, about 0.1 mg/mL to about 1 mg/mL, about 0.2 mg/mL to about 0.3 mg/mL, about 0.2 mg/mL to about 0.4 mg/mL, about 0.2 mg/mL to about 0.5 mg/mL, about 0.2 mg/mL to about 0.6 mg/mL, about 0.2 mg/mL to about 0.7 mg/mL, about 0.2 mg/mL to about 0.8 mg/mL, about 0.2 mg/mL to about 0.9 mg/mL, about 0.2 mg/mL to about 1 mg/mL, about 0.3 mg/mL to about 0.4 mg/mL, about 0.3 mg/mL to about 0.5 mg/mL, about 0.3 mg/mL to about 0.6 mg/mL, about 0.3 mg/mL to about 0.7 mg/mL, about 0.3 mg/mL to about 0.8 mg/mL, about 0.3 mg/mL to about 0.9 mg/mL, about 0.3 mg/mL to about 1 mg/mL, about 0.4 mg/mL to about 0.5 mg/mL, about 0.4 mg/mL to about 0.6 mg/mL, about 0.4 mg/mL to about 0.7 mg/mL, about 0.4 mg/mL to about 0.8 mg/mL, about 0.4 mg/mL to about 0.9 mg/mL, about 0.4 mg/mL to about 1 mg/mL, about 0.5 mg/mL to about 0.6 mg/mL, about 0.5 mg/mL to about 0.7 mg/mL, about 0.5 mg/mL to about 0.8 mg/mL, about 0.5 mg/mL to about 0.9 mg/mL, about 0.5 mg/mL to about 1 mg/mL, about 0.6 mg/mL to about 0.7 mg/mL, about 0.6 mg/mL to about 0.8 mg/mL, about 0.6 mg/mL to about 0.9 mg/mL, about 0.6 mg/mL to about 1 mg/mL, about 0.7 mg/mL to about 0.8 mg/mL, about 0.7 mg/mL to about 0.9 mg/mL, about 0.7 mg/mL to about 1 mg/mL, about 0.8 mg/mL to about 0.9 mg/mL, about 0.8 mg/mL to about 1 mg/mL, or about 0.9 mg/mL to about 1 mg/mL. In some embodiments, the preservative is present in an amount of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, or about 1 mg/mL. In some embodiments, the preservative is present in an amount of about at least about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, or about 0.9 mg/mL. In some embodiments, the preservative is present in an amount of about at most about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, or about 1 mg/mL.

In some embodiments of the pharmaceutical compositions disclosed herein, the form is a subcutaneous (e.g., infusion or bolus) dosage form. In some embodiments of the pharmaceutical composition, wherein the form is a subcutaneous dosage form, the pH is from about 3.0 to about 7.0. In some embodiments of the pharmaceutical composition, wherein the form is a subcutaneous dosage form, the pH is from about 4.0 to about 5.0. In some embodiments of the pharmaceutical composition, wherein the form is a subcutaneous dosage form, the pH is from about 4.5 to about 5.5. In some embodiments of the pharmaceutical composition, wherein the form is a subcutaneous dosage form, the pH is from about 5.0 to about 6.0. In some embodiments of the pharmaceutical composition, wherein the form is a subcutaneous dosage form, the pH is from about 5.5 to about 6.5. In some embodiments of the pharmaceutical composition, wherein the form is a subcutaneous dosage form, the pH is from about 6.0 to about 7.0. In some embodiments of the pharmaceutical composition, wherein the form is a subcutaneous dosage form, the pH is about 3.0. In some embodiments of the pharmaceutical composition, wherein the form is a subcutaneous dosage form, the pH is about 3.5. In some embodiments of the pharmaceutical composition, wherein the form is a subcutaneous dosage form, the pH is about 4.0. In some embodiments of the pharmaceutical composition, wherein the form is a subcutaneous dosage form, the pH is about 4.5. In some embodiments of the pharmaceutical composition, wherein the form is a subcutaneous dosage form, the pH is about 5.0. In some embodiments of the pharmaceutical composition, wherein the form is a subcutaneous dosage form, the pH is about 5.1. In some embodiments of the pharmaceutical composition, wherein the form is a subcutaneous dosage form, the pH is about 5.2. In some embodiments of the pharmaceutical composition, wherein the form is a subcutaneous dosage form, the pH is about 5.3. In some embodiments of the pharmaceutical composition, wherein the form is a subcutaneous dosage form, the pH is about 5.4. In some embodiments of the pharmaceutical composition, wherein the form is a subcutaneous dosage form, the pH is about 5.5. In some embodiments of the pharmaceutical composition, wherein the form is a subcutaneous dosage form, the pH is about 5.6. In some embodiments of the pharmaceutical composition, wherein the form is a subcutaneous dosage form, the pH is about 5.7. In some embodiments of the pharmaceutical composition, wherein the form is a subcutaneous dosage form, the pH is about 5.8. In some embodiments of the pharmaceutical composition, wherein the form is a subcutaneous dosage form, the pH is about 5.9. In some embodiments of the pharmaceutical composition, wherein the form is a subcutaneous dosage form, the pH is about 6.0. In some embodiments of the pharmaceutical composition, wherein the form is a subcutaneous dosage form, the pH is about 6.5. In some embodiments of the pharmaceutical composition, wherein the form is a subcutaneous dosage form, the pH is about 7.0.

The compounds (e.g., NMDA receptor antagonists (e.g., ketamine)) of the present disclosure may be in the form of compositions suitable for administration to a subject. In general, such compositions are "pharmaceutical compositions" comprising a compound (e.g., NMDA receptor antagonists (e.g., ketamine)) and one or more pharmaceutically acceptable or physiologically acceptable diluents, carriers or excipients. In some embodiments, the compounds (e.g., NMDA receptor antagonists (e.g., ketamine)) are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

In certain embodiments of the pharmaceutical compositions described herein, the co-solvent comprises PEG200, PEG300, PEG400, PEG600, propylene glycol, ethanol, polysorbate 20, polysorbate 80, cremephor, glycerin, benzyl alcohol, dimethylacetamide (DMA), N-methyl-2-pyrrolidone (NMP), tert-butanol, or combinations thereof.

In certain embodiments, the dosage form or pharmaceutical composition comprises a surface-active agent.

In certain embodiments of the pharmaceutical compositions described herein, the surface-active agent comprises polyoxyethylene sorbitan monooleate (Tween 80), sorbitan monooleate, polyoxyethylene sorbitan monolaurate (Tween 20), lecithin, polyoxyethylene-polyoxypropylene copolymers (Pluronics 1), or combinations thereof.

In certain embodiments, the dosage form or pharmaceutical composition comprises a non-ionic surfactant.

In certain embodiments of the pharmaceutical compositions described herein, the non-ionic surfactant comprises Cremophor RH40, Cremophor RH60, d-alpha-topopherol polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, or combinations thereof.

In certain embodiments of the pharmaceutical compositions described herein, the NMDA receptor antagonist or modulator is racemic ketamine, (R)-ketamine, or (S)-ketamine.

In some embodiments, the pharmaceutical composition comprises one or more co-solvents, solubilization/solubilizing agents, stabilization agents, antioxidants, preservatives, cryoprotectants, lyoprotectants, bulking agents, tonicity-adjusting agents, or antimicrobial agents. In some embodiments, the pharmaceutical composition comprises at least one co-solvent. In some embodiments, the pharmaceutical composition comprises at least one solubilizing agent. In some embodiments, the pharmaceutical composition comprises at least one stabilization agent. In some embodiments, the pharmaceutical composition comprises at least one antioxidant. In some embodiments, the pharmaceutical composition comprises at least one preservative. In some embodiments, the pharmaceutical composition comprises at least one cryoprotectant. In some embodiments, the pharmaceutical composition comprises at least one lyoprotectant. In some embodiments, the pharmaceutical composition comprises at least one bulking agent. In some embodiments, the pharmaceutical composition comprises at least one tonicity-adjusting agent. In some embodiments, the pharmaceutical composition comprises at least one antimicrobial agent.

In some embodiments, the formulation or pharmaceutical composition is a pharmaceutical composition. In some embodiments, the formulation is in the form of a sterile injectable aqueous or oleaginous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin). In some embodiments, the formulation comprises a co-solvent. In some embodiments, a suitable co-solvent is propylene glycol, glycerin, ethanol, polyethylene glycol (300 and 400), Sorbitol, dimethylacetamide, Cremophor EL, or N-methyl-2-pyrrolidone, or dimethylsulfoxide.

In some embodiments, the formulation or pharmaceutical composition is an aqueous suspension. Aqueous suspensions contain active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives (e.g. benzethonium chloride).

In some embodiments, the formulation or pharmaceutical composition comprises a stabilisation agent. In some embodiments, the formulation comprises a surface-active solubilization agent. Surface-active solubilization agents include, but are not limited to: polyoxyethylene sorbitan monooleate (Tween 80), sorbitan monooleate, polyoxyethylene sorbitan monolaurate (Tween 20), lecithin, and Polyoxyethylene-polyoxypropylene copolymers (Pluronics 1). In some embodiments, the formulation comprises a non-ionic surfactant solubilization agent. Non-ionic surfactants include, but are not limited: Cremophor RH 40, Cremophor RH 60, d-alpha-tocopherol polyethylene glycol 1000 succinate, polysorbate 20, polysorbate 80, Solutol HS 1, sorbitan monooleate, poloxamer 407, Labrafil M-1944CS, Labrafil M-2125CS, Labrasol, Gellucire 44/14, Softigen 767, and mono-fatty esters and di-fatty acid esters of PEG 300, 400, and 1750. In some embodiments, the formulation comprises a phospholipid solubilizing agent such as, hydrogenated soy phosphatidylcholine, phosphatidylcholine, distearoylphosphatidylglycerol, L-alpha-dimyristoylphosphatidylcholine, or L-alpha-dimyristoylphosphatidylglycerol.

In some embodiments, the formulation or pharmaceutical composition comprises a complexation agent. In some embodiments, the complexation agent is hydroxypropyl-b-cyclodextrin, bulfobutylether-b-cyclodextrin (Captisol1), or polyvinylpyrrolidone. In some embodiments, the complexation agent is an amino acid such as, arginine, lysine, or histidine. In some embodiments, the formulation or pharmaceutical composition comprises a cyclodextrin excipient. Cyclodextrin excipients are used to enhance the stability, tolerability and absorption of compounds in parenteral aqueous solutions. Common cyclodextrin excipients include but are not limited to: alpha-Cyclodextrin (alpha-CD), beta-Cyclodextrin (beta-CD), gamma-Cyclodextrin (gamma-CD), Diethyl-ethyl-beta-cyclodextrin (DE-beta-CD), Dimethyl-ethyl-beta-cyclodextrin (DM-beta-CD), Hydroxypropyl-beta-cyclodextrin (HP-beta-CD), Hydroxypropyl-gamma-cyclodextrin (HP-gamma-CD), Methyl-b-cyclodextrin (M-beta-CD), Sulfobutylether-beta-cyclodextrin (SBE-beta-CD), Randomly methylated-beta-CD (RM-beta-CD), Maltosyl-beta-CD (mal-beta-CD), Hydroxypropyl-alpha-CD.

The formulations or pharmaceutical compositions of the present disclosure may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The formulation or pharmaceutical composition typically comprises a therapeutically effective amount of an active compound (e.g. an NMDA receptor antagonist, such as ketamine), or a hydrate, solvate, tautomer, or pharmaceutically acceptable salt thereof, and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a triethanolamine (Tris) buffer, histidine, bicarbonate; N-(2-Hydroxyethyl)piperazine-N'-(2-ethanesulfonic acid) (HEPES); 2-(N-Morpholino)ethanesulfonic acid (WS); 2-(N-Morpholino)ethanesulfonic acid sodium salt (WS); 3-(N-Morpholino)propanesulfonic acid (MOPS); and N-tris [Hydroxymethyl]methyl-3-aminopropane sulfonic acid (TAPS).

Many active pharmaceutical ingredients (APIs) are weak acids or weak bases. Weak acids or weak bases can exist in an un-ionized form or as an ionized complex prepared by the addition of a base or acid respectively. The resultant complex is stabilized by ionic interactions and is known as a salt. This complex exists via an ionic bond between an ionized API and an oppositely charged counterion. Salts offer a number of advantages over their un-ionized counterparts. The choice of counterion can have a large influence on the salts properties and the use of a given salt form of a given API in a pharmaceutical product is influenced and guided by a number of factors for example stability (photo, hydrolytic and thermal), solubility, physicochemical properties, solid state properties (crystallinity, polymorphism, particle size, crystal morphology, melting point, compactability), production considerations (e.g., ease of handling and processing), dissolution rate, modulation of drug release, compatibility with excipients and containers, ease and consistency of production, desired route of administration, and organoleptic factors (e.g., taste). Furthermore, with respect to injection, salt can influence pain and irritation at the injection site.

APIs that are weak acids or weak bases can act as their own buffers at pH's near the pKa of the API. For example, ketamine comprises an amino functionality with a pKa of ~7.5, and can thus serve as a buffer in the region of about ±2 pH units from the pKa (e.g. from pHs of about 5.5 to about 9.5). When the formulation has a target pH within this range, an additional buffer may not be required. In some embodiments, the pharmaceutical composition provided herein does not comprise an additional buffer.

With regard to cyclodextrin solubilization, specific salts of various APIs have been found to form multicomponent complexes/systems or ternary systems which can have distinct desirable properties as compared to their standard binary complexes/systems counterparts prepared between the cyclodextrin and the un-ionized API, as well as compared to other multicomponent ternary complexes/systems involving different salt forms of that API. These multicomponent complexes/systems can thus dramatically influence solubility of the API in aqueous solutions, dissolution rates, can influence product stability, and pharmacokinetic properties of the pharmaceutical preparation.

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations or pharmaceutical compositions can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver an NMDA receptor antagonist, including implants (e.g., implantable pumps) and catheter systems, slow injection pumps and devices, all of which are well known to the skilled artisan.

In some embodiments, the formulation or pharmaceutical composition is stored in a reservoir of the drug delivery device. In some embodiments, the formulation is stored in a cartridge that is insertable and/or attachable to the drug delivery device. In some embodiments, the cartridge and/or drug delivery device comprises a product label for intramuscular injection. In some embodiments, the cartridge and/or drug delivery device comprises a product label for subcutaneous injection. In some embodiments, the cartridge and/or drug delivery device comprises a product label for intravenous injection. In some embodiments, disclosed herein is a kit comprising a product label for intramuscular injection. In some embodiments, disclosed herein is a kit comprising a product label for subcutaneous injection. In some embodiments, disclosed herein is a kit comprising a product label for intravenous injection.

In some embodiments, the formulation or pharmaceutical composition is a liquid formulation comprising ketamine hydrochloride (HCl). In some embodiments, the formulation comprises a racemic ketamine composition. Alternatively, In some embodiments, the formulation comprises a substantially pure stereoisomer of ketamine (e.g., over 90%, 95%, 96%, 97%, 98%, or 99% of the ketamine is one stereoisomer). In some embodiments, the formulation comprises substantially pure S-ketamine. In some embodiments, the formulation comprises substantially pure R-ketamine. In some embodiments, the NMDA receptor antagonist is at least about 90%, about 95%, about 96%, about 97%, about 98%, or about 99% pure. In some embodiments, the NMDA receptor antagonist is at least about 99.1%, about 99.2%, about 99.3%, about 99.4%, about 99.5%, about 99.6%, about 99.8%, or about 99.9% pure. In some embodiments, the NMRA receptor antagonist comprises less than about 5%, about 4%, about 3%, about 2%, or about 1% impurities.

In some embodiments, the formulation or pharmaceutical composition is a liquid formulation comprising ketamine free base. In some embodiments, the formulation or pharmaceutical composition is a liquid formulation comprising non-ionized ketamine (i.e., free base). In some embodiments, the formulation or pharmaceutical composition is a liquid formulation comprising ketamine in a mixture of ionized and non-ionized (free base) forms.

In some embodiments, the formulation comprises a racemic ketamine composition.

Alternatively, In some embodiments, the formulation comprises a substantially pure stereoisomer of ketamine (e.g., over 90%, 95%, 96%, 97%, 98%, or 99% of the ketamine is one stereoisomer). In some embodiments, the formulation comprises substantially pure S-ketamine. In some embodiments, the formulation comprises substantially pure R-ketamine. In some embodiments, the NMDA receptor antagonist is at least about 90%, about 95%, about 96%, about 97%, about 98%, or about 99% pure. In some embodiments, the NMDA receptor antagonist is at least about 99.1%, about 99.2%, about 99.3%, about 99.4%, about 99.5%, about 99.6%, about 99.8%, or about 99.9% pure. In some embodiments, the NMRA receptor antagonist comprises less than about 5%, about 4%, about 3%, about 2%, or about 1% impurities.

It is frequently beneficial to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity. Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

The NMDA receptor antagonist of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of the NMDA receptor antagonist of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In embodiments, the dosage of the NMDA receptor antagonist is contained in a "unit dosage form." The phrase "unit dosage form" refers to physically discrete units, each unit including a predetermined amount of the compound (e.g., ketamine, or a hydrate, solvate, or pharmaceutically acceptable salt thereof), sufficient to produce the desired effect. It will be appreciated that the parameters of a unit dosage form will depend on the particular agent and the effect to be achieved.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

Depot injections, which are generally administered subcutaneously or intramuscularly, may also be utilized to release the compound (e.g., NMDA receptor antagonist (e.g., ketamine)) disclosed herein over a defined period of time. Depot injections are usually either solid- or oil-based and generally comprise at least one of the formulation components set forth herein. One of ordinary skill in the art is familiar with possible formulations and uses of depot injections.

Some formulations include one or more stabilization agents. Potential stabilization agents that are contemplated include buffers: Acetate, Citrate, Sodium Citrate, Tartrate, Phosphate, histidine, bicarbonate, Triethanolamine (TRIS) and their salts. In some formulations, the potential stabilization agents might include antioxidants and preservatives such as: Ascorbic acid, Acetylcysteine (NAC), Sulfurous acid salts (bisulfite, metabisulfite), Monothioglyercol. Butylated hydroxyanisole (BHA), Butylated hydroxytoluene (BHT), Tert-butylhydroquinone (TBHQ), 2',4',5'-Trihydroxybutyrophenone phenylhydrazone (THBP), Ethylenediaminetetraacetic acid (EDTA), Sodium formaldehyde sulfoxylate (SFS), Tocopherol (Vitamin E), Ascorbyl palmitate, Gallates (e.g., propyl gallate, octyl gallate, lauryl gallate), Cysteine ethyl ether, Tartaric acid, Phosphoric acid, Thiourea, Sodium thioglycolate, Nitrogen, and/or Argon.

In some formulations, the potential stabilization agents might include bulking agents, cryoprotectants, and lyoprotectants. Agents that were considered include: Mannitol, Glycine, Sucrose, Lactose, Trehalose, Dextran, Povidone, Sorbitol and/or Polydextrose. In some formulations potential stabilization agents might include tonicity-adjusting agents. Agents that were considered include: sodium chloride, Glycerin, Mannitol, Dextrose, and/or glycerol. In some formulations the potential stabilization agents might include antimicrobial agents including, but not limited to: Phenol, Meta-cresol, Benzyl alcohol, parabens (methyl, propyl, or butyl), benzalkonium chloride, benzethonium chloride, chlorobutanol, Myristyl gamma picolinium chloride, 2-phenoxyethanol, Phenethyl alcohol, Sorbates (sorbic acid, sodium sorbate), Ethanol, and/or Propylene glycol.

In some formulations, soothing agents might include topical analgesics such as: lidocaine, benzocaine, tetracaine, bupivicaine, ropivacaine, and/or levobupivacaine.

In some formulations, emulsion stabilisers include hydroxyethyl cellulose, hydroxypropylcellulose, and/or hydroxypropyl methyl cellulose (hypromellose).

The compound (e.g., NMDA receptor antagonist (e.g., ketamine)) contemplated by the present disclosure may be in the form of any other suitable pharmaceutical composition currently known or developed in the future.

III. Methods

In an aspect, provided herein is a method of treating pain, comprising administering to a subject in need thereof a therapeutically effective amount of a compound of structural Formula (I):

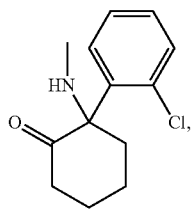

(I)

or an enantiomer, a mixture of enantiomers, or an isotopic variant thereof; or a pharmaceutically acceptable salt, solvate or hydrate thereof,
wherein the compound of Formula (I) is administered by subcutaneous injection. In some embodiments, the compound of Formula (I) is administered as any of the pharmaceutical compositions provided herein.

In some embodiments, the pain is acute pain or chronic pain. In some embodiments, the pain is acute pain. In some embodiments, the pain is post-operative pain. In some embodiments, the pain is from a traumatic injury, such as a battlefield wound. In some embodiments, the pain is cancer pain.

In an aspect, provided herein is a method of treating a psychiatric disorder, a cognitive disorder, or a neurological disorder, comprising administering to a subject in need thereof a therapeutically effective amount of a compound of structural Formula (I):

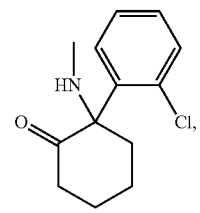

(I)

or an enantiomer, a mixture of enantiomers, or an isotopic variant thereof; or a pharmaceutically acceptable salt, solvate or hydrate thereof,
wherein the compound of Formula (I) is administered by subcutaneous injection. In some embodiments, the compound of Formula (I) is administered as any of the pharmaceutical compositions provided herein.

In some embodiments, the psychiatric disorder is major depressive disorder, treatment resistant major depressive disorder, suicidality, suicidal ideation, dysthymia or persistent depressive disorder, bipolar depressive disorder type I, bipolar depressive disorder type II, chronic pain, eating disorder NOS, pain disorder NOS, panic disorder, post-traumatic stress disorder, obsessive-compulsive disorder, complex regional pain syndrome, reflex sympathetic dystrophy, or any combination thereof.

In some embodiments, the cognitive disorder, or a neurological disorder is Huntington's disease, Parkinson's disease, frontotemporal dementia, dementia, Alzheimer's disease, amyotrophic lateral sclerosis, spinal cord trauma, stroke, diffuse traumatic brain injury, HIV-associated dementia, epilepsy, Rett syndrome, dyskinesia, unspecified dystonia, or pseudobulbar affect.

In some embodiments, the compound of Formula (I), or an enantiomer, a mixture of enantiomers, or an isotopic variant thereof; or solvate or hydrate thereof, is administered as a low volume infusion.

In another aspect is provided a method of treating, preventing, or ameliorating at least one symptom of a disorder, disease, or condition with the pharmaceutical compositions disclosed herein, including embodiments, wherein the disorder, disease, or condition is a mental or psychiatric disorder, a mood disorder, a neurological condition or disorder, type 2 diabetes mellitus and/or complications thereof, endometriosis, glaucoma, pain, or an inflammatory disorder.

Treatment of Physical, Psychiatric, or Neurological Disorders

Disclosed herein are systems, devices, kits, formulations, and methods for the treatment of one or more medical and/or psychiatric disorders. In some embodiments, a psychiatric disorder is a major depressive disorder, treatment resistant major depressive disorder, suicidality, suicidal ideation, dysthymia or persistent depressive disorder, bipolar depressive disorder type I, bipolar depressive disorder type II, chronic pain, eating disorder NOS, pain disorder NOS, panic disorder, post-traumatic stress disorder, obsessive-compulsive disorder, complex regional pain syndrome, or reflex sympathetic dystrophy. In some embodiments, the psychiatric disorder being treated is depression, major depressive disorder, or treatment resistant major depression.

In some embodiments, formulations and methods disclosed herein are used to administer the drug formulation according to the at least one dosage regimen for treating chronic pain. In some embodiments, the dosage regimen is configured for treating acute pain. In some embodiments, the dosage regimen is configured treating for chronic regional pain syndrome. In some embodiments, the dosage regimen is configured for treating pain associated with Ehlers-Danlos Syndrome. In some embodiments, the dosage regimen is configured for treating post laminectomy syndrome. In some embodiments, the dosage regimen is configured for treating pain associated with post laminectomy syndrome. In some embodiments, the dosage regimen is configured for treating failed back syndrome. In some embodiments, the dosage regimen is configured for treating pain associated with failed back syndrome. In some embodiments, the dosage regimen is configured for treating post-operative pain. In some embodiments, the dosage regimen is configured for treating diabetic neuropathy.

In some embodiments, formulations and methods disclosed herein are used to treat one or more personality disorders. Examples of personality disorders include avoidant personality disorder, dependent personality disorder, antisocial personality disorder, histrionic personality disorder, borderline personality disorder, obsessive-compulsive personality disorder, cyclothymic personality disorder, obsessive compulsive disorder, and impulse control disorder (NOS).

In some embodiments, formulations and methods disclosed herein are used to treat one or more eating disorders. Examples of eating disorders include anorexia nervosa and bulimia disorder.

In some embodiments, formulations and methods disclosed herein are used to treat brain cancer. In some embodiments, the formulations and methods disclosed herein are used to treat a glioma. In some embodiments, administration of a drug formulation provided herein slows the growth of a glioma. In some embodiments, the glioma is a glioblastoma multiforme. In some embodiments, the glioma is an astrocytoma.

In some embodiments, formulations and methods disclosed herein are used to treat one or more of major depressive disorder, treatment resistant major depressive disorder, suicidality, suicidal ideation, dysthymia, bipolar disorder (Type I—Depressed), bipolar disorder (Type II—Depressed), post-traumatic stress disorder (PTSD), panic disorder, generalized anxiety disorder, and substance abuse induced mood disorder.

In some embodiments, formulations and methods disclosed herein are used to treat a cognitive or neurological disorder or condition such as Huntington's disease, Parkinson's disease, frontotemporal dementia, dementia, Alzheimer's disease, amyotrophic lateral sclerosis, spinal cord trauma, stroke, diffuse traumatic brain injury, HIV-associated dementia, epilepsy, suicidal ideation, Rett syndrome, dyskinesia, dystonia (unspecified), or pseudobulbar affect.

Disclosed herein are systems, devices, and methods for the treatment of one or more medical and/or psychiatric disorders. In some embodiments, a psychiatric disorder is a major depressive disorder, treatment resistant major depressive disorder, suicidality, suicidal ideation, dysthymia or persistent depressive disorder, bipolar depressive disorder type I, bipolar depressive disorder type II, chronic pain, eating disorder NOS, pain disorder NOS, panic disorder, post-traumatic stress disorder, obsessive-compulsive disorder, complex regional pain syndrome, or reflex sympathetic dystrophy. In some embodiments, the psychiatric disorder being treated is depression, major depressive disorder, or treatment resistant major depression.

In some embodiments, a medical or psychiatric disorder is selected from the group consisting of major depressive disorder, treatment resistant major depressive disorder, suicidality, suicidal ideation, dysthymia, bipolar disorder— type I—depressed, bipolar disorder—type II—depressed, post-traumatic stress disorder, impulse control disorder NOS, personality disorder NOS, avoidant personality disorder, dependent personality disorder, antisocial personality disorder, histrionic personality disorder, borderline personality disorder, obsessive-compulsive personality disorder, cyclothymic disorder, obsessive compulsive disorder, eating disorder—NOS, anorexia nervosa, bulimia nervosa, panic disorder, generalized anxiety disorder, substance abuse induce mood disorder, fibromyalgia, chronic fatigue and immunodeficiency syndrome, fibromyalgia syndrome, myalgia, myositis, chronic fatigue unspecified, postviral fatigue syndrome, chronic fatigue syndrome NOS, benign myalgic encephalomyelitis, other fatigue, neoplastic (malignant) related fatigue, other malaise and fatigue, drug dependence—NOS, opiate dependence, benzodiazepine dependence, sedative (hypnotic or anxiolytic dependence), alcohol dependence, stimulant dependence, cocaine dependence, *cannabis* detoxification, opiate dependence (with withdrawal), benzodiazepine dependence (with withdrawal), sedative (hypnotic or anxiolytic dependence with withdrawal), alcohol dependence (with withdrawal), stimulant dependence (with withdrawal), cocaine dependence (with withdrawal), *cannabis* detoxification (with withdrawal), pain disorder—not otherwise specified (NOS), pain (unspecified), acute pain, body aches, buttock muscular pain, chronic back pain for greater than 3 months, chronic back pain greater than 3 months duration, chronic coccygeal pain for greater than 3 months, chronic low back pain, chronic low back pain for greater than 3 months, chronic low back pain greater than 3 months duration, chronic malignant pain, chronic neck pain, chronic nonmalignant pain, chronic pain, chronic pain due to malignancy, generalized aches and pains, generalized pain, neck pain (chronic), pain, pain crisis, pain in buttock, pain of coccyx greater than 3 months (chronic), neoplasm related pain (acute) (chronic), other chronic post-procedural pain, chronic pain due to bilateral total hip arthroplasty, chronic pain due to bilateral total knee arthroplasty, chronic pain due to left total hip arthroplasty, chronic pain due to left total knee replacement, chronic pain due to right total hip arthroplasty, chronic pain due to right total knee replacement, chronic pain following bilateral total hip arthroplasty, chronic pain following bilateral total knee arthroplasty, chronic pain following left total hip arthroplasty, chronic pain following left total knee arthroplasty, chronic pain following right total hip arthroplasty, chronic pain following right total knee arthroplasty, chronic pain due to bilateral partial hip arthroplasty, chronic pain due to bilateral partial knee arthroplasty, chronic pain due to left partial hip arthroplasty, chronic pain due to left partial knee replacement, chronic pain due to right partial hip arthroplasty, chronic pain due to right partial knee replacement, chronic pain following bilateral partial hip arthroplasty, chronic pain following bilateral partial knee arthroplasty, chronic pain following left partial hip arthroplasty, chronic pain following left partial knee arthroplasty, chronic pain following right partial hip arthroplasty, chronic pain following right partial knee arthroplasty, acute malignant pain, acute neck pain, acute nonmalignant pain, acute pain, acute pain due to malignancy, generalized aches and pains, generalized pain, neck pain (acute), pain, pain crisis, pain in buttock, pain of coccyx greater than 3 months (acute), neoplasm related pain (acute) (acute), other acute post-procedural pain, acute pain due to bilateral total hip arthroplasty, acute pain due to bilateral total knee arthroplasty, acute pain due to left total hip arthroplasty, acute pain due to left total knee replacement, acute pain due to right total hip arthroplasty, acute pain due to right total knee replacement, acute pain following bilateral total hip arthroplasty, acute pain following bilateral total knee arthroplasty, acute pain following left total hip arthroplasty, acute pain following left total knee arthroplasty, acute pain following right total hip arthroplasty, acute pain following right total knee arthroplasty, acute pain due to bilateral partial hip arthroplasty, acute pain due to bilateral partial knee arthroplasty, acute pain due to left partial hip arthroplasty, acute pain due to left partial knee replacement, acute pain due to right partial hip arthroplasty, acute pain due to right partial knee replacement, acute pain following bilateral partial hip arthroplasty, acute pain following bilateral partial knee arthroplasty, acute pain following left partial hip arthroplasty, acute pain following left partial knee arthroplasty, acute pain following right partial hip arthroplasty, acute pain following right partial knee arthroplasty, pain due to bilateral total hip arthroplasty, pain due to bilateral total knee arthroplasty, pain due to left total hip arthroplasty, pain due to left total knee replacement, pain due to right total hip arthroplasty, pain due to right total knee replacement, pain following bilateral total hip arthroplasty, pain following bilateral total knee arthroplasty, pain following left total hip arthroplasty, pain following left total knee arthroplasty, pain following right total hip arthroplasty, pain following right total knee arthroplasty, pain due to bilateral partial hip arthroplasty, pain due to bilateral partial knee arthroplasty, pain due to left partial hip arthroplasty, pain due to left partial knee replacement, pain due to right partial hip arthroplasty, pain due to right partial knee replacement, pain following bilateral partial hip arthroplasty, pain following bilateral partial knee arthroplasty, pain following left partial hip arthroplasty, pain following left partial knee arthroplasty, pain following right partial hip arthroplasty, pain following right partial knee arthroplasty, acute post-mastectomy pain, acute postoperative pain, acute pain due to trauma or injury, acute pain syndrome, acute pain associated with psychosocial dysfunction, psychosocial dysfunction due to acute pain, neoplasm related pain (acute) (acute), neoplasm related pain, pain due to neoplasm, pain due to neoplastic disease, causalgia (lower limb), causalgia (upper limb), central pain syndrome, acute pain syndrome, complex regional pain syndrome ii (lower limb), complex regional pain syndrome ii (upper limb), phantom limb syndrome with pain, phantom limb syndrome without pain, neoplasm related acute pain, chronic post-mastectomy pain, chronic postoperative pain, chronic pain due to trauma or injury, chronic pain syndrome, chronic pain associated with psychosocial dysfunction, psychosocial dysfunction due to chronic pain, neoplasm related pain (acute) (chronic), neoplasm related pain, pain due to neoplasm, pain due to neoplastic disease, causalgia (lower limb), causalgia (upper limb), central pain syndrome, chronic pain syndrome, complex regional pain syndrome ii (lower limb), complex regional pain syndrome ii (upper limb), phantom limb syndrome with pain, phantom limb syndrome without pain, neoplasm related chronic pain, reflex sympathetic dystrophy, hereditary and idiopathic neuropathy (unspecified), paraneoplastic neuromyopathy and neuropathy (synonyms follow), neuropathy (nerve damage) (paraneoplastic), neuropathy (nerve damage) (peripheral paraneoplastic), paraneoplastic neuropathy, paraneoplastic peripheral neuropathy, type 2 diabetes mellitus with diabetic neuropathy (unspecified), diabetes 2 with neurogenic erectile dysfunction, diabetes type 2 with peripheral neuropathy, diabetes type 2 with peripheral sensory neuropathy, diabetes type 2 with neuropathy, diabetic peripheral neuropathy associated with type 2 diabetes mellitus, diabetes mellitus 2 with neuropathic ulcer foot and heel, neurogenic erectile dysfunction due to type 2 diabetes mellitus, neuropathic midfoot and/or heel ulcer due to type 2 diabetes mellitus, neuropathy due to type 2 diabetes mellitus, peripheral neuropathy due to type 2 diabetes mellitus, peripheral sensory neuropathy due to type 2 diabetes mellitus, other specified diabetes mellitus with diabetic autonomic (poly)neuropathy, other chronic pain, postherpetic polyneuropathy, acute herpes zoster neuropathy, herpes zoster radiculitis, herpes zoster with nervous system complication, herpes zoster with nervous system complications, postherpetic neuralgia, postherpetic radiculopathy, postherpetic myelitis, postherpetic geniculate ganglionitis, postherpetic trigeminal neuralgia, diabetic neuropathy, neuropathy NOS, post-laminectomy syndrome, low back pain, post-surgical pain, endometriosis, migraine, hemiplegic migraine, migraine with aura (intractable), hemiplegic migraine (intractable), other migraine (intractable), migraine, unspecified (intractable), migraine headache NOS, migraine without aura (intractable), hemiplegic migraine (not intractable), other migraine (not intractable), migraine, unspecified (not intractable), hemiplegic migraine (intractable, without status migrainosus), migraine with aura, ophthalmoplegic migraine (not intractable), abdominal migraine (not intractable), migraine with aura (not intractable, with status migrainosus), migraine (unspecified, intractable, with status migrainosus), migraine without aura, migraine without aura (not intractable), migraine with aura (not intractable), chronic migraine without aura, migraine (unspecified, not intractable, without status migrainosus), migraine (unspecified, intractable without status migrainosus), other migraine (intractable, without status migrainosus), abdominal migraine (intractable; intractable allergic migraine; intractable ophthalmic migraine), other migraine (not intractable, without status migrainosus), menstrual migraine (intractable, without status migrainosus), Huntington's disease, Parkinson's disease, frontotemporal dementia, dementia, Alzheimer's disease, amyotrophic lateral sclerosis, spinal cord trauma, stroke, diffuse traumatic brain injury, HIV-associated dementia, epilepsy, suicidal ideation, Rett syndrome, dyskinesia, dystonia (unspecified), pseudobulbar affect, tinnitus (unspecified ear), glaucoma.

In some embodiments, formulations and methods disclosed herein are used to treat one or more fatigue and fatigue-related disorders. Examples of fatigue and fatigue-related disorders include fibromyalgia, fibromyalgia syndrome, chronic fatigue and immunodeficiency syndrome, myalgia, myositis, chronic fatigue (unspecified), postviral fatigue syndrome, chronic fatigue syndrome (NOS), benign myalgic encephalomyelitis, neoplastic (malignant) related fatigue, and other malaise and fatigue.

In some embodiments, formulations and methods disclosed herein are used to treat post-laminectomy syndrome (e.g., failed back syndrome). In some embodiments, formulations and methods disclosed herein are used to treat post-operative pain. In some embodiments, formulations and methods disclosed herein are used to treat cancer pain. In some embodiments, formulations and methods disclosed herein are used to treat osteoarthritis. In some embodiments, formulations and methods disclosed herein are used to treat fibromyalgia.

In some embodiments, formulations and methods disclosed herein are used to treat pain or a pain disorder. In some embodiments, chronic pain refers to pain having a duration of greater than 3 months. Examples of pain and pain disorders include pain that is not otherwise specified (NOS) such as acute pain, body aches, buttock muscular pain, lower back pain, chronic back pain, chronic coccygeal pain, chronic low back pain, chronic malignant pain, chronic neck pain, chronic nonmalignant pain, chronic pain, and generalized pain. In some embodiments, the pain can include pain crisis, pain in buttocks, pain of coccyx (chronic or acute), or neoplasm related pain (chronic or acute).

In some embodiments, the pain is chronic post-procedural and/or post-surgical pain. Examples of post-procedural pain include chronic pain due to bilateral total hip arthroplasty, chronic pain due to bilateral total knee arthroplasty, chronic pain due to left total hip arthroplasty, chronic pain due to left total knee replacement, chronic pain due to right total hip arthroplasty, chronic pain due to right total knee replacement, chronic pain following bilateral partial hip arthroplasty, chronic pain following bilateral partial knee arthroplasty, chronic pain following left partial hip arthroplasty, chronic pain following left partial knee arthroplasty, chronic pain following right partial hip arthroplasty, chronic pain following right partial knee arthroplasty, pain due to bilateral total hip arthroplasty, pain due to bilateral total knee arthroplasty, pain due to left total hip arthroplasty, pain due to left total knee replacement, pain due to right total hip arthroplasty, pain due to right total knee replacement, pain following bilateral partial hip arthroplasty, pain following bilateral partial knee arthroplasty, pain following left partial hip arthroplasty, pain following left partial knee arthroplasty, pain following right partial hip arthroplasty, pain following right partial knee arthroplasty, chronic post-mastectomy pain, chronic post-mastectomy pain, and chronic postoperative pain.

In some embodiments, the pain is chronic pain due to trauma or injury. In some embodiments, the pain is a chronic pain syndrome, also referred to as chronic pain associated with psychosocial dysfunction or psychosocial dysfunction due to chronic pain. In some embodiments, the pain is a neoplasm related pain or pain due to neoplastic disease (chronic or acute). In some embodiments, the pain is causalgia (lower limb and/or upper limb).

In some embodiments, the pain is central pain syndrome, complex regional pain syndrome I, complex regional pain syndrome II (lower limb), or complex regional pain syndrome II (upper limb).

In some embodiments, formulations and methods disclosed herein are used to treat disorders such as fibromyalgia, fibromyalgia syndrome, chronic fatigue and immunodeficiency syndrome, myalgia, myositis, chronic fatigue (unspecified), postviral fatigue syndrome, chronic fatigue syndrome (NOS), benign myalgic encephalomyelitis, phantom limb syndrome (with or without pain), reflex sympathetic dystrophy, hereditary and idiopathic neuropathy, and paraneoplastic neuromyopathy and neuropathy (including peripheral neuropathy), type 2 diabetes mellitus (with diabetic neuropathy, unspecified), or specified diabetes mellitus with diabetic autonomic (poly)neuropathy. Examples of type 2 diabetes mellitus with unspecified diabetic neuropathy include diabetes with neurogenic erectile dysfunction, peripheral neuropathy, peripheral sensory neuropathy, neuropathy, and neuropathic ulcer (e.g. foot and heel).

In some embodiments, formulations and methods disclosed herein are used to treat disorders such as postherpetic polyneuropathy, acute herpes zoster neuropathy, herpes zoster radiculitis, herpes zoster with nervous system complication, herpes zoster with nervous system complications, postherpetic neuralgia, postherpetic radiculopathy, postherpetic myelitis, postherpetic *geniculate* ganglionitis, or postherpetic trigeminal neuralgia.

In some embodiments, formulations and methods disclosed herein are used to treat disorders or conditions such as post-laminectomy syndrome and endometriosis (unspecified). In some embodiments, formulations and methods disclosed herein are used to treat migraines such as migraine with aura (intractable), migraine with aura (not intractable), hemiplegic migraine (intractable), migraine (unspecified, intractable), migraine headache (NOS), migraine without aura (intractable), migraine without aura (not intractable), migraine (unspecified, not intractable), hemiplegic migraine (intractable, without status migrainosus), other migraine (intractable), ophthalmoplegic migraine (not intractable), abdominal migraine (not intractable), abdominal migraine (intractable), intractable allergic migraine, intractable ophthalmic migraine, migraine with aura (not intractable, with status migrainosus), migraine (unspecified, not intractable, with status migrainosus), migraine (unspecified, intractable, with status migrainosus), chronic migraine without aura, migraine (unspecified, not intractable, without status migrainosus), migraine (unspecified, intractable, without status migrainosus), menstrual migraine (intractable, without status migrainosus), other migraine (intractable, without status migrainosus), and other migraine (not intractable, without status migrainosus).

In some embodiments, formulations and methods disclosed herein are used to treat a disease or condition such as tinnitus (unspecified ear) or glaucoma.

In some embodiments, formulations and methods disclosed herein are used to treat any combination of disorders or conditions described herein.

Treatment of Drug Dependence

In some embodiments, formulations and methods disclosed herein are used to treat drug dependence. Examples of drug dependence include opiate dependence, benzodiazepine dependence, sedative (hypnotic or anxiolytic) dependence, alcohol dependence, stimulant dependence, cocaine dependence, *cannabis* detoxification, opiate dependence (with withdrawal), benzodiazepine dependence (with withdrawal), sedative (with withdrawal) dependence, alcohol dependence (with withdrawal), stimulant dependence (with withdrawal), cocaine dependence (with withdrawal), and *cannabis* detoxification (with withdrawal).

In some embodiments, the methods disclosed herein comprise selecting or screening for an individual who has a drug dependence.

In some embodiments, the pharmaceutically acceptable salt comprises an acid. The pharmaceutically acceptable salt can comprise any of the acids described in the "Compositions" section.

In some embodiments, the compound of Formula (I) is administered as a pharmaceutical composition further comprising a complexing agent. The complexing agent can comprise any of the complexing agents described in the "Compositions" section in any amount specified in the "Compositions" section, such as any of the cyclodextrins provided herein. The pharmaceutical composition can also comprise any of the additional components provided herein in the "Compositions" section, including without limitation bases, buffers, co-solvents, preservatives, surface-active agents, surfactants, solubilizing agents, stabilisation agents, antioxidants, cryoprotectants, lyoprotectants, bulking agents, tonicity-adjusting agents, antimicrobial agents, diluents, soothing agents, and/or emulsion stabilizers.

In some embodiments, the compound of Formula (I) is a pharmaceutically acceptable salt having structural Formula (I-A):

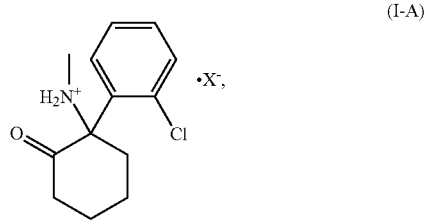 [SMILES: C[NH2+]C1(c2ccccc2Cl)CCCCC1=O]

(I-A)

or an enantiomer, a mixture of enantiomers, or an isotopic variant thereof; or solvate or hydrate thereof, wherein: $X^-$ is a counter ion, and further wherein the compound of Formula (I-A). $X^-$ may be any of the counter ions provided herein in the "Compositions" section.

In some embodiments, the pharmaceutical composition is a solution. In some embodiments, the pharmaceutical composition is a solid. In some embodiments, the pharmaceutical composition has a pH>about 4, for example a pH from about 4 to about 7, or any of the pH values provided in the "Compositions" section. The pharmaceutical composition may also comprise any of the properties as specified in the "Compositions" section, including without limitation osmolality values (e.g. from about 250 mOsm/kg to about 850 mOsm/kg) and/or concentrations of ketamine (e.g. from about 20 mg/mL to about 250 mg/mL).

The pharmaceutical compositions can be administered on a regimen of one (1) to four (4) times per day, including once, twice, three times, and four times per day. In some embodiments, the compound of Formula (I), or an enantiomer, a mixture of enantiomers, or an isotopic variant thereof; or a pharmaceutically acceptable salt, solvate or hydrate thereof is administered once per day.

In some embodiments, the compound of Formula (I), or an enantiomer, a mixture of enantiomers, or an isotopic variant thereof; or a pharmaceutically acceptable salt, solvate or hydrate thereof, is administered in a dose of from about 20 mg/mL to about 150 mg/mL. In some embodiments, the compound of Formula (I), or an enantiomer, a mixture of enantiomers, or an isotopic variant thereof; or a pharmaceutically acceptable salt, solvate or hydrate thereof, is administered in a dose of about 100 mg/mL. In some embodiments, the compound of Formula (I), or a pharmaceutically acceptable salt thereof, is administered in a dose of about 128 mg/mL.

In some embodiments, the compound of Formula (I), or an enantiomer, a mixture of enantiomers, or an isotopic variant thereof; or a pharmaceutically acceptable salt, solvate or hydrate thereof, is administered daily. In some embodiments, the compound of Formula (I), or an enantiomer, a mixture of enantiomers, or an isotopic variant thereof; or a pharmaceutically acceptable salt, solvate or hydrate thereof, is administered once daily.

In some embodiments, the compound of Formula (I), or an enantiomer, a mixture of enantiomers, or an isotopic variant thereof; or a pharmaceutically acceptable salt, solvate or hydrate thereof, is administered subcutaneously by injection (e.g., bolus or infusion) or by an implantable mini-pump. In some embodiments, the compound of Formula (I), or an enantiomer, a mixture of enantiomers, or an isotopic variant thereof; or a pharmaceutically acceptable salt, solvate or hydrate thereof, is administered by an implantable mini-pump. In some embodiments, the implantable mini-pump is a 6-month pump. In some embodiments, a single implantable mini-pump is used.

In some embodiments, the compound of Formula (I), or an enantiomer, a mixture of enantiomers, or an isotopic variant thereof; or a pharmaceutically acceptable salt, solvate or hydrate thereof, is administered by subcutaneous injection. In some embodiments, the compound of Formula (I), or an enantiomer, a mixture of enantiomers, or an isotopic variant thereof; or a pharmaceutically acceptable salt, solvate or hydrate thereof, is injected approximately once monthly. In some embodiments, the compound of Formula (I), or an enantiomer, a mixture of enantiomers, or an isotopic variant thereof; or a pharmaceutically acceptable salt, solvate or hydrate thereof, for a period of up to about 6 months. In some embodiments, the compound of Formula (I), or an enantiomer, a mixture of enantiomers, or an isotopic variant thereof; or a pharmaceutically acceptable salt, solvate or hydrate thereof, is injected approximately once weekly. In some embodiments, the compound of Formula (I), or an enantiomer, a mixture of enantiomers, or an isotopic variant thereof; or a pharmaceutically acceptable salt, solvate or hydrate thereof, is injected approximately once weekly for a period of up to about 25 weeks or more.

IV. Methods of Formulating Ketamine

In one aspect, provided herein, is a method of preparing a pharmaceutical composition, comprising: mixing a free acid form of a complexing agent comprising at least one acidic functional group and a compound of structural Formula (I):

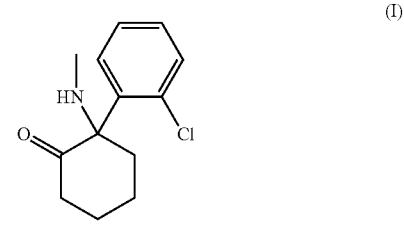 [SMILES: CNC1(c2ccccc2Cl)CCCCC1=O]

(I)

or an enantiomer, a mixture of enantiomers, or an isotopic variant thereof; or a solvate or hydrate thereof; wherein the compound of structural Formula (I) is in its freebase form.

In some embodiments, the mixing occurs in a suitable medium. In some embodiments, the suitable medium is an aqueous medium. In some embodiments, the suitable medium is an organic solvent. In some embodiments, the mixing occurs in a solution. In some embodiments, the mixing occurs when the complexing agent and the compound of structural Formula (I) are in powder form.

In some embodiments, the mixing occurs by portion-wise addition of one of the reagents. In some embodiments, the compound of structural Formula (I) is added portion wise to a solution comprising the complexing agent.

In some embodiments, the pharmaceutical composition is in a form for dosing or administration by subcutaneous injection.

In some embodiments, the complexing agent comprising at least one acidic functional group is a cyclodextrin. Any of the cyclodextrins provided in the "Compositions" section can be used. The cyclodextrin or other complexing agent may also be added at any amount provided in the "Compositions" section or at any molar ratio provided therein, including ratios of acidic functional groups to the compound of Formula (I).

In some embodiments, the method further comprises adjusting the pH of the pharmaceutical composition. In some embodiments, only a minimal adjustment of the pH is necessary. In some embodiments, the pH is adjusted with a strong base. In some embodiments, the pH is adjusted with sodium hydroxide, potassium hydroxide, barium hydroxide, cesium hydroxide, strontium hydroxide magnesium hydroxide, calcium hydroxide, lithium hydroxide, or rubidium hydroxide. In some embodiments, the pH is adjusted with sodium hydroxide. In some embodiments, the pH is adjusted to a desired pH. In some embodiments, the desired pH is any of the pH values provided herein in the "Compositions" section.

In some embodiments, the pharmaceutical composition has a pH>about 4. The pH of the pharmaceutical composition can be any of the pH values provided in the "Compositions" section, such as a pH from about 4 to about 7, or any other of the pH values or ranges provided therein.

In some embodiments, the method further comprises adding a preservative to the composition. The preservative may be added to the composition at any time or in any order. In some embodiments, the preservative is added after the complexing agent and compound of structural Formula (I) have been added. In some embodiments, the preservative is added prior to adding the compound of structural Formula (I). In some embodiments, the preservative is benzethonium chloride. The preservative may also be any of the preservatives provided in the "Compositions" section and may be added at any concentration provided therein.

In some embodiments, the method further comprises adding a base, a buffer, an emulsifying agent, a surfactant, a solubilizing agent, an emulsifying agent, a co-solvent, or any combination thereof. The method may also further comprise adding any of the additional components provided herein in the "Compositions" section, including without limitation bases, buffers, co-solvents, preservatives, surface-active agents, surfactants, solubilizing agents, stabilisation agents, antioxidants, cryoprotectants, lyoprotectants, bulking agents, tonicity-adjusting agents, antimicrobial agents, diluents, soothing agents, and/or emulsion stabilisers.

In some embodiments, the method further comprises adjusting the osmolality of the pharmaceutical composition. In some embodiments, the adjusting the osmolality of the pharmaceutical comprises diluting the pharmaceutical composition. Diluting the pharmaceutical composition may comprise diluting with water or other physiologically acceptable buffer, such as phosphate buffered saline, or any of the buffers provided in the "Compositions" section. In some embodiments, adjusting the osmolality of the pharmaceutical composition comprises adding a tonicity modifying agent. The tonicity modifying reagent may be any pharmaceutically acceptable reagent, such as sodium chloride, or any of the reagents provided in the "Compositions" section. In some embodiments, there is no need to adjust the osmolality of the pharmaceutical composition after mixing the compound of structural Formula (I) and the complexing agent.

The final osmolality of the pharmaceutical composition may be any of the osmolalities provided in the "Compositions" section, such an osmolality from about 250 mOsm/kg to about 850 mOsm/kg, or any other range or value provided therein.

The final concentration of the compound of structural Formula (I) of the pharmaceutical composition may be any of the concentrations provided in the "Compositions" section, including values over 20 mg/mL or any of the other values or ranges provided therein.

Also provided herein are methods of generating the free acid form of complexing agents comprising at least one acidic functional group. In some cases, complexing agents comprising acidic functional groups are commercially available only as salts of the complexing agents, such as sodium salts. For example, SBEBCD is sold commercially as the sodium salt.

The free acid form of such complexing agents can be generated by any number of methods. For example, the salts of complexing agents comprising acidic functional groups can be bound to a suitable acidic cation exchange resin (e.g. Amberlite® IR120 Hydrogen form resin, available from commercial vendors such as Sigma Aldrich) and then eluted to yield the desired free acid form of the complexing agent. An additional method potentially suitable for this purpose could involve treating the sodium salt of the complexing agent (e.g. SBEBCD) with a hydrochloric acid or other suitable acid in a suitable organic solvent. Ideally, the organic solvent is selected such the resulting sodium chloride will precipitate out of solution and leave the complexing agent free acid in solution. The sodium chloride salt could then be removed by filtration, and the filtrate could then be concentrated or the solvent removed to yield the free acid. Conversely, the filtrate could be solvent exchanged with water for injection using standard azeotropic distillation under vacuum. Alternatively, the filtrate could be used to prepare the formulation as is and removed at a later stage.

EXAMPLES

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

Example 1. Subcutaneous Formulations of Ketamine

Up until recently, the current standard of care for treating psychiatric disorders with ketamine HCl typically involves in-office use with intravenous delivery being the most common delivery method. Intravenous delivery can require significant monitoring efforts, IV placement, and various other mechanical requirements of IV procedure (e.g., normal saline, sedatives such as midazolam or propofol, hospital bed or IV chair). Some practitioners deliver ketamine in the office through intramuscular delivery, which generally requires reduced medical paraphernalia (e.g., no IV, saline bags, cannulas, etc., needed). Depending upon the procedural protocol and practice patterns of a given practitioner, usually in this situation there is reduced monitoring as well, often consisting only of intermittent blood pressure and pulse, and/or pulse oximetry. Alternatively, ketamine is sometimes administered outside the office or clinic in the form of sub-lingual, compounded "troches," oral compounded capsules, and intra-nasal compounded spray. Recently, an intranasal formulation of the S enantiomer of ketamine was approved for adjunctive treatment of major depression as is to be used in-office only due to substantial acute dissociative side effects associated with this bolus approach to ketamine delivery. Each of these four modes of ketamine delivery has various drawbacks that can limit their use depending upon the clinical parameters of a given medical case. Intravenous delivery of ketamine can readily achieve steady state blood levels that can be maintained for as long as desired. This pharmacokinetic capacity can be highly advantageous in certain treatments; however, this mode of delivery can only be achieved in the hospital, clinic or home hospice style setting, severely limiting access to ketamine delivered in a non-bolus manner. Because bolus dosing of ketamine is associated with substantial motor impairment and dissociative side effects, intravenous (IV) dosing provides a significant advantage by providing control over dosing and the capacity to achieve a steady state blood level that is within acceptable side effect parameters. And because 100% of the ketamine is bioavailable with IV administration there is minimal exposure to excess metabolites that are not producing clinical benefit, but that instead increase risk to non-target tissues, like the bladder (e.g., ketamine cystitis). However, despite all of the advantages to IV delivery in ketamine procedures and treatments, this mode of treatment is only available in the hospital and clinic, creates a substantial amount of medical waste, is costly, requires a meaningful time commitment for patients and healthcare providers alike, and is sometimes limited by compromised venous access. Intramuscular (IM) delivery has the same advantages with regard to bioavailability and reduced exposure to metabolites, and is more convenient than IV, but represents a bolus delivery method predominately and, as such, side effects are harder to manage while delivering sufficient doses to achieve a desired benefit. Off-label oral, sublingual and intranasal delivery mechanisms currently used in clinical practice provide the advantage of allowing relatively safe use in the home setting but are limited by their being solely a bolus delivery method and by the necessity of increased dosing in milligrams due to low bioavailability; this increases exposure to clinically irrelevant metabolites that increase exposure to risk. Oral dosing of ketamine to reach equivalence to a short IV or IM treatment increases exposure to undesirable inflammatory metabolites by up to 9-fold; sublingual routes of administration (ROA) produce 3-fold increases and the intranasal route of administration produces 2 to 4-fold increases. A subcutaneous formulation of ketamine for delivery by a pump device would have advantages that clearly distinguish it from all of the different forms of ketamine delivery, while simultaneously reducing attendant disadvantages of these other ROAs (Table 1). For example, such a product would be capable of achieving a plasma steady state of ketamine capable of treating certain identified symptoms, but that is low enough to mitigate or reduce unwanted side effects. In addition, small bolus options could be made available that would offer the advantages that may occur clinically with stronger pulse on/pulse off bolus dosing of ketamine in clinical care. In addition, bioavailability would be closer to that of IV and IM routes of administration, reducing patient exposure to undesirable, risky and/or non-clinically relevant metabolites.

TABLE 1

| Route of Administration | Intravenous | Intramuscular | Subcutaneous | Oral | Intranasal | Sublingual |
| --- | --- | --- | --- | --- | --- | --- |
| Dosing Strategies Achievable | Steady State & Bolus | Bolus only | Steady State & Bolus | Bolus only | Bolus only | Bolus only |
| Potential Tx Settings | Hospital Clinic | Hospital Clinic | Hospital Clinic Home | Clinic Home | Clinic Home | Clinic Home |
| Bioavailability | Highest 100% | High 93% | High >90% | Very Low 11-20% | Low 25-50% | Low 29% |
| Metabolite Exposure | Low | Low | Low | Very High | High | High |
| Procedural Burden | High | Moderate | Low to Moderate | Low | Moderate | Moderate |
| Side Effects | Moderate | High | Low | Moderate | High | Moderate |
| Consistency in Treatment | High | Moderate | High | Low | Low | Low |
| Regulatory Status (for Pain Dx) | Quasi On-Label USP | Quasi On-Label USP | Development in progress | Off-Label/ Compound Only | Off-Label/ Compound Only | Off-Label/ Compound Only |

The systems and methods disclosed herein provide an innovative solution to the problems with routes of ketamine administration as detailed above by providing a new subcutaneous formulation the solves the problems that have made this route of administration of ketamine non-relevant in current clinical care. It is understood that subcutaneous delivery of currently available forms of ketamine is exceedingly rare, either by bolus injection or infusion pump, due to its well characterized irritant effect to subcutaneous and/or dermal tissues. Subcutaneous ketamine has been reported to cause irritation to subcutaneous tissues and even sterile abscess, and is generally considered a painful route of administration and is thus avoided. This irritant effect is likely to occur through one or more of three basic properties of current ketamine formulations: 1) acidic pH ranging on USP label from 3.5-5.5, but in reality, averaging somewhere around 3.5-4.0; 2) hypertonicity and/or hyperosmolality and/or hyperosmolarity resulting from the ketamine in solution and the sodium chloride salt produced in standard manufacturing processes used to create an ionized form of ketamine for solution; 3) a direct effect of the ketamine itself.

A formulation that reduces the potential contribution of the first and/or the second and/or the third factors is expected to reduce irritation to tissue and increase tissue and/or sensory tolerance to this route of administration. Formulation innovations described herein are designed to produce a stable ketamine formulation with a pH closer to that of human subcutaneous tissues and/or with reduced tonicity and/or osmolality and/or osmolarity, to be achieved through one or many production processes described herein. In general, a number of features to reduce injection site irritation/pain with SC and IM injections may include reducing injection volume, and/or reducing hypertonicity and/or hyperosmolality and/or hyperosmolarity, and/or reducing injection speed, and/or adjustment of solution towards physiologic pH. Any of these factors might be included in one or all of the formulations described herein. Reduced injection speed can in some cases reduce pain and irritation.

Reducing injection volume may increase tolerance to SC injection, and tonicity can also affect tissue tolerance. These factors also combine together to influence injection site irritation and pain. Thus, any strategies to reduce injection site pain and irritation with SC or IM injections combining one or more of these factors might consider the influence of one or all of these factors Accordingly, one advantage provided by the formulations and methods disclosed herein can include providing at-home delivery of drug formulations such as ketamine, optionally by subcutaneous delivery. Subcutaneous drug administration bypasses various problems with traditional at-home treatments such as oral capsules and nasal sprays. Oral or nasal delivery tends to require higher dosages than intramuscular or subcutaneous delivery to achieve comparable clinical effects, which carries a risk for bladder dysfunction due to the higher dosing. Oral or sublingual administration is often unreliable due to the presence of food or chyme in the stomach or proximal small intestines and substantial first pass metabolism. Intranasal administration can present allergic or irritation rhinitis, epistaxis (nosebleeds), or bacterial or viral sinusitis. Moreover, some patients are unable to make regular clinic visits to receive treatment. The opportunity and direct costs associated with repeated in-office ketamine treatments, and post treatment monitoring pose a significant barrier to effective treatment. This is especially true in large urban centers where it can be particularly difficult for patients to arrange for the time needed to travel to treatment centers. The potential for increased utilisation of effective at-home treatment with ketamine would notably reduce this barrier to treatment for patients that suffer from depression, pain, or other appropriate conditions that might benefit from ketamine treatment throughout the country. Patients would not need to make clinic visits with the frequency required by current standard of care if they have access to effective at-home delivery systems and methods. Such convenience can save time and money for the patient as well as money for the reimbursing entity. Therefore, the formulations and methods disclosed herein can combine the advantages of subcutaneous delivery with the convenience and cost effectiveness of at-home treatment.

Another advantage provided by the formulations and methods disclosed herein are treatment regimens that provide effective treatment while reducing the risk of side effect(s) and/or dissociative symptom(s) associated with standard of care treatments. Such treatment regimens can provide more frequent administration of smaller doses and/or one or more sustained doses, which mitigates the effects that often arise from administration of a large bolus. For example, delivering at a sustained lower dose and/or a lower infusion rate can mitigate much of the uncomfortable psychological or dissociative side effects, and reduces or eliminates the recovery time required for a patient to re-engage their lives in comparison to IV or IM injections performed at the clinic. Moreover, the at-home dosage regimen disclosed herein can provide effective steady state plasma concentrations outside of the clinic setting, which is unfeasible under current standard of care at home for certain active ingredients such as ketamine due to its short half-life and substantial first pass metabolism.

Another advantage provided by the formulations and methods disclosed herein is administration of one or more doses of a drug such as ketamine according to a programmed dosage regimen. Such devices allow drug administration in the traditional hospital or clinic setting, but also provide the option to self-administer at home or outside the hospital/clinic setting. A doctor or healthcare provider can program a delivery device with a dosage regimen, and the patient or subject is able to use the device to self-administer one or more doses at home. The subject is thus given limited control to implement the pre-programmed dosage regimen. The use of the pre-programmed dosage regimen to self-medicate outside of the clinic allows accurate titration of blood levels with minimally effective doses of an active ingredient such as ketamine. This can decrease the procedural burden and medical equipment required during treatment in the clinic or hospital preformed through the current art consisting of IV infusion or IM bolus injection. Another benefit can be a reduction in same-day and next-days side effects that are associated with current in-office and at-home treatment such as dissociation, disorientation, confusion, drowsiness, brain fog and physical fatigue. Moreover, the dosage regimen can be programmed to control the rate of drug delivery to mitigate certain side effects such as, for example, adverse cardiac events known to be associated with ketamine usage. In some cases, the dosage regimen is programmed for sustained release and/or extended release dosing of a drug such as ketamine.

Another advantage provided by the formulations and methods disclosed herein can include the prevention of administration of a bolus of a drug such as ketamine beyond a dosage limit. Administration of a large bolus of a drug such as ketamine can invoke effects such as dissociation, disorientation, confusion, drowsiness, increased heart rate, elevated blood pressure, euphoria, and even temporary paralysis. Limiting the maximum dosage of a drug prevents the subject from exceeding the limits of a set dosing regimen, abusing the drug, or overdosing.

Another advantage provided by the formulations and methods disclosed herein is tamper resistant drug delivery that prevents unauthorized access to the drug stored within the device and/or a drug cartridge. Drugs such as ketamine can be subject to abuse, and delivery mechanisms that cede control to the patient are accompanied by the risk of abuse and/or addiction. Tamper resistant devices and/or drug cartridges help prevent unauthorized access to the drug formulation contained within, thereby limiting use of the drug to authorized uses such as according to a pre-programmed dosage regimen.

Example 2. Testing the Formulations Disclosed Herein

1. The formulations provided herein, in comparison to standard ketamine, are tested to determine an association with reduced subjective experience of erythema and/or pain and/or itching and/or burning and/or stinging and/or irritation and/or other measured parameters signifying a noxious effect to the administered tissues in acute and/or chronic testing in animals and/or humans will be demonstrated. Animal data could be obtained by treating two cohorts of animals, one treated subcutaneously by our formulation of ketamine, and another treated subcutaneously by currently available ketamine HCl. Animal technicians would observe and document signs of irritation and/or erythema in the local site dermal tissue. Local site irritation and erythema are accurate markers of tissue damage and generally also associated with increased pain.
2. The formulations provided herein, in comparison to standard ketamine, are tested to determine an association with reduced histological changes and/or signs of tissue damage and/or denigration and/or desiccation and/or inflammation in in-vitro and/or in-vivo human and/or animal tissues will be demonstrated. Histology data could be obtained by observing dermal tissue samples collected from two cohorts of animals, one treated subcutaneously by our formulation of ketamine, and another treated subcutaneously by currently available ketamine HCl. Biopsy specimens from each cohort would undergo fixation, processing and staining before observation by a trained histotechnologist.
3. The formulations provided herein are tested to determine that the formulation successfully holds in solution and/or complexes and/or solubilizes and/or emulsifies any or all of the non-ionized ketamine that is present at the higher pH than standard ketamine formulations will be demonstrated. Non-ionized ketamine solubility curves in the presence of a complexing agent possibly to include any of the described agents in this document and/or potentially to include a sulfobutylether-β-cyclodextrin (e.g., Captisol®) or a hydroxypropyl-β-cyclodextrin (e.g., Cavasol®) is predicted to establish the percentage of ketamine in a non-ionized state that is successfully held in solution at a given target pH, the achievement of which would be impossible without said complexing agent.
4. The formulations of ketamine provided herein are tested to determine that the concentration of ketamine that can be maintained in solution.
5. The formulations of ketamine provided herein are tested to demonstrate performance with fidelity across delivery parameters identified in the pump chosen for formulation delivery in comparison to the performance of this same pump delivering medication for which it was initially FDA approved (potentially to include standard insulin or another medication or a compound or a "biologic" medication, or a molecule or a solution).
6. The formulations provided herein, in comparison to standard of care, are tested to determine their association with comparably reduced subjective and/or objective signs or symptoms of chronic and/or acute pain and/or other identified clinical symptoms such as those associated with major depression, post-traumatic stress disorder, dysthymia, anxiety, withdrawal, and/or other psychiatric conditions as described herein.
7. The formulations provided herein, in comparison to placebo, are tested to determine their association with increased reductions in subjective and/or objective signs or symptoms of acute and/or chronic pain and/or other identified clinical symptoms such as those associated with major depression, post-traumatic stress dysthymia, anxiety, withdrawal, and/or other psychiatric conditions as described herein in comparison to placebo. For pain management this data could result from stimulated pain studies in animals potentially using but not limited to models such as tail flick assessment, Randall Selitto or abdominal spasm. These studies could compare two cohorts of animals and their response to pain stimuli pre-dose and after administration of either our ketamine formulation or placebo. It is predicted animals treated with the formulations disclosed herein will show reduced signs of central acting and/or peripherally acting and/or hyperalgesic and/or other types of pain compared to placebo.
8. The formulations provided herein, in comparison to standard ketamine, are tested to determine that they are more stable and effective at maintaining all ketamine in solution at a higher pH than currently available ketamine HCl at a comparable concentration that is titrated to a comparable pH.
9. Formulations provided herein are tested to show reduction in osmolality and/or osmolarity and/or tonicity in comparison to currently available ketamine HCl formulations at comparable or even lesser concentrations (e.g. 50 mg/mL). In some formulations, it is predicted to that data will be provided demonstrating the formulations are successful in reducing osmolality and/or osmolarity and/or tonicity based on formulation techniques to avoid or remove unnecessary ions as described herein. In some formulations described herein, it is predicted that, in comparison to standard formulations of ketamine HCl, the formulations are successful in reducing osmolality and/or osmolarity and/or tonicity using an excipient solubilizing and/or complexing agent such as a substituted cyclodextrin that has been converted to an acid to achieve three effects, namely 1) titration to desired pH, 2) solubilizing the portion of non-ionized ketamine present at a higher pH, and 3) removing unnecessary sodium groups that would add unwanted osmoles. In some formulations described herein, it is predicted that, in comparison to standard formulations of ketamine at higher pH using a standard unaltered excipient solubilizing and/or complexing agent such as a substituted cyclodextrin, the formulations are successful in reducing osmolality and/or osmolarity and/or tonicity using an excipient solubilizing and/or complexing agent such as a substituted cyclodextrin that has been converted to an acid to achieve three effects, namely 1) titration to desired pH, 2) solubilizing the portion of non-ionized ketamine present at a higher pH, and 3) removing unnecessary sodium groups that would add unwanted osmoles.
10. Formulations provided herein utilizing novel salts of ketamine (e.g., ketamine-SBE-β-CD, ketamine fumarate, ketamine malate) are tested to show reduction in osmolality and/or osmolarity and/or tonicity, in comparison to a similar formulation using standard ketamine HCl salt.
11. The formulations provided herein are tested to determine if they successfully complex and/or solubilize and/or emulsify any non-ionized ketamine that is present at a pH higher than the pKa of ketamine and/or higher than that of standard USP ketamine formulations. It is important to note that despite the USP label for ketamine stating that ketamine pH falls between 3.5-5.5, initial experiments have shown that the actual average pH of ketamine falls within a narrower range and at the lower end of this pH spectrum (e.g., 3.93) formed from powdered ketamine HCl and 3.74 measured in USP bottles of ketamine 100 mg/mL). Standard ketamine is formulated to be at a pH that produces full ionization of ketamine and therefor full solubility without any excipient emulsifying agents, complexing agents, surfactant agents or solubilizing agents. Thus, it is predicted that data will be provided demonstrating that a stable ketamine solution formulation has been developed as proposed that achieves an average pH that is at least 0.5 pH point higher (likely to be at least 1 pH point higher) than the average found in current standardized USP formulations of ketamine of comparable strength.

12. Solubilizing agents will be tested to characterize ketamine solubility curves within different concentrations of solubilizing agents potentially including but not limited to sulfobutyl-ether-beta-cyclodextrin (e.g., Captisol®), hydroxypropyl-beta-cyclodextrin or other cyclodextrin entities will be provided.

Example 3. Formulation Information and Description (Components, Percentages, pH, Salt Content, Etc.)

Description of Innovation/Novel Features:

Ketamine Hydrochloride is currently on label only for IV and IM delivery. Off-label use of approved formulations is somewhat common, and compounding pharmacies are known to prepare SL, oral, per-rectal, transdermal and intranasal formulas. The formulation provided herein will be delivered in subcutaneous fashion with a personal pump device and will result from the following innovations:

1. New Subcutaneous Route of Delivery: Currently ketamine Hydrochloride is only dosed IM or IV. A device-medication combo that would be for subcutaneous delivery specifically is being developed.
2. pH Adjustment and Buffering: The solution pH will be raised at least 0.5 pH points above the average pH found in currently available USP ketamine products to increase comfort and tissue tolerance.
3. Strength Attunement: The target solution concentration of ketamine is from about 20 mg/mL to about 150 mg/mL, or more preferably from about 50 mg/mL to about 120 mg/mL or greater, however, solution concentration is likely to be tuned to the subcutaneous pump mechanics per the findings of research. Currently, ketamine hydrochloride is available at 10, 50 and 100 mg/mL. However, depending upon pump mechanics in relation to proposed ketamine formulation (e.g. pump/formulation validity testing), clinical response findings in animal or human studies, side effects findings, adverse event findings, and/or other data discovery of final formulation strength may fall from about 20 mg/ml to about 150 mg/ml.
4. Complexing Ketamine Free Base: Addition of a complexing agent potentially to include sulfobutyl-ether-beta-cyclodextrin (e.g., Captisol®), hydroxypropyl-beta-cyclodextrin, or another cyclodextrin to solubilize non-ionized portion of ketamine in order to maintain a ketamine solution concentration at a therapeutically relevant level and potentially improve tissue tolerance through subcutaneous delivery. Alternative approaches that include emulsifying agents and/or buffers may also be included to achieve this end.
5. Possible use of divalent or trivalent salts to form novel ketamine solutions with reduced osmolality: By using a ketamine solution formed from a ketamine salt consisting of ketamine combined with a trivalent anion to form a ketamine salt, potentially to include but not limited to citrate, and phosphate, or a divalent anion potentially to include but not limited to sulfate, carboxylate, tartrate, glutarate, succinate, maleate, and malonate, or other multivalent anions such as variously substituted anionic cyclodextrins including carboxymethyl-β-CD, succinyl-2-carboxyethyl-β-CD, β-CD-phosphate, beta-β-sulfate, sulfoethyl-β-CD, and SBE-β-CD, we will be able to further reduce the osmolality of the final product in line with our goal to increase subcutaneous tissue tolerance.
6. Use of s-ketamine enantiomer: This is another potential innovation that has purpose in increasing total active ketamine that can be delivered given existing pump mechanics that are limited to small drug volumes.

Current Proposed Label (Subject to Confirmation after Testing and Finalization):

Ketamine Hydrochloride for Subcutaneous Injection
CIII
Rx Only
pH 4.5 to 6.5
Strength: potential range 20-150 mg/mL
  Ingredients:
  Ketamine potential range 20-150 mg/ml)
  Captisol® (a cyclodextrin) potential range 50 to 600 mg/mL
  Benzethonium Chloride potential range 0.1-0.5 mg/mL
  Buffer (TBD)
  Store at 20° to 25° C. (Controlled Room Temperature) or at 2° to 8° C. (Refrigerated) dependent on further testing Example 4A. Potential Example of Initial Formulation Protocol (to be More Closely Determined after Further Development)

Dissolve ketamine HCl, benzethonium chloride, HP-beta-CD and potential buffer (TBD) in sterile water. Dilute with water to 90% of final target volume. Adjust the pH to the target range with aqueous NaOH prepared in sterile water. Adjust to the final volume by the addition of sterile water.

1) Initial Testing:
   a. Solubility: Determine the solubility of unionized ketamine at different SBE-β-CD concentrations: The solubility of SBE-β-CD is reported as 0.6 g/mL. Between 200 to 600 mg/mL of this cyclodextrin should complex the unionized portion of ketamine in solution at a potential total ketamine concentration range of 20 to 150 mg/ml, and at a potential pH range from 4.5 to 6.5. The actual pH of the final solution and concentrations of SBE-β-CD, ketamine, preservative and added buffer(s) necessary to achieve formulation goals is to be determined.
   b. Stability Testing: Solutions made in this initial phase should be stored at controlled room temperate for one month and three months to determine initial stability by Appearance, pH, osmolality and ketamine and SBE-β-CD (e.g., Captisol®) concentrations.
      i. Short Term
         1. Validation of concentration with HPLC or other means
         2. pH
         3. Osmolality
         4. Appearance (precipitation of ketamine)
         5. Also determine ICH compliant stress testing results (light, heat, pH, etc.)
      ii. Long Term (≥6 months)
         1. Stability in Temperature Cycling (freeze/thaw cycles)
         2. Anti-Microbial Properties/Susceptibility to Contamination.

3. Short and Longer-term Stability in Cyclic Olefin Polymer capsules, device cartridges and USP glass
3) Buffers
   a. It is believed that ketamine has potential to act as a buffer at pH slightly higher than its pKa and/or higher than standard USP formulations. If this is the case a secondary buffer may not be necessary for pH stability, however, a buffer may be needed to maintain pH stability.
   b. Only non-irritating buffers will likely be considered, including phosphates and histidine.
4) Emulsifiers
   a. SBE-β-CD (e.g., Captisol®)—This is the first choice given that it is an industry standard, substantial safety data already exists, and the parent company can provide support.
   b. Other possibilities:
      i. Hydroxypropyl-beta-cyclodextrin/HP-beta-CD or
      ii. Polysorbate/Tween 20 or Tween 80
      iii. Glycerin
      iv. Propylene glycol
      v. Complexing/emulsifying agent
5) Treatment Model: While the details may change with new data, and with Phase I and Phase II research, the current treatment model for subcutaneous delivery of ketamine by patch pump (with both basal rate and bolus dosing) is as follows. Treatment advised to occur for 24 to 72 hours (e.g., up to three, 24-hour patch pumps in sequence) before patient is advised to rest for at least one, and up to three days off before using again. No more than 10 treatments per month are advised.

Instructions:
   1. Clean skin in preparation.
   2. Remove adhesive backing. Place patch on skin.
   3. Remove safety nib. Insert catheter with a firm press downward. This action starts the basal rate of ketamine delivery as per the pump specifications.
   4. For acute or breakthrough pain, press the bolus button. You can use this bolus feature up to 18 times throughout a 24-hour period. Each bolus activation will deliver 2.5 mg of ketamine.
6) Projected Dosing Ranges for clinical use: Three pump strengths are available. See Tables below for current projections on basal, bolus and total dosing of both ketamine and Captisol® for the three different strength pumps currently planned, however final concentrations will be determined after formulation development. Two different tables are provided to illustrate the differences in dosing ranges for potential differences in concentration of ketamine and/or Captisol®. Ketamine formulations are presented in Tables 2A-2C. Captisol® is included in some formulations as a complexing agent.

TABLE 2A

Ketamine Formulations
Examples of potential target ketamine concentrations attuned to an infusion pump

| Pump Strength | Basal Rate: ml/hr | Ketamine: New Conc. mg/ml | Basal Total: mg/24 hr | Basal Dose: mg/kg/ 24 (175 lb) | Bolus Total: mg/24 hr | Bolus Dose: mg/kg/ 24 (175 lb) | Total Ketamine: mg/24 hr | Total Ketamine: mg/kg/ 24 hr (175 lb) |
|---|---|---|---|---|---|---|---|---|
| LOW | 0.0083 | 80.0 | 15.9 | 0.200 | 28.8 | 0.362 | 44.7 | 0.56 |
| MED | 0.0125 | | 24.0 | 0.302 | 28.8 | 0.362 | 52.8 | 0.66 |
| HIGH | 0.0167 | | 32.1 | 0.403 | 28.8 | 0.362 | 60.9 | 0.77 |
| LOW | 0.0083 | 85.00 | 16.9 | 0.213 | 30.6 | 0.385 | 47.5 | 0.60 |
| MED | 0.0125 | | 25.5 | 0.321 | 30.6 | 0.385 | 56.1 | 0.71 |
| HIGH | 0.0167 | | 34.1 | 0.428 | 30.6 | 0.385 | 64.7 | 0.81 |
| LOW | 0.0083 | 90.00 | 17.9 | 0.225 | 32.4 | 0.407 | 50.3 | 0.63 |
| MED | 0.0125 | | 27.0 | 0.339 | 32.4 | 0.407 | 59.4 | 0.75 |
| HIGH | 0.0167 | | 36.1 | 0.453 | 32.4 | 0.407 | 68.5 | 0.86 |
| LOW | 0.0083 | 95.00 | 18.9 | 0.238 | 34.2 | 0.430 | 53.1 | 0.67 |
| MED | 0.0125 | | 28.5 | 0.358 | 34.2 | 0.430 | 62.7 | 0.79 |
| HIGH | 0.0167 | | 38.1 | 0.479 | 34.2 | 0.430 | 72.3 | 0.91 |
| LOW | 0.0083 | 100.00 | 19.9 | 0.250 | 36.0 | 0.453 | 55.9 | 0.70 |
| MED | 0.0125 | | 30.0 | 0.377 | 36.0 | 0.453 | 66.0 | 0.83 |
| HIGH | 0.0167 | | 40.1 | 0.504 | 36.0 | 0.453 | 76.1 | 0.96 |
| LOW | 0.0083 | 105.00 | 20.9 | 0.263 | 37.8 | 0.475 | 58.7 | 0.74 |
| MED | 0.0125 | | 31.5 | 0.396 | 37.8 | 0.475 | 69.3 | 0.87 |
| HIGH | 0.0167 | | 42.1 | 0.529 | 37.8 | 0.475 | 79.9 | 1.00 |
| LOW | 0.0083 | 110.00 | 21.9 | 0.275 | 39.6 | 0.498 | 61.5 | 0.77 |
| MED | 0.0125 | | 33.0 | 0.415 | 39.6 | 0.498 | 72.6 | 0.91 |
| HIGH | 0.0167 | | 44.1 | 0.554 | 39.6 | 0.498 | 83.7 | 1.05 |
| LOW | 0.0083 | 115.00 | 22.9 | 0.288 | 41.4 | 0.520 | 64.3 | 0.81 |
| MED | 0.0125 | | 34.5 | 0.434 | 41.4 | 0.520 | 75.9 | 0.95 |
| HIGH | 0.0167 | | 46.1 | 0.579 | 41.4 | 0.520 | 87.5 | 1.10 |
| LOW | 0.0083 | 120.00 | 23.9 | 0.301 | 43.2 | 0.543 | 67.1 | 0.84 |
| MED | 0.0125 | | 36.0 | 0.453 | 43.2 | 0.543 | 79.2 | 1.00 |
| HIGH | 0.0167 | | 48.1 | 0.605 | 43.2 | 0.543 | 91.3 | 1.15 |

TABLE 2B

Ketamine Formulations including 15% Captisol ®
Example of one potential target ketamine
concentration and one potential or theoretical
Captisol ® concentration attuned to an infusion pump

| | Basal | Ketamine | | | |
|---|---|---|---|---|---|
| Pump Strength | Rate ml/hr | Strength mg/ml | Basal Dose mg/24 hr | Bolus Dose mg/24 hr | Total Dose mg/24 hr |
| LOW | 0.00833 | 96.00 | 19.2 | 34.6 | 53.8 |
| MED | 0.01250 | | 28.8 | 34.6 | 63.4 |
| HIGH | 0.01667 | | 38.4 | 34.6 | 73.0 |

| | Basal | Captisol ® (approximately 15% in solution) | | | |
|---|---|---|---|---|---|
| Pump Strength | Rate ml/hr | Strength mg/ml | Basal Dose mg/24 hr | Bolus Dose mg/24 hr | Total Dose mg/24 hr |
| LOW | 0.00833 | 150.00 | 30.0 | 54.0 | 84.0 |
| MED | 0.01250 | | 45.0 | 54.0 | 99.0 |
| HIGH | 0.01667 | | 60.0 | 54.0 | 114.0 |

TABLE 2C

Ketamine Formulations including 20% Captisol ®
Example of one potential target ketamine
concentration and one potential or theoretical
captisol concentration attuned to an infusion pump

| | Basal | Ketamine | | | |
|---|---|---|---|---|---|
| Pump Strength | Rate ml/hr | Strength mg/ml | Basal Dose mg/24 hr | Bolus Dose mg/24 hr | Total Dose mg/24 hr |
| LOW | 0.00833 | 108.00 | 21.6 | 38.9 | 60.5 |
| MED | 0.01250 | | 32.4 | 38.9 | 71.3 |
| HIGH | 0.01667 | | 43.2 | 38.9 | 82.1 |

| | Basal | Captisol ® (approximately 20% in solution) | | | |
|---|---|---|---|---|---|
| Pump Strength | Rate ml/hr | Strength mg/ml | Basal Dose mg/24 hr | Bolus Dose mg/24 hr | Total Dose mg/24 hr |
| LOW | 0.00833 | 200.00 | 40.0 | 72.0 | 112.0 |
| MED | 0.01250 | | 60.0 | 72.0 | 132.0 |
| HIGH | 0.01667 | | 80.0 | 72.0 | 152.0 |

Example 4B. Advantages Provided by Sulfobutyl-Ether-Beta-Cyclodextrin

A review of the advantages and disadvantages of Captisol® with regard to efficacy, patentability and approvability for the unique ketamine product described herein was undertaken. This solubilizing pharmaceutical excipient/vehicle was developed specifically to reduce the risks presented by earlier cyclodextrins (CD) (e.g., beta-CD, Alpha-CD and even HP-CD).

TOXICITY: In general, it can be stated that sulfobutyl-ether-beta-cyclodextrin (SBE-β-CD) is safer than other identified non-substituted CDs. It also is generally accepted that SBE-β-CD is less metabolically active than the other substituted CD, hydroxypropyl-beta-cyclodextrin (HP-β-CD). These factors offer reduced non-target systemic effects and make Captisol® an appealing choice. The toxicity of CDs mostly revolves around kidney physiology and glomerular filtration dysfunction believed to arise from precipitation of cholesterol-CD complexes that impair glomerular function and GFR. Rate of CD delivery and total dose are a significant consideration in any safety evaluation with any CD and this is especially true with first generation CDs. The precipitation of early CDs, resulting in toxic kidney effects, were believed to result substantially from their relatively poor aqueous solubility. CDs with polar substitutes that increased aqueous solubility, thereby reducing kidney toxicity while still retaining the complexing and solubilizing capacity of the original compounds were eventually produced. According to the European Medicines Agency, the total plasma clearance for HP-β-CD and SBE-β-CD in all species tested is similar to the glomerular filtration rate. The t½ varies from 20 to 100 minutes, which implies high aqueous solubility and/or rapid clearance from the body. The innovation represented by SBE-β-CD has successfully supported development of numerous parenteral products with IV and IM ROA (see Table 1).

While approved products containing Captisol® have not yet been designed for chronic or sub-chronic use—mostly being developed for IV or IM administration of poorly soluble agents in acute medically monitored environments—longer term daily exposure in animals has identified a No Observed Effects Level that is reassuring with regard to potential toxicity with repeated low-dose administration in humans. The NOEL in the rat was 80 mg/kg for SBE-β-CD daily IV injections for 1 month.

Early research in humans is also reassuring. In developing a parenteral form of carbamazepine. Two studies in humans with varying degrees of renal function showed that up to 35 g/day (700 mg/kg/day) of all aqueous-processed SBE-β-CD as an excipient can be safely administered intravenously every 6 hours for up to 7 days. Infusion rates of SBE-β-CD ranged from 292 to 4375 mg/min (durations of 30 to 2 minutes, respectively) and SBE-β-CD was well-tolerated with no clinically relevant side effects or changes in renal biomarkers. It was shown that HP-β-CD and SBE-β-CD are considered safe at relatively high doses and used most widely in parenteral products. Amounts of ca 250 mg/kg/day for 21 days (HP-β-CD) or 6 months (SBE-β-CD) are found safe in humans older than 2 years.

There is not much public data available that establishes safety parameters in subcutaneous (SC) ROA. However, there is not a generally held concern that findings would be substantially different between SC versus IM or IV dosing regarding kidney toxicity specifically. However, it has been reported that a product using Captisol® as an excipient established safety after one year of delivery to monkeys three times per week in split (BID) dosing.

Example 5. Increasing pH of Ketamine Formulation

Description:
The pH of a ketamine solution can be adjusted by the addition of an acid like HCl or a base like NaOH. In addition, a buffer can be used to achieve a stabilized target pH. Since ketamine has a pKa of 7.5, and the unionized has poor water solubility the titration of a ketamine HCl solution to a pH above pH 5.5 in water will cause precipitation of unionized ketamine from the solution. Addition of a complexing agent (such as SBE-β-CD, HP-β-CD, etc.), to complex the unionized ketamine and keep it in solution, or the addition of a co-solvent (such as propylene glycol, tween, or glycerin etc) to solubilize the unionized ketamine (forming an emulsion) will be necessary to prepare a ketamine solution at a target pH at least 0.5 pH point, and likely equal to or greater than 1 pH point higher than average pH in comparable strength USP ketamine HCl solutions which in our study has ranged from 3.93 in solutions formed from powdered ketamine HCl and 3.74 measured in USP bottles of ketamine 100 mg/mL.

Advantages:

Acidic solutions are believed to cause irritation with SC and IM injections. This may be due to the fact that the resulting protons mimic the environment of damaged tissue leading to a pain response. Formulation of neutral pH solutions have been utilized to reduce subcutaneous injection site irritation and pain although success may depend on other factors such as chemical irritation and tonicity. Raising the pH of a formulation, from below 5 to a pH of 5.0 or above, may help reduce injection site pain, irritation and reactions seen following SC injection of more acidic ketamine solutions (pH below 5). Thus, reduced acidity could be one part of the combined strategies including reduced tonicity and slow-continuous-low volume infusion (supplemented with as needed low volume bolus SC injections), to reduce injection site irritation and provide a better treatment experience for patients.

Example 6. Reducing Tonicity Through Formulation Technology

Description and Rationale:

Many existing commercial ketamine formulations (e.g. 50 and 100 mg/mL ketamine HCl) are hypertonic. Osmolarity is the total dissolved particles in a solution per given volume (liter). The closely related, osmolality is the total dissolved particles in solution per given mass (kilogram). Osmolality is more commonly measured experimentally such as by an osmometer. The values for osmolality and osmolarity however rarely differ in practice for most practical applications. The calculated osmolarity of a 100 mg/mL (freebase equivalent) ketamine HCl (concentration of 0.4206 mol/L) solution is 841 mOsmol/L, and the calculated osmolarity of a 50 mg/mL (freebase equivalent) ketamine HCl (concentration of 0.210 mol/L) solution is a 420 mOsmol/L. At both of these concentrations, the solution is hypertonic with human serum (~280-295 mOsm/L). While this limitation can be overcome by using lower concentrations of ketamine (e.g. 10 mg/mL), such low concentrations of ketamine are unsuitable and inconvenient for subcutaneous delivery due to the large injection volume required, thus necessitating a large bolus of delivery and a large device reservoir for prolonged delivery.

During the formulation of a ketamine solution it may be necessary to titrate the pH of the solution using an acid or base such as HCl or NaOH, respectively. During the neutralization process of ketamine HCl with NaOH to raise the pH, excess NaCl is generated, which can contribute to the measured osmolality of the solution. One way to reduce the osmolality of a ketamine solution is to remove this excess NaCl generated or avoid its formation in the first place. However, in practice, only a small amount of NaCl is expected to be produced during the titration of existing ketamine formulations (such as Ketalar) as the pH of a ketamine HCl solution will depend on the concentration of ketamine and will be within the target range specified (pH: 3.5-5.5). At 100 mg/mL (ketamine freebase equivalent) in water the pH is around 4. Thus, to raise the pH of this solution to a target of 5.5, NaOH will need to be added. In addition to ensure the unionized ketamine formed during the titration process remains soluble in the solution, it will be necessary to add a complexing or emulsifying agent. One example of a complexing agent is SBE-β-CD. This is in contrast to using the complexing agent SBE-β-CD (e.g., Captisol) since each captisol molecule has on average 6-7 ionizable sulfonic acid side chains (actual average DS=6.5). Based on this each mole of captisol contributes 8 osmoles (1 from the captisol molecule and 7 from the Na+ ions which interact with the sulfonic acid side chains) to a solution since when a molecule of captisol is dissolved in water (or comparable solution/matrix) it gives rise to 8 dissolved particles in the solution. According to the manufacturer of Captisol, a captisol solution in the range of 9.5-11.4% are iso-osmotic with blood and extracellular fluid. Higher concentrations that are commonly used (up to 30%) are hyperosmotic. A 20% SBE-β-CD solution (with a degree of substitution comparable to captisol e.g., 6.5) is reported to have an osmolality of 785 mOsm/kg. The high osmolality comes mostly from the fact that there are 7 $Na^+$ ions per Captisol® molecule. A 15% solution of Captisol® containing 100 mg/mL of ketamine HCl would have a calculated osmolarity of 1396 mOsmol/L (555 mOsmol/L from captisol+841 mOsmol/L from ketamine HCl). However, since Captisol® contains ~7 anionic sulfonate side chains that could interact with up to 7 ionized ketamine cation molecules, the excess NaCl formed in this formulation, could be removed to substantially reduce the number of dissolved solids in solution and thus the osmolality. The calculated osmolarity of such a solution consisting of 15% captisol containing 100 mg of ketamine, without any NaCl, is 490.3 mOsmol/L. This value of 490.2 mOsmol/L is thus reduced substantially over that of current 100 mg/mL commercial solutions of ketamine of 841 mOsmol/l.

There are a number of possibilities to prepare a captisol-ketamine salt complex formulation, which would exhibit reduced tonicity relative to comparable solutions (e.g., with comparable ketamine concentrations involving different acid salt complexes) from the absence of introduction or removal of formed NaCl in the solution. Strategies which may accomplish this include: dialysis (to remove excess salt from the prepared ketamine-captisol solution), or utilisation of ion exchange resins (or comparable solid phase matrix for ion exchange such as silica or zeolites) at various stages of the formulation of the ketamine-Captisol® solution.

Proposed Processes for Preparing a Reduced Osmolality Captisol®-Ketamine NaCl-Reduced Formulation:

Process A:

To reduce the osmolality of a solution it is necessary to reduce the total number of dissolved particles in the solution. In the case of SBE-β-CD, its acid base properties are able to be exploited very conveniently to achieve this aim. For example, by replacing these Na+ cations on captisol with an ionized ketamine cation, the osmolality of the solution may be substantially reduced over a standard SBE-β-CD-Na+-ketamine HCl mixture in which excess and unnecessary NaCl will be present from the acid-base reaction between ketamine HCl and Captisol®-Nat. Thus, a salt-free Captisol®-ketamine formulation will have substantially reduced osmolality relative to the formulation obtained from mixing Captisol®-Nat with ketamine HCl.

Because of the presence of ~7 ionizable sulfonic acid side chains per captisol molecule (or equivalently substituted SBE-β-CD) the formulation would require less than a molar equivalent of captisol to counterbalance and dissolve 1 mole of ionized ketamine in solution (for example ⅐th or 0.14 molar equivalents). Or, in other words, one mole of Captisol® could form a salt with up to 7 moles of ketamine. Since some ketamine can also complex with the captisol core, solubilization of an additional mole of ketamine may be possible, thus bring the ratio of 1 mole of Captisol® to 8 moles of ketamine. Furthermore, complexation of the ketamine within the captisol molecule may further reduce the osmolality of the solution depending on the strength of the complexation interaction. Assuming an approximately 1:7 ratio of Captisol® to ketamine, a 128.8 mg of ketamine ($5.42 \times 10^{-4}$ mol) would require 154.5 mg captisol acid (7.69 e-5 mol). The calculated osmolarity of this 128.8 mg ketamine/mL and 154.5 mg/mL Captisol® solution would be about 619 mOsmol/L. The calculated osmolarity of a 100 mg/mL (freebase equivalent) ketamine HCl (0.4206 mol/L) solution is 841 mOsmol/L. Thus, the described Captisol®-ketamine solution has reduced tonicity relative to a 100 mg/mL ketamine HCl solution with a higher ketamine concentration. It has been reported that the optimal osmolality limit for drug products intended for subcutaneous and intramuscular injection is from about 600 to about 800 mOsm/kg.

In one example, an acidic (such as a sulfonic acid or carboxylic acid containing) ion exchange resin could be used to generate the acidic or protonated forms of SBE-β-CD (while removing the Na+ ions from the solution). Examples of some resins include, but are not limited to, strong cation exchangers (sulfonic acid containing) such as Amberlite IR-120 Plus(H), Amberlite 15, Amberlite 1200 (H), DOWEX 50WX2-100, DOWEX 50WX2-200, DOWEX 50WX2-400, DOWEX 50WX4-50, DOWEX 50WX4-100, DOWEX 50WX4-200, DOWEX 50WX4-200R, and DOWEX 50WX4-400. As well as "weak cation exchangers" (Carboxylic acid containing) such as Amberlite CG-50, Amberlite IRC-50, Amberlite IRC-50S, Amberlite IRP-64.

The replacement of the $Na^+$ cation for $H^+$ on the SBE-β-CD molecule would be achieved by preparing a solution of SBE-β-CD (in water, organic or mixed phase aqueous-organic or organic-organic solvents) at a given concentration and running this solution of SBE-β-CD through a column containing the appropriate immobilized acidic form ion exchange material. The $Na^+$ on SBE-β-CD sulfonate side chains would be exchanged for the protons on the immobilized resin to produce SBE-β-CD-acid. The $Na^+$ would be trapped on the immobilized ion exchange material and thus would not be eluted from the column. The generated acidic SBE-β-CD could then be stored (in solution or solid phase) and mixed with ketamine freebase immediately, or at a later date, to generate the SBE-β-CD-ketamine salt complex. The resulting solution could be adjusted for volume, additional additives and desired pH using NaOH or other appropriate base, as this would contribute only a small amount to the total osmolality of the solution. This approach may also include the addition of buffers, co-solvents, and other excipients known in the art to achieve pH and/or solubilizing stability.

Process B:

A protonated and thus ionized ketamine molecule, originating from any appropriate ketamine salt (which may include monovalent and novel divalent and/or trivalent salts and/or various anions that may have formulation advantages and are thus to be considered as described elsewhere in this document), could be exchanged with an anion and thus attached to a basic anion exchange resin. Such resins include but are not limited to a basic carboxylate or sulfonic acid functionalized resins, numerous variations of these forms exist including but not limited to Amberlite IR-120 Plus, Amberlite IRP-69, Dowex 88, MSC-1). In some preparations, the basic form of the resin could also be prepared from a commercially available cation exchange resin using standard ion exchange techniques; this would allow greater control over the use of various cationic resins ($K+$, $Ca^{2+}$, $Mg^{2+}$, $NH_4^+$, etc.), which may not be readily commercially available, to facilitate the exchange process with the protonated ketamine. For example, a solution of the desired cation salt (such as KCl, KBr, $NH_4Cl$, $MgCl_2$, etc.) would be passed through a column containing the immobilized ion exchange resin, leading to exchange of the desired cation onto the immobilized resin. This resin could then be used to prepare the ketamine cation resin by running a solution of ketamine as any appropriate ketamine salt (which may include monovalent and novel divalent and/or trivalent salts and/or various anions that may have formulation advantages and are thus to be considered as described elsewhere in this document) through the column to form the ketamine-cation ion exchange resin. Once the ketamine loaded cation exchange resin is prepared, a solution of SBE-β-CD in water or other appropriate solvent (for example, but not limited to organic solvents such as methanol, ethanol, propanol, isopropanol), or solvent mixtures containing two or more components (aqueous-organic organic-organic, etc.) could then be run through a column, containing the ketamine-bound ion exchange resin. The resin would exchange $Na^+$ on the sulfonic acid side chains of SBE-β-CD for the ionized ketamine cation and thus a ketamine-SBE-β-CD salt solution with reduced NaCl would be formed. Unwanted $Na^+$ would thus be removed from the solution by trapping to the ion exchange resin. The resulting solution could be adjusted for volume, additional additives and desired pH using NaOH or other appropriate base, as this would contribute only a small amount to the total osmolality of the solution. The resulting ketamine-SBE-β-CD salt could also be isolated and stored for use later or for direct formulation. This approach may also include the addition of buffers, co-solvents, and other excipients known in the art to achieve pH and/or solubilizing stability.

Process C:

Captisol® and ketamine HCl could be mixed in the appropriate solution to produce a solution containing an equilibrium mixture of ketamine-Captisol® salt, ketamine HCl, captisol-$Na^+$ salt and NaCl. Processes to remove the NaCl could shift the equilibrium to favor the captisol-ketamine salt complex while removing NaCl. The removal of NaCl could be achieved through the use of dialysis. For example, the ketamine-Captisol® solution could be placed in a dialysis bag (or other appropriate container) with an appropriate molecular weight cut-off (such as 100, or 200 Daltons) to selectively remove NaCl from the solution while leaving ketamine and Captisol® behind.

Process D:

Various filtration-based methods are commonly utilized to selectively remove small molecular weight dissolved salts from solutions. Examples which are of interest for removing NaCl from the ketamine-Captisol® formulation include crossflow membrane filtration methods such as ultrafiltration and nanofiltration.

Filtration methods using membranes with MWCOs of 200 Daltons or below could be used to selectively remove NaCl from a solution. The ketamine-captisol mixture (containing excess NaCl in equilibrium with ketamine and Captisol®) could be formed at a target concentration and the excess NaCl present removed by these filtration processes and the resulting concentrated solution (or solid) could be stored or immediately diluted to produce a reduced NaCl ketamine-Captisol®-salt solution.

In addition to Processes A-D above, other routes and techniques could be utilized to produce the ketamine-Captisol® salt (which may be isolated as a solid or formed in solution as a stock or at the final target concentration). These include but are not limited to, altered synthetic routes (production of protonated Captisol®), liquid-liquid extraction techniques, solid-phase extraction techniques, immobilized liquid extraction, chromatography techniques (ion exchange, fractionation etc), crystallization techniques, electrophoresis, electrodialysis, and freezing desalination.

Ketamine Osmolality:

Commercial ketamine formulations of 50 mg/mL and 100 mg/mL ketamine HCl are hypertonic due to a high osmolality. This has in part limited the administration of ketamine solutions via subcutaneous (SC) routes and reduced the dosage of ketamine that may be comfortably administered. Osmolality is defined as the total dissolved particles in a solution of a given mass (typically a kilogram, osmolarity is the comparable measure but per volume, in this case typically liter and is easier to calculate and for that reason is used for calculations. These numbers rarely differ in practice for aqueous solutions). The calculated osmolarity (based on mOsmol/liter) of a 100 mg/mL ketamine (freebase equivalent) HCl solution is 841 mOsmol/L. This high osmolality is responsible for the hypertonicity of commercial ketamine formulations at this concentration. Hypertonicity may contribute to local irritation of tissue following SC injection. Thus, ketamine's documented irritation following SC injection may result in part from hypertonicity of existing formulations. Accordingly, products for IM or SC injection may be formulated to have an osmolality with an upper limit of about 600 mOsmol/kg to about 800 mOsmol/kg. To reduce the osmolality of a solute it is necessary to reduce the total number of dissolved particles in the solution. Since a single mole of Captisol® can theoretically form an ionic interaction with 7 molecules of ketamine (and may complex an additional molecule of ketamine), this formulation will dramatically reduce the amount of anion needed to be dissolved in the solution, thus reducing the osmolality compared to a formulation prepared by mixing captisol-Na$^+$ and ketamine HCl and even potentially reduced osmolality relative to existing ketamine HCl formulations at comparable concentrations. A reduced osmolality will lead to greater injection site tolerability.

Assuming an approximately 1:7 ratio of Captisol® to ketamine, 128.8 mg of ketamine freebase (5.42×10$^{-4}$ mol) would require 154.5 mg captisol acid (7.69×10$^{-5}$ mol) for acid-base neutralization. The calculated osmolarity of the resulting 128.8 mg ketamine, 154.5 mg Captisol®/mL solution is approximately 619 mOsmol/L. This is close to the upper osmolality limit reported in the literature. By comparison, the calculated osmolarity of a 100 mg/mL (freebase equivalent) ketamine HCl (0.4206 mol/L) solution is 841 mOsmol/L. The proposed formulation strategy increases the amount of deliverable ketamine while reducing the osmolality to an acceptable range. This brings the osmolality of the final solution closer to physiological osmolality (and closer to isotonic) and thus reducing potential injection site pain and irritation, without compromising deliverable ketamine. This is important, as SC pump reservoirs have limited volume capacities due to convenience for patients and product mechanics. Thus, it is not feasible to reduce the concentration of ketamine without compromising the available dosage. Volume of drug delivered also can influence injection site pain, irritation and reaction and thus keeping the injection volume small via a continuous infusion can further reduce irritation. Thus, the product would be expected to reduce irritation and adverse effects upon local tissues in comparison to standard formulations and routes of administration in several ways potentially including: low injection volume, administration as a continuous infusion and/or or low-dose bolus (e.g., lower than other current low dose bolus approaches), reduced osmolality and pH that more closely approaches the physiologic pH of target delivery tissues.

Example 7. Reducing Tonicity Through Utilization of Novel Ketamine Divalent, Trivalent, and Higher Order Salts Description:

The use of divalent and trivalent ketamine salts could reduce the osmolality of the final solution relative to the use of a monovalent salt like HCl, HBr, etc. For example, a ketamine hemi-fumarate salt will contain 2 moles of ketamine per 1 mole of fumaric acid, or for every 1 osmol ketamine there will be 0.5 osmol fumaric acid (1.5 osmol equivalents per salt complex). The total dissolved particles in solution will thus be reduced relative to ketamine HCl (2 osmol equivalents vs. 1.5 osmol equivalents). In addition, a trivalent salt such as citrate could theoretically form a 1:3 molar ratio (e.g., 1 mole of citric acid can react with up to 3 moles of ketamine, thus for each osmol of ketamine, 0.33 osmol of citrate is necessary for 1 osmol ketamine, potentially reducing 2 osmol equivalents for a standard ketamine HCl solution compared to 1.33 osmol in a ketamine citrate solution). While in practice it may be less than 3 equivalents of ketamine solubilized per mole of trivalent acid, because of pKa limitations, however use of such trivalent anion complexes may give functional advantages such as being able to solubilize greater than 2 molar equivalents of ketamine. Finally, the same argument has been described above for SBE-β-CD (such as captisol), which contains on average from about 6 to about 7 sulfonic acid sites per molecule. Thus, a single mole of SBE-β-CD-acid (such as Captisol®-acid) with degree of substitution of 7 sulfonic acid side chains can protonate 7 moles of ketamine or for each osmol of ketamine, 0.14 osmols of Captisol® are needed (e.g., 1.14 osmol equivalents total). Other potential multivalent anions for consideration in this aspect of this description of our formulation innovation include but are not limited to: sulfate, tartrate, glutarate, succinate, maleate, malonate, and phosphate as well as other SBE-β-CDs with varying degrees of substitution (though preferably 6-7 such as Captisol®) and various additional anionic cyclodextrins with varying degrees of substitution including carboxymethyl-β-CD, succinyl-β-CD, 2-carboxyethyl-β-CD, β-CD-phosphate, beta-β-sulfate, sulfoethyl-β-CD, and SBE-β-CD.

These described techniques may allow development of higher concentration ketamine products than standard ketamine HCl products without raising the tonicity of the solution, a property that would be reasonably expected to increase subcutaneous tissue tolerance. Likewise, a comparably concentrated ketamine formulation could be prepared with lower osmolality and thus in a more acceptable tonicity range for SC injections. Such formulations are expected to reduce osmolality of ketamine solutions relative to a comparable concentration of a standard ketamine HCl formulations and in some cases even reduced compared to lower concentrations of ketamine HCl, thus allowing greater dose delivery and/or greater comfort to the patient. Reduced osmolality combined with other features of the formulation such as a raised pH (e.g., less acidic solution) and low volume continuous infusion, and small volume bolus, is expected to produce less tissue irritation and/or injection site pain and/or noxious stimuli as discussed herein.

Example 8. An Efficacy and Safety Study of Ketamine in Participants with Major Depressive Disorder Detailed Description: The purpose of this study is to evaluate the efficacy of ketamine as antidepressant therapy where ketamine (administered as a 100 milligram (mg) subcutaneous (SC) injection at Day 1, Day 28 and Day 56 during the 12-week double-blind treatment period) is compared to a placebo based on the change from baseline to 12-week endpoint in depressive symptoms as measured by the total score on the Hamilton Depression Rating Scale (HDRS), in participants diagnosed with Major Depressive Disorder (MDD) who have had a suboptimal response to the current standard oral antidepressant therapy and have a screening high sensitivity C-Reactive Protein (hsCRP)>=0.300 milligram per deciliters (mg/dL) (International System of Units (SI) 3.00 mg/L). A cohort of subjects with hsCRP<0.300 milligram per deciliter will also be enrolled to allow a better understanding of the relationship between CRP and clinical changes.

| | Descriptive Information |
|---|---|
| | A double-blind, placebo-controlled, multicenter study of ketamine as antidepressant treatment in adults with major depressive disorder. Participants will be randomly assigned to receive either placebo, ketamine 25 milligram (mg), or ketamine 50 mg at a ratio of 1:1:1 at Day 1, 28 and 56. Participants will primarily be assessed for change from baseline in Hamilton Depression Rating Scale (HDRS17) score at Week 12. Safety will be monitored throughout the study |
| Brief Summary | The purpose of this study is to evaluate the efficacy of ketamine as antidepressant therapy where ketamine (administered as a 25 or 50 milligram (mg) subcutaneous (SC) injection at Days 1, 7, 14, 21, 28, 42, and 56 during the 12-week double-blind treatment period) is compared to adjunctive placebo based on the change from baseline to 12-week endpoint in depressive symptoms as measured by the total score on the Hamilton Depression Rating Scale (HDRS), in participants diagnosed with Major Depressive Disorder (MDD) who have had a suboptimal response to the current standard oral antidepressant therapy and have a screening high sensitivity C-Reactive Protein (hsCRP) >= 0.300 milligram per deciliters (mg/dL) (International System of Units (SI) 3.00 mg/L). A cohort of subjects with hsCRP < 0.300 milligram per deciliter will also be enrolled to allow a better understanding of the relationship between CRP and clinical changes. |
| Study Type | Interventional |
| Study Phase | Phase 2 |
| Study Design | Allocation: Randomized<br>Intervention Model: Parallel Assignment<br>Masking: Quadruple (Participant, Investigator, Outcomes Assessor)<br>Primary Purpose: Treatment |
| Condition | Depressive Disorder, Major |
| Intervention | Drug: ketamine<br>Participants will receive ketamine 25 or 50 mg as subcutaneous injection on Days 1, 7, 14, 21, 28, 42, and 56.<br>Drug: Placebo<br>Participants will receive matching placebo on Days 1, 7, 14, 21, 28, 42, and 56. |
| Study Arms | Experimental: ketamine 25 or 50 milligram (mg)<br>Participants will receive ketamine 25 or 50 as subcutaneous injection on Days 1, 7, 14, 21, 28, 42, and 56.<br>Intervention: Drug: ketamine 25 or 50 mg<br>Placebo Comparator: Placebo<br>Participants will receive matching placebo on Days 1, 7, 14, 21, 28, 42, and 56.<br>Intervention: Drug: Placebo |
| Eligibility Criteria | Inclusion Criteria:<br>Participants must have a primary DSM-5 diagnosis of MDD<br>Must have a HDRS total score greater than or equal to (>=) 18 at screening and predose at Day 1, as recorded by the remote independent rater and must not demonstrate an improvement of > 25 percent (%) on their HDRS total score from the screening to baseline visit<br>Must be medically stable on the basis of physical examination, medical history, vital signs, clinical laboratory tests and 12-lead ECG performed at screening. If there are abnormalities, the participant may be included only if the investigator judges the abnormalities or deviations from normal to be not clinically significant. This determination must be recorded in the subject's source documents and initialed by the investigator<br>Participants with hypothyroidism who are on stable treatment for 3 months prior to screening are required to have thyroid stimulating hormone (TSH) and free thyroxine (FT4) obtained. If the TSH value is out of range, but FT4 is normal, such cases should be discussed directly with the medical monitor before the subject is enrolled. If the FT4 value is out of range, the participant is not eligible<br>Exclusion Criteria:<br>Any other current Axis one psychiatric condition, including, but not limited to, MDD with current psychotic features, bipolar disorder (including lifetime diagnosis), obsessive-compulsive disorder, borderline personality disorder, eating disorder (e.g., bulimia, anorexia nervosa), or schizophrenia (lifetime). The MINI will be used to screen for comorbid psychiatric diagnoses. As noted above, subjects with a diagnosis of comorbid GAD, Post-Traumatic Stress Disorder, Persistent Depressive Disorder, ADHD, Social Anxiety Disorder, Panic Disorder with or without agoraphobia or Nicotine/Caffeine Dependence may be included, if the investigator considers MDD to be the primary diagnosis |

| | Descriptive Information |
|---|---|
| | A history of alcohol or substance use disorder (abuse/dependence) within 6 months prior to screening (nicotine and caffeine dependence are not exclusionary) |
| | A current or recent (within the past year) history of clinically significant suicidal ideation (corresponding to a score of >= 3 for ideation) or any suicidal behavior within the past year, as validated on the C-SSRS at screening or baseline. Subjects with a prior suicide attempt of any sort, or history of prior serious suicidal ideation/plan should be carefully screened for current suicidal ideation and only included at the discretion of the investigator |
| | More than 3 failed antidepressant treatments (of adequate dose and duration) in the current episode of depression (verified by the MGH-ATRQ) |
| | Length of current major depressive episode > 60 months |
| Current Primary Outcome Measures | Change From Baseline in Hamilton Depression Rating Scale (HDRS17) Total Score at Week 12 [Time Frame: Baseline up to Week 12] The HDRS17 is a clinician-administered rating scale designed to assess the severity of symptoms in participants diagnosed with depression with a score range of 0 to 52. It is the most widely used symptom severity measure for depression. Each of the 17 items is rated by the clinician on either a 3- or a 5-point scale. The higher the score, the more severe the depression. |
| Current Secondary Outcome Measures | Change From Baseline in Snaith Hamilton Pleasure Scale (SHAPS) Total Score at Week 12 [Time Frame: Baseline and Week 12] Anhedonia, the inability to experience pleasure, is a core symptom of depression. The Snaith-Hamilton Pleasure Scale (SHAPS) is a short, 14-item instrument to measure anhedonia, which has been shown to be valid and reliable in normal and clinical samples. Each of the 14 items has a set of four response categories: Definitely Agree (=1), Agree (=2), Disagree (=3), and Definitely Disagree (=4). A higher total score indicates higher levels of state anhedonia. |
| | Change From Baseline in Clinical Global Impression-Severity (CGI-S) Total Score at Week 12 [Time Frame: Baseline and Week 12] The CGI-S provides an overall clinician-determined summary measure that takes into account all available information, including knowledge of the participant's history, psychosocial circumstances, symptoms, behavior, and the impact of the symptoms on the participant's ability to function. The CGI evaluates the severity of psychopathology from 1 to 7. Higher score indicates more severity. |
| | Change From Baseline in Patient Health Questionnaire (PHQ-9) at Week 12 [Time Frame: Baseline and Week 12] The PHQ-9 is used as a participant-reported measure of depressive symptomatology. The PHQ-9 is a 9-item scale, where each item is rated on a 4-point scale (0 = Not at all, 1 = Several Days, 2 = More than half the days, and 3 = Nearly every day), with a total score range of 0 to 27. The recall period is 2 weeks. High score indicates higher symptoms. |
| | Change From Baseline in Functional Assessment of Chronic Illness Therapy (FACIT) at Week 12 [Time Frame: Baseline and Week 12] The FACIT-Fatigue is a questionnaire that assesses self-reported tiredness, weakness, and difficulty conducting usual activities due to fatigue. The total FACIT-Fatigue score ranges from 0 to 52, with a higher score indicating less fatigue. |
| | Number of Participants as Remitters [Time Frame: Week 12] Remitters are defined as participants with HDRS17 total score <= 7 at 12 week. |
| | Number of Participants as Responders [Time Frame: Baseline and Week 12] Participants with >= 50 percent (%) improvement on the HDRS17 total score from baseline at Week 12. |
| | Number of Participants with Adverse Events (AEs) and Serious AEs [Time Frame: Screening up to End of Follow-up Phase (approximately up to 32-35 weeks)] An adverse event (AE) is any untoward medical occurrence in a participant who received study drug without regard to possibility of causal relationship. A serious adverse event (SAE) is an AE resulting in any of the following outcomes or deemed significant for any other reason: death; initial or prolonged inpatient hospitalization; life-threatening experience (immediate risk of dying); persistent or significant disability/incapacity; congenital anomaly. |
| | The change from baseline to endpoint on the Hamilton Depression Rating Scale (HDRS17) total score [Time Frame: Baseline up to Week 12] The HDRS17 is a clinician-administered rating scale designed to assess the severity of symptoms in patients diagnosed with depression with a score range of 0 to 52. Questions are related to symptoms such as depressed mood, guilt feelings, suicide, sleep disturbances, anxiety levels and weight loss. The higher the score, the more severe the depression. |

Example 9. An Efficacy and Safety Study of Ketamine in Participants with Acute Post-Operative Pain Detailed Description: The purpose of this study is to evaluate the efficacy of ketamine as therapy for post-operative pain where ketamine (administered as up to 100 milligram (mg) subcutaneous (SC) injection up to 10 days during the double-blind treatment period) is compared to opioid standard of care, on the change from baseline to day 3 primary endpoint in pain symptoms as measured by the Numeric Pain Rating Scale (NPRS), in participants diagnosed with Acute Post-operative Pain (POP). Secondary endpoints will include the PROMIS Pain Intensity Scale, PROMIS Physical Function, Patient Global Impression of Change (PGIC), cumulative opioid usage, and cumulative analgesic usage.

| | Descriptive Information |
|---|---|
| | A double-blind, placebo-controlled, multicenter, non-inferiority study of ketamine as pain management in adults with acute post-operative pain. Participants will be randomly assigned to receive either ketamine up to 100 milligram (mg) or opioid standard of care at a ratio of 1:1 up to 10 days following knee replacement surgery. The primary endpoint will be change from baseline to day 3 as measured by the Numeric Pain Rating Scale (NPRS). Safety will be monitored throughout the study. |
| Brief Summary | The purpose of this study is to evaluate the safety and efficacy of ketamine as therapy where ketamine (administered as up to 100 milligram (mg) subcutaneous (SC) injection at up to 10 days of the double-blind treatment period) is compared to opioid standard of care on the change from baseline to Day 3 endpoint in pain symptoms as measured by the NPRS in participants diagnosed with Acute Post Operative Pain (POP). |
| Study Type | Interventional |
| Study Phase | Phase 2 |
| Study Design | Allocation: Randomized 1:1<br>Intervention Model: Parallel Assignment<br>Masking: Triple (Participant, Treating Investigator, Outcomes Assessor)<br>Primary Purpose: Treatment |
| Condition | Post-operative Pain |
| Intervention | Drug: ketamine<br>Participants will receive ketamine up to 100 mg as subcutaneous injection up to 10 days.<br>Drug: opioid standard of care<br>Participants will receive active comparator up to 10 days |
| Study Arms | Experimental: ketamine up to 100 milligram (mg)<br>Participants will receive ketamine or active comparator up to 10 days.<br>Intervention: Drug: ketamine up to 100 mg<br>Active Comparator: opioid standard of care<br>Participants will receive matching active comparator up to 10 days. |
| Eligibility Criteria | Inclusion Criteria:<br>Participants must undergo knee replacement surgery<br>Must be medically stable on the basis of physical examination, medical history, vital signs, clinical laboratory tests and 12-lead ECG performed prior to surgery. If there are abnormalities, the participant may be included only if the investigator judges the abnormalities or deviations from normal to be not clinically significant. This determination must be recorded in the subject's source documents<br>Exclusion Criteria:<br>Treatment with another prescription analgesic during study participation<br>A history of alcohol or substance use disorder (abuse/dependence) within 6 months prior to screening (nicotine and caffeine dependence are not exclusionary)<br>Active participation in another interventional clinical study |
| Current Primary Outcome Measures | Change from baseline to day 3 as measured by the Numeric Pain Rating Scale (NPRS). |
| Current Secondary Outcome Measures | PROMIS Pain Intensity Scale<br>PROMIS Physical Function<br>Patient Global Impression of Change (PGIC)<br>Cumulative opioid usage<br>Cumulative analgesic usage.<br>Number of Participants as Responders [Time Frame: Baseline and Day 3]<br>Participants with >= 50 percent (%) improvement on the NPRS from baseline and Day 3.<br>Number of Participants with Adverse Events (AEs) and Serious AEs<br>Time Frame Screening up to End of Follow-up Phase. |

Example 10. Preparation of a Ketamine Formulation for Subcutaneous Injection Currently available Ketamine HCl is known to cause local tissue site irritation when injected subcutaneously. Symptoms can include erythema, itching, swelling, pain and can result in a sterile abscess. This is believed to be due to the acidic pH (~4), high osmolarity, the presence of ketamine itself, or a combination of these factors.

A ketamine formulation suitable for subcutaneous injection was prepared according to the general protocol shown in Scheme 1. The protocol provided herein was used to prepare a stable, high concentration ketamine solution with an osmolality near physiological levels (~300 mOsm/kg)

and a pH of ~5.5. The resulting formulated ketamine is expected to offer numerous advantages compared to other known formulations, including reduced pain at the injection site and other symptoms, including erythema, itching, swelling, and a decreased likelihood of developing a sterile abscess.

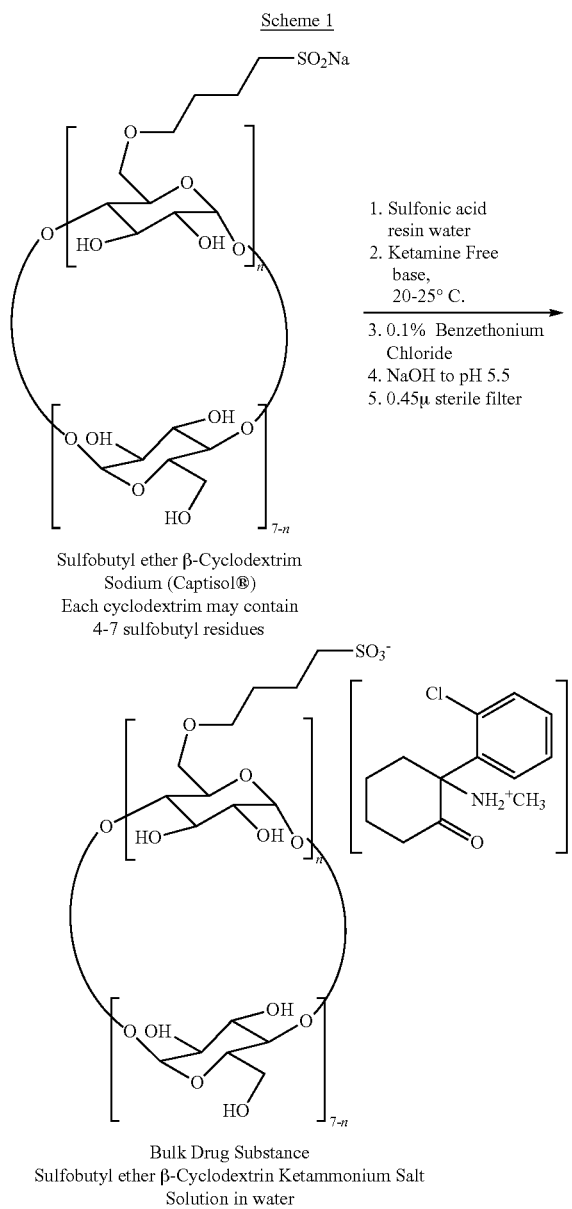

Scheme 1

Sulfobutyl ether β-Cyclodextrim Sodium (Captisol®)
Each cyclodextrim may contain 4-7 sulfobutyl residues 1. Sulfonic acid resin water
2. Ketamine Free base, 20-25° C.
3. 0.1% Benzethonium Chloride
4. NaOH to pH 5.5
5. 0.45μ sterile filter Bulk Drug Substance
Sulfobutyl ether β-Cyclodextrin Ketammonium Salt Solution in water Experimental Procedure for the Preparation of Bulk Drug Substance (BDS)

HPLC grade solvents were used throughout all procedures unless otherwise noted. Materials were sourced from indicated commercial suppliers and used as is unless otherwise noted. Equivalence points were determined by titration with 0.5M sodium hydroxide and the data was analyzed in Prism 8.

Captisol®:

Purchased from Ligand Pharmaceuticals, Inc. (Ligand) (pharmaceutical grade). The moisture content was verified by Karl Fisher analysis (6.5%). Captisol® is a poly-sulfobutylated β-cyclodextrin sodium form, with an average of 6.5 sulfobutyl groups per molecule and an average MW of 2,163.

Ketamine HCl:

Purchased from Spectrum Chemical and used without further purification. Free base ketamine was prepared from the HCl salt with concentrated sodium hydroxide and isolated by vacuum filtration according to the protocol described below.

Synthesis of Captisol® Acid.

Amberlite IR120 Hydrogen [Sigma-Aldrich (06428-1KG, Lot #BCBZ3814)] form resin (198 g, 4.4 meq/g, 20 equivalents) was soaked in HPLC grade water (400 mL) for 5 minutes and packed into a column (40 mm diameter). The resin was washed with 2 column volumes of HPLC grade water and was completely dried by applying compressed air for 10 minutes before the sample was applied. A solution of 15% Captisol® (90 mL) was applied to the column and allowed to flow by gravity into an Erlenmeyer flask. When the gravity flow ceased, compressed air was used to elute the remaining volume for 10 minutes. The eluent was frozen at −20° C., lyophilized and subjected to further drying via high vacuum (<0.01 mmHg) for 3 hrs. Every hour, the solid was removed from the vacuum, pulverized, and then placed back under vacuum. The final moisture content of the solid (5.80%) was determined by Karl-Fisher titration. The resulting white, free-flowing shiny solid (5.6 g) was stored in a foil-wrapped scintillation vial at −20° C.

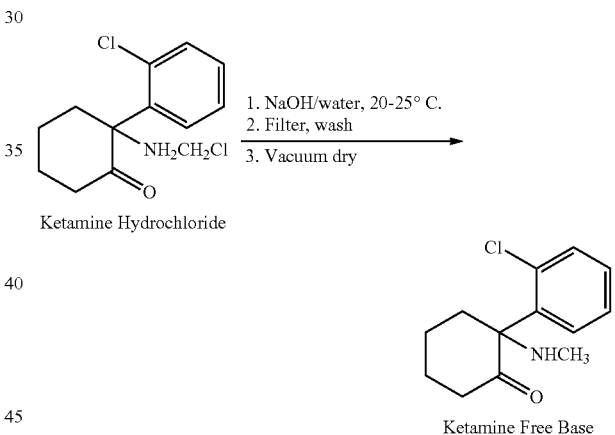

Ketamine Hydrochloride

1. NaOH/water, 20-25° C.
2. Filter, wash
3. Vacuum dry

Ketamine Free Base

Ketamine Freebase:

Ketamine hydrochloride (3.0 g, 10.9 mmol) was dissolved in dH$_2$O (100 mL). 2M NaOH was added with stirring until a cloudy white precipitate formed. An excess of base was added such that additional base did not lead to further precipitation. After sitting for 20 minutes the precipitate was collected by gravity filtration, washed with 300 mL of HPLC-grade water and dried under vacuum. Recovery of the precipitated freebase was 2.0 g. Purity was confirmed by HPLC and water content by Karl Fisher analysis. The identity was determined by NMR and GC-MS.

Resolution of S-Ketamine from Racemic Ketamine Free Base with Tartaric Acid.

R,S-ketamine free base (500 mg, 2.10 mmol) was dissolved in acetone (6.1 mL) and L-(+)-tartaric acid (315 mg, 2.10 mmol) was added. dH$_2$O (400 μL) was added and the mixture was heated to boiling. The solution was cooled to rt and then to 4° C. to crystallize into long white crystalline needles. The solids were collected (400 mg) and recrystallized once from acetone:water (8:1) at room temperature too form needle-like crystals (crop 1=270 mg). Specific rotation a=+74.47 (water, 25° C.). Literature α=+68.9 (water). The S-ketamine tartrate salt was dissolved in dH$_2$O and basified with excess 2M NaOH to form a white precipitate. The solid was collected by filtration, washed with HPLC grade water and dried in vacuo to afford S-ketamine free base (100 mg, 0.42 mmol) as a white, fluffy solid.

Synthesis of Ketamine-Captisol® Bulk Drug Substance BB105 (96 mg/mL Ketamine).

Captisol® acid (698 mg, moisture corrected 753 mg, for 14% w/v final concentration) was dissolved in HPLC grade water (4 mL) in a test tube with a teflon stirbar. The solution was stirred vigorously and racemic ketamine freebase (480 mg) was added via spatula in ~20-40 mg portions, each portion was allowed to completely dissolve before the next was added. The solid was agitated as necessary to facilitate dissolving. When the additions were complete, benzethonium chloride (5 mg, to give a final concentration of 0.1%) was added and 2M sodium hydroxide was added in small portions until the pH was raised to 5.5 (initial starting pH 1.39). A total of 146 µL was necessary. When complete, the solution was carefully transferred to a volumetric flask and the volume was brought up to 5 mL. The solution was syringe filtered with a 0.45 µM nylon filter and stored in a test tube under ambient air and wrapped in aluminum foil. Part of the volume was lyophilized to produce a white tablet solid that ground to a stable white powder (ket-cap). This resulting ket-cap powder did not visibly discolor and was not visibly deliquescent, even after sitting out on the lab bench under ambient conditions for several weeks. The powder was readily reconstituted with water. Osmolality readings were obtained immediately after preparation (465 mOsm/kg average vs control 0.9% saline 293 mOsm/kg).

Synthesis of Ketamine-Captisol® Bulk Drug Substance BB106 (70 mg/mL Ketamine)

Captisol acid (5.20% moisture, 10.0 g active, 10.066 g moisture corrected, for 10% w/v final) was dissolved in HPLC water (7.0 mL) in a test tube with a Teflon stir bar. The solution was stirred using a magnetic stir plate and racemic ketamine free base (700 mg) was carefully added portionwise via spatula (~50-70 mg portions) with agitation as needed to facilitate complete dissolution. The next portion was added only once the mixture became homogenous. After the ketamine addition, benzethonium chloride (10.0 mg, to give a final concentration of 0.1%) was added and the solution was titrated with small portions of 2M NaOH (163 µL final) to reach the target pH of 5.5 (final pH 5.51). The solution was then carefully transferred and diluted to a final volume of 10 mL in a volumetric flask and pH (pH 5.51). The solution was filtered through a 0.22 nylon sterile filter, and stored in a sealed vial at room temperature in the dark (foil). Osmolality readings were obtained immediately after preparation (299 mOsm/kg average vs control 0.9% saline 287.6 mOsm/kg).

Preparation of S-Ketamine-Captisol Bulk Drug Substance BB107 (70 mg/mL S-Ketamine)

Captisol acid (5.20% moisture, 100 mg active, 106.2 mg moisture corrected for 10% w/v final) was dissolved in HPLC water (0.75 mL) in a test tube with a stir bar. The solution was stirred and S-ketamine free base (70.1 mg) was added portionwise via spatula (~50-70 mg portions) with agitation. The next portion was added when the mixture became homogenous. After the ketamine addition, a solution of benzethonium chloride (10 mg/mL, 100 µL, 1.0 mg, 0.1%) was added and the solution was titrated with portions 2M NaOH (15 µL final) to reach pH 5.5 (final pH 5.59). The complex was diluted to 1.0 mL and osmolality readings were obtained (307.6 mOsm/kg average vs 0.9% saline 293.3 mOsm/kg). The solution was sealed, covered in foil and stored at room temperature.

One benefit of the process of formulating ketamine described above is the resulting osmolality. A summary of the final characteristics of the formulations prepared above is provided below in Table 3. Prepared in this way, the osmolality of the BDS solution BB105 was ~440 mOsmol/kg. The solution osmolality was then lowered further by using a 70 mg/mL target concentration instead of 96 mg/mL. This provided an isotonic solution consistent with 0.9% isotonic saline and on target with the salt content of the intended use, human tissue, which has an osmolality of about ~290 mOsm/kg. Thus, BB105 and BB106 offer improved pH and osmolality relative to standard ketamine HCl products of comparable concentration and potency. Moreover, the osmolality of BB105 and BB106 formulations created with the methods provided herein, 465 and 299 respectively, are dramatically less than the normal combination of ketamine HCl and Captisol® of 1252. Indeed, achieving an osmolality ⅓ to ¼ of a normal combination of ketamine and Captisol® provides meaningfully improved clinical utility and safety.

TABLE 3

Final Characteristics of Ketamine Formulations

|  | BB105 | BB106 | BB107 |
| --- | --- | --- | --- |
| Ketamine Concentration (mg/mL) | 96 | 70 | 70 |
| pH | 5.5 | 5.51 | 5.59 |
| Os molality (mOs m/kg) | 465 | 299 | 308 |

Additionally, the more neutral pH of the formulations of BB105, BB106, and BB107 (pH~5.5) compared to solutions ketamine HCl by itself (pH~3.6) indicates that the instant formulations are better suited for maintaining non-ionized ketamine in solution. Whereas ketamine HCl solutions are known to exhibit precipitation at elevated pHs around 5.5, the instant formulations do not show any precipitation. As the pKa of ketamine is ~7.5, stability of the instant formulations at a pH of 5.5 indicates that about 1% of non-ionized ketamine remains soluble.

The formulations of ketamine provided herein have also been observed to be stable over a substantial period of time. From a gross visual inspection there, was no visible precipitation of BB105 or BB106 after >4 months of storage. No degradation of the ketamine was observed on HPLC as well. Thus, the formulations provided herein demonstrate greater stability and maintenance of ketamine in solution at a higher pH in comparison to standard ketamine or ketamine HCl at comparable concentrations titrated to comparable pHs.

Example 11. A Safety and Tolerability Study of Ketamine Subcutaneous Formulations in Yorkshire Pigs Purpose: The purpose of this study is to compare the visual and microscopic effects of two different formulations of ketamine—commercially available Ketamine HCl and BB106—after a single subcutaneous (SC) infusion to pig dermal tissue.

Description: Currently available Ketamine HCl is known to cause local tissue site irritation when injected subcutaneously. Symptoms can include erythema, itching, swelling, pain and can even result in a sterile abscess. This is believed to be due to the acidic pH (~4), high osmolarity, the presence of ketamine itself, or a combination of these factors. BB106 is designed, in part, to reduce injection site adverse reactions.

Yorkshire pigs have a very similar dermal tissue morphology to human skin. This species is often used in animal studies to be predictive of human skin.

Animals: The study population will be Yorkshire pig, weighing approximately 30-40 kg. The animal(s) will not be fasted prior to testing.

The formulations used in this study are provided in Table 4.

TABLE 4

Formulations

| Product | Supply or Prepare as | Specifications |
|---|---|---|
| BB106 Ketamine Formulation | Ambient, 70 mg/mL solution with 10% Captisol & benzethonium chloride preservative | pH 5.5 ± 0.5<br>Ketamine concentration: 70 mg/mL<br>Captisol ® (cyclodextrin) concentration: 10%<br>Benzethonium Chloride concentration: 0.1 mg/mL<br>Store at 20° to 25° C. (Controlled Room Temperature) |
| USP Ketamine HCl 100 mg/mL | Ambient, 100 mg/ml, with benzethonium chloride preservative | Ketamine concentration: 100 mg/mL<br>Benzethonium chloride concentration: 0.1 mg/mL<br>Store at 20° to 25° C. (Controlled Room Temperature) |
| USP Ketamine HCl 70 mg/mL | Ambient, 70 mg/ml with benzethonium chloride preservative. Preparation of this sample will be by CRO as per protocol below. | Ketamine concentration: 70 mg/mL<br>Benzethonium chloride concentration: 0.1 mg/mL<br>Store at 20° to 25° C. (Controlled Room Temperature) |

Test Devices: Test ketamine formulations will be delivered using an infusion device (e.g. Valeritas V-Go® 40 pumps). The infusion device delivers at a basal infusion rate of 0.01667 mL/hour. The infusion devices will be filled with test article, per the instructions provided by the manufacturer, by laboratory personnel on the day of dosing prior to administration. The dose schedules used in this study are provided in Table 5.

TABLE 5

Dose Schedules:

| Formulation | Dosing Duration (hrs) | Total Ketamine Dose (mg) |
|---|---|---|
| BB 106 | 72 | 84 |
| USP Ketamine 70 mg/mL | 72 | 84 |
| USP Ketamine 100 mg/mL | 72 | 140 |
| BB 106 | 120 | 140 |
| USP Ketamine 70 mg/mL | 120 | 140 |
| USP Ketamine 100 mg/mL | 120 | 200 |

Protocol:

Six pigs will be dosed in 2 different locations with two different ketamine preparations each. Four doses will be with 70 mg/mL USP Ketamine, two each at 72 and 120-hour dosing durations, four doses with 100 mg/mL USP Ketamine, two each at 72 and 120-hour dosing durations, and four doses with BB106, also two each for 72 and 168 hours. Three pumps will run at a basal rate of 0.01667 ml/hr for 72 hours. After 72 hours the needle will be retracted with the automated button present on the pumps to terminate infusion. The pumps will then be removed, a visual inspection performed and a biopsy of the dermal tissue performed at each injection site. After 48 more hours, or 120 hours after start of dosing, an excision biopsy of the dermal tissue will be performed for each infusion site. At the same start time, three pumps will dispense at a basal rate of 0.01667 ml/hr for 120 hours. At 120-hours post infusion the needles on these devices will be retracted, the pumps will be removed, a visual inspection performed and a biopsy of the dermal tissue will be performed for each infusion site. Site personnel will ensure appropriate spatial separation from other injection/biopsy sites.

The basal flow rate of the infusion pump is 0.01667 mL/hr. This flow rate will be maintained, with no manipulation required by site personnel, for the duration of all treatments, except for daily refills of the device reservoir. Site personnel will make no bolus injections.

The infusion device will be filled with 0.7 mL of test article. This will almost completely fill the device reservoir, which is 0.76 mL. The devices will be refilled daily to ensure continuous dosing. The device will be adhered to the pig on the upper flank by removing the adhesive backing cover, according to treatment location assignments, ensuring spatial separation from other injection/biopsy sites.

At the end of the dosing periods, and after removal of the device, site personnel will make a visual assessment of the injection site and record their observations. Observations should focus on the injection site and adjacent skin tissue. Visual inspections will include, but not be limited to: assessments of any swelling or erythema, with qualitative descriptors like mild/moderate/severe; and measure length and width of any tissue impact from injection site (mm). A digital photograph will be taken at each visual observation.

When the devices are removed at 72 and 120 hours after the start of dosing, site personnel will collect a 2.5 cm×2.5 cm square biopsy, following the removal of the infusion device and visual inspection. The depth of the excision should be down to the first layer of muscle tissue, approximately 1.5-2.0 cm. Biopsies will include the actual needle insertion injection site.

After collection, biopsy samples are prepared according to the following protocol: Place specimens into 10% neutral buffered formalin and prevent from freezing (ensure proper insulation during transport if these are being shipped in an area of the country where that may be a concern). Skin specimens can be placed on a piece of cardboard and let sit for a few minutes before submersion fixing them in formalin (they will stick to the cardboard and it will help preserve their spatial orientation). Site personnel should ensure they are completely submersed in formalin (either the piece of cardboard is completed submerged, or put a piece of gauze or paper towel on top of the specimen to help ensure submersion. Ensure that there is at least a 10:1 ratio of tissue volume to formalin volume. If taking multiple biopsy sites, it is recommended to use a separate container for each biopsy (i.e. a typical biopsy container with formalin) and ensuring that they are each clearly labeled.

Pathology: Following sample preparation, the following assessments will be made and findings will be recorded: spongiosis; superficial and/or deep perivascular inflammation; perifollicular or (more generally including follicles and sweat glands) periadnexal inflammation; type of inflammatory cells in infiltrate, e.g. neutrophils, eosinophils, lymphocytes, histiocytes, plasma cells; dermal edema; interface change; vasculitis, panniculitis, necrosis of epidermis, adnexal structures, or fat; additional findings may be recorded and/or graded at the discretion of the pathologist. Standard ordinal grading (0-4) will be used, where 0=not present and 4=marked.

Hypothesis: It is expected that BB106 formulation will show reduced incidence and/or severity of signs of injection site injury compared to Ketamine HCl formulations. Particularly, reduced incidence or severity of necrosis and/or edema of the epidermis, infiltration of eosinophil and/or perivascular cells into the dermis, inflammation, necrosis, and/or hemorrhage of the subcutis, and/or necrosis or inflammation of the skeletal muscle near the injection site compared to Ketamine HCl formulations is expected.

Example 12. Proposed Dosing Conditions for Administration of Subcutaneous Ketamine Formulations The subcutaneous ketamine formulations provided herein can be used at a variety of dose strengths for treatment of a variety of indications. Below are non-limiting examples of potential dosing schedules for different strengths of ketamine formulations provided herein for specified indications/uses.

Ketamine formulations described in the dosing schedules below are dosed with an infusion device which can deliver the formulation at the indicated flow rates and also deliver the specified bolus amounts as necessary. For each dosage schedule, the number of bolus additions of ketamine formulation which may delivered per hour to the patient is indicated by the "bolus options/hr" field, generally 2-3 bolus options every hour. The "initial bolus" refers to the amount of ketamine formulation delivered at the start of the dosing schedule. Each dosage schedule includes both a "low" and "high" dose option, which may be selected by a medical professional or otherwise modified. Additionally, the dosing schedules provided below are intended to be delivered and followed over the indicated period of time, generally from 4 to 24 hours.

The indications specified in the dosing schedules below are merely suggestive and the dosing schedules are not limited to those indications. "Post Operative Pain Dosing Profile" refers to administration of ketamine following a medical procedure (e.g. a surgical procedure) in order to alleviate the pain during a short to medium term of recovery, but other indications may follow the same or similar dosing profiles. The "Battlefield Pain Dosing Profile" refers to administration of ketamine following a traumatic injury (e.g. a battlefield wound) in order to alleviate pain in the subject over a relatively short period of time, but the dosing schedules provided below may also be used for other indications.

The formulations BB105, BB106, and BB107 refer to the formulations described above in Example 10. The concentrations of ketamine and Captisol® in each formulation and the pH of the formulation is provided below in Table 6. All formulations additionally have 0.1% benzethonium chloride as a preservative.

TABLE 6

| Formulation | BB105 | BB106 | BB107 |
|---|---|---|---|
| Ketamine Stereoisomer | racemic | racemic | S-ketamine |
| Ketamine concentration (mg/mL) | 96 | 70 | 70 |
| Captisol concentration (mg/mL) | 140 | 100 | 100 |
| pH | ~5.5 | ~5.5 | ~5.5 |

Table 7 below provides an exemplary Post Operative Pain Dosing profile using BB106 subcutaneous ketamine formulation over a 24 hour period at both a low and high dose strength.

TABLE 7

| | BB106 Dosing Schedule for Post Operative Pain (24 hours) | | | | | |
|---|---|---|---|---|---|---|
| | Low dose | | | High Dose | | |
| | Solution Delivery | Ketamine Delivery | Captisol Delivery | Solution Delivery | Ketamine Delivery | Captisol Delivery |
| initial bolus | 0.057 mL | 4.0 mg | 5.7 mg | 0.114 mL | 8.0 mg | 11.4 mg |
| basal rate | 0.021 mL/hr | 1.5 mg/hr | 2.1 mg/hr | 0.043 mL/hr | 3.0 mg/hr | 4.3 mg/hr |
| bolus | 0.014 mL | 1.0 mg | 1.4 mg | 0.029 mL | 2.0 mg | 2.9 mg |
| Min total/24 hr | 0.571 mL | 40.0 mg | 57.1 mg | 1.143 mL | 80.0 mg | 114.3 mg |
| Max total/24 hr | 1.257 mL | 88.0 mg | 125.7 mg | 2.514 mL | 176.0 mg | 241.4 mg |
| Bolus options/hr | | 2 | | | 2 | |
| Reservoir Range (mL) | | 1.26 mL | | | 2.51 mL | |

Table 8 below provides an exemplary Post Operative Pain Dosing profile using BB106 subcutaneous ketamine formulation over an 18 hour period at both a low and high dose strength.

TABLE 8

| | BB106 Dosing Schedule for Post Operative Pain (18 hours) | | | | | |
|---|---|---|---|---|---|---|
| | Low dose | | | High Dose | | |
| | Solution Delivery | Ketamine Delivery | Captisol Delivery | Solution Delivery | Ketamine Delivery | Captisol Delivery |
| initial bolus | 0.057 mL | 4.0 mg | 5.7 mg | 0.114 mL | 8.0 mg | 11.4 mg |
| basal rate | 0.021 mL/hr | 1.5 mg/hr | 2.1 mg/hr | 0.043 mL/hr | 3.0 mg/hr | 4.3 mg/hr |
| bolus | 0.014 mL | 1.0 mg | 1.4 mg | 0.029 mL | 2.0 mg | 2.9 mg |
| Min total/18 hr | 0.443 mL | 31.0 mg | 44.3 mg | 0.886 mL | 62.0 mg | 88.6 mg |
| Max total/18 hr | 0.957 mL | 67.0 mg | 95.7 mg | 1.914 mL | 134.0 mg | 191.4 mg |
| Bolus options/hr | | 2 | | | 2 | |
| Reservoir Range (mL) | | 0.96 mL | | | 1.91 mL | |

Table 9 below provides an exemplary Post Operative Pain Dosing profile using BB105 subcutaneous ketamine formulation over a 24 hour period at both a low and high dose strength.

TABLE 9

| | BB105 Dosing Schedule for Post Operative Pain (24 hours) | | | | | |
|---|---|---|---|---|---|---|
| | Low dose | | | High Dose | | |
| | Solution Delivery | Ketamine Delivery | Captisol Delivery | Solution Delivery | Ketamine Delivery | Captisol Delivery |
| initial bolus | 0.042 mL | 4.0 mg | 5.8 mg | 0.083 mL | 8.0 mg | 11.7 mg |
| basal rate | 0.016 mL/hr | 1.5 mg/hr | 2.2 mg/hr | 0.031 mL/hr | 3.0 mg/hr | 4.4 mg/hr |
| bolus | 0.010 mL | 1.0 mg | 1.5 mg | 0.021 mL | 2.0 mg | 2.9 mg |
| Min total/24 hr | 0.417 mL | 40.0 mg | 58.3 mg | 0.883 mL | 80.0 mg | 116.7 mg |
| Max total/24 hr | 0.917 mL | 88.0 mg | 128.3 mg | 1.833 mL | 176.0 mg | 256.7 mg |
| Bolus options/hr | | 2 | | | 2 | |
| Reservoir Range (mL) | | 0.92 mL | | | 1.83 mL | |

Table 10 below provides an exemplary Post Operative Pain Dosing profile using BB105 subcutaneous ketamine formulation over an 18 hour period at both a low and high dose strength.

TABLE 10

| | BB105 Dosing Schedule for Post Operative Pain (18 hours) | | | | | |
|---|---|---|---|---|---|---|
| | Low dose | | | High Dose | | |
| | Solution Delivery | Ketamine Delivery | Captisol Delivery | Solution Delivery | Ketamine Delivery | Captisol Delivery |
| initial bolus | 0.042 mL | 4.0 mg | 5.8 mg | 0.083 mL | 8.0 mg | 11.7 mg |
| basal rate | 0.016 mL/hr | 1.5 mg/hr | 2.2 mg/hr | 0.031 mL/hr | 3.0 mg/hr | 4.4 mg/hr |
| bolus | 0.010 mL | 1.0 mg | 1.5 mg | 0.021 mL | 2.0 mg | 2.9 mg |
| Min total/18 hr | 0.323 mL | 31.0 mg | 45.2 mg | 0.646 mL | 62.0 mg | 990.4 mg |
| Max total/18 hr | 0.698 mL | 67.0 mg | 97.7 mg | 1.396 mL | 134.0 mg | 195.4 mg |

TABLE 10-continued

BB105 Dosing Schedule for Post Operative Pain (18 hours)

|  | Low dose | | | High Dose | | |
|---|---|---|---|---|---|---|
|  | Solution Delivery | Ketamine Delivery | Captisol Delivery | Solution Delivery | Ketamine Delivery | Captisol Delivery |
| Bolus options/hr |  | 2 |  |  | 2 |  |
| Reservoir Range (mL) |  | 0.70 mL |  |  | 1.40 mL |  |

Table 11 below provides an exemplary Battlefield Pain Dosing profile using BB106 subcutaneous ketamine formulation over a 4 hour period at both a low and high dose strength.

TABLE 11

BB106 Dosing Schedule for Battlefield Pain (4 hours)

|  | Low dose | | | High Dose | | |
|---|---|---|---|---|---|---|
|  | Solution Delivery | Ketamine Delivery | Captisol Delivery | Solution Delivery | Ketamine Delivery | Captisol Delivery |
| initial bolus | 0.229 mL | 16.0 mg | 22.9 mg | 0.457 mL | 32.0 mg | 45.7 mg |
| basal rate | 0.114 mL/hr | 8.0 mg/hr | 11.4 mg/hr | 0.229 mL/hr | 16.0 mg | 22.9 mg/her |
| bolus | 0.057 mL | 4.0 mg | 5.7 mg | 0.114 mL | 8.0 mg | 11.4 mg |
| Min total/4 hr | 0.686 mL | 48.0 mg | 68.6 mg | 1.371 mL | 96.0 mg | 137.1 mg |
| Max total/4 hr | 1.143 mL | 80.0 mg | 113.4 mg | 2.286 mL | 160.0 mg | 228.6 mg |
| Bolus options/hr |  | 2 |  |  | 2 |  |
| Reservoir Range (mL) |  | 1.14 mL |  |  | 2.29 mL |  |

Table 12 below provides an exemplary Battlefield Pain Dosing profile using BB106 subcutaneous ketamine formulation over an 8 hour period at both a low and high dose strength.

TABLE 12

BB106 Dosing Schedule for Battlefield Pain (8 hours)

|  | Low dose | | | High Dose | | |
|---|---|---|---|---|---|---|
|  | Solution Delivery | Ketamine Delivery | Captisol Delivery | Solution Delivery | Ketamine Delivery | Captisol Delivery |
| initial bolus | 0.229 mL | 16.0 mg | 22.9 mg | 0.457 mL | 32.0 mg | 45.7 mg |
| basal rate | 0.114 mL/hr | 8.0 mg/hr | 11.4 mg/hr | 0.229 mL/hr | 16.0 mg | 22.9 mg/her |
| bolus | 0.057 mL | 4.0 mg | 5.7 mg | 0.114 mL | 8.0 mg | 11.4 mg |
| Min total/8 hr | 1.143 mL | 80.0 mg | 114.3 mg | 2.286 mL | 160.0 mg | 228.6 mg |
| Max total/8 hr | 2.057 mL | 144.0 mg | 205.7 mg | 4.114 mL | 288.0 mg | 411.4 mg |
| Bolus options/hr |  | 2 |  |  | 2 |  |
| Reservoir Range (mL) |  | 2.06 mL |  |  | 4.11 mL |  |

Table 13 below provides an exemplary Battlefield Pain Dosing profile using BB107 subcutaneous ketamine formulation over a 4 hour period at both a low and high dose strength.

TABLE 13

BB107 Dosing Schedule for Battlefield Pain (4 hours)

| | Low dose | | | High Dose | | |
|---|---|---|---|---|---|---|
| | Solution Delivery | Ketamine Delivery | Captisol Delivery | Solution Delivery | Ketamine Delivery | Captisol Delivery |
| initial bolus | 0.214 mL | 15.0 mg | 21.4 mg | 0.429 mL | 30.0 mg | 42.9 mg |
| basal rate | 0.143 mL/hr | 10.0 mg/hr | 14.3 mg/hr | 0.286 mL/hr | 20.0 mg/hr | 28.6 mg/hr |
| bolus | 0.043 mL | 3.0 mg | 4.3 mg | 0.086 mL | 6.0 mg | 8.6 mg |
| Min total/4 hr | 0.786 mL | 55.0 mg | 78.6 mg | 1.571 mL | 110.0 mg | 157.1 mg |
| Max total/4 hr | 1.300 mL | 91.0 mg | 130.0 mg | 2.60 mL | 182.0 mg | 260.0 mg |
| Bolus options/hr | | 3 | | | 3 | |
| Reservoir Range (mL) | | 1.30 mL | | | 2.60 mL | |

Table 14 below provides an exemplary Battlefield Pain Dosing profile using BB107 subcutaneous ketamine formulation over an 8 hour period at both a low and high dose strength.

TABLE 14

BB107 Dosing Schedule for Battlefield Pain (8 hours)

| | Low dose | | | High Dose | | |
|---|---|---|---|---|---|---|
| | Solution Delivery | Ketamine Delivery | Captisol Delivery | Solution Delivery | Ketamine Delivery | Captisol Delivery |
| initial bolus | 0.214 mL | 15.0 mg | 21.4 mg | 0.429 mL | 30.0 mg | 42.9 mg |
| basal rate | 0.143 mL/hr | 10.0 mg/hr | 14.3 mg/hr | 0.286 mL/hr | 20.0 mg/hr | 28.6 mg/hr |
| bolus | 0.043 mL | 3.0 mg | 4.3 mg | 0.086 mL | 6.0 mg | 8.6 mg |
| Min total/8 hr | 1.357 mL | 95.0 mg | 135.7 mg | 2.714 mL | 190.0 mg | 271.4 mg |
| Max total/8 hr | 2.386 mL | 167.0 mg | 238.6 mg | 4.771 mL | 334.0 mg | 477.1 mg |
| Bolus options/hr | | 3 | | | 3 | |
| Reservoir Range (mL) | | 2.39 mL | | | 4.77 mL | |

Table 15 below provides an exemplary Battlefield Pain Dosing profile using BB107 subcutaneous ketamine formulation over a 24 hour period at both a low and high dose strength.

TABLE 15

BB107 Dosing Schedule for Battlefield Pain (24 hours)

| | Low dose | | | High Dose | | |
|---|---|---|---|---|---|---|
| | Solution Delivery | Ketamine Delivery | Captisol Delivery | Solution Delivery | Ketamine Delivery | Captisol Delivery |
| initial bolus | 0.114 mL | 8.0 mg | 11.4 mg | 0.229 mL | 16.0 mg | 22.9 mg |
| basal rate | 0.036 mL/hr | 2.5 mg/hr | 3.6 mg/hr | 0.071 mL/hr | 5.0 mg/hr | 7.1 mg/hr |
| bolus | 0.029 mL | 2.0 mg | 2.9 mg | 0.071 mL | 5.0 mg | 7.1 mg |
| Min total/24 hr | 0.971 mL | 68.0 mg | 97.1 mg | 1.943 mL | 136.0 mg | 194.3 mg |
| Max total/24 hr | 3.029 mL | 212.0 mg | 302.9 mg | 7.086 mL | 496.0 mg | 708.6 mg |
| Bolus options/hr | | 3 | | | 3 | |
| Reservoir Range (mL) | | 3.03 mL | | | 7.09 mL | |

Table 16 below provides an exemplary Battlefield Pain Dosing profile using BB107 subcutaneous ketamine formulation over an 18 hour period at both a low and high dose strength.

TABLE 16

| | BB107 Dosing Schedule for Battlefield Pain (18 hours) | | | | | |
|---|---|---|---|---|---|---|
| | Low dose | | | High Dose | | |
| | Solution Delivery | Ketamine Delivery | Captisol Delivery | Solution Delivery | Ketamine Delivery | Captisol Delivery |
| initial bolus | 0.114 mL | 8.0 mg | 11.4 mg | 0.229 mL | 16.0 mg | 22.9 mg |
| basal rate | 0.036 mL/hr | 2.5 mg/hr | 3.6 mg/hr | 0.071 mL/hr | 5.0 mg/hr | 7.1 mg/hr |
| bolus | 0.029 mL | 2.0 mg | 2.9 mg | 0.071 mL | 5.0 mg | 7.1 mg |
| Min total/18 hr | 0.757 mL | 53.0 mg | 75.7 mg | 1.514 mL | 106.0 mg | 151.4 mg |
| Max total/18 hr | 2.30 mL | 161.0 mg | 230.0 mg | 5.371 mL | 376.0 mg | 376.0 mg |
| Bolus options/hr | | 3 | | | 3 | |
| Reservoir Range (mL) | | 2.3 mL | | | 5.37 mL | |

Although the disclosure has been described with reference to the above examples, it will be understood that modifications and variations are encompassed within the spirit and scope of the disclosure. Accordingly, the disclosure is limited only by the following claims.

What is claimed is:

1. A pharmaceutical composition, comprising:
    (i) a compound of structural Formula (I):

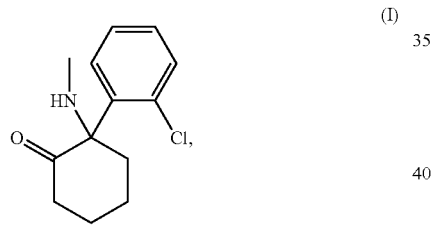

or an enantiomer, a mixture of enantiomers, or an isotopic variant thereof; or a pharmaceutically acceptable salt, solvate or hydrate thereof; and
    (ii) at least one pharmaceutically acceptable excipient; and
    (iii) a complexing agent comprising a substituted cyclodextrin comprising a plurality of acidic functional groups, wherein at least two of the plurality of acidic functional groups are deprotonated counter-anions for a protonated form of a plurality of the compound of structural Formula (I), wherein the pharmaceutical composition has a reduced osmolality relative to a composition comprising a salt of the complexing agent and a salt of the compound of structural Formula (I).

2. The pharmaceutical composition of claim 1, wherein the cyclodextrin is substituted with 3 to 8 acidic functional groups.

3. The pharmaceutical composition of claim 1, wherein the substituted cyclodextrin is sulfobutyl-ether-beta-cyclodextrin (SBEBCD).

4. The pharmaceutical composition of claim 1, wherein the composition has a ratio of the complexing agent to the compound of Formula (I) that is from about 1:4 to about 1:10.

5. The pharmaceutical composition of claim 1, wherein the pharmaceutical composition has an osmolality of no more than about 600 mOsm/kg.

6. The pharmaceutical composition of claim 1, wherein the pharmaceutical composition has a pH of about 4.5 to about 7.

7. The pharmaceutical composition of claim 1, wherein the compound of Formula (I) or an enantiomer, a mixture of enantiomers, or an isotopic variant thereof; or solvate or hydrate thereof, has a concentration at least about 20 mg/mL.

8. A pharmaceutical composition, comprising:
(i) a compound of structural Formula (I):

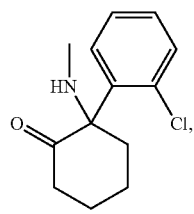

(I)

or an enantiomer, a mixture of enantiomers, or an isotopic variant thereof; or a pharmaceutically acceptable salt, solvate or hydrate thereof;
wherein at least about 75% of the compound of structural Formula (I) is ionized and has a structure of Formula (I-A):

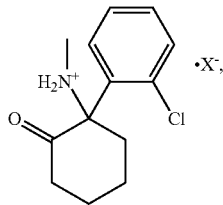

(I-A)

wherein $X^-$ is a substituted cyclodextrin comprising a plurality of acidic functional groups that are deprotonated counter-anions for a plurality of the compound of structural Formula (I-A), wherein the pharmaceutical composition has a reduced osmolality relative to a composition comprising a salt of the complexing agent and a salt of the compound of structural Formula (I).

9. The pharmaceutical composition of claim 8, wherein the substituted cyclodextrin is substituted with 3 to 8 acidic functional groups.

10. The pharmaceutical composition of claim 8, wherein the pharmaceutical composition has a molar ratio of the substituted cyclodextrin to the compound of structural Formula (I) that is from about 1:4 to about 1:10.

11. The pharmaceutical composition of claim 8, wherein the substituted cyclodextrin is SBEBCD.

12. The pharmaceutical composition of claim 8, wherein the substituted cyclodextrin is present in an amount of about 50 mg/mL to about 600 mg/mL.

13. The pharmaceutical composition of claim 8, wherein the pharmaceutical composition has an osmolality of no more than about 600 mOsm/kg.

14. The pharmaceutical composition of claim 8, wherein the pharmaceutical composition has a pH of about 4.5 to about 7.

15. The pharmaceutical composition of claim 8, wherein the compound of Formula (I) or an enantiomer, a mixture of enantiomers, or an isotopic variant thereof; or solvate or hydrate thereof, has a concentration at least about 20 mg/mL.

16. The pharmaceutical composition of claim 8, wherein the pharmaceutical composition further comprises a preservative.

17. A method of treating a disease or disorder, comprising administering to a subject in need thereof a therapeutically effective amount of a pharmaceutical composition comprising a compound of structural Formula (I):

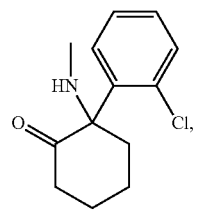

(I)

or an enantiomer, a mixture of enantiomers, or an isotopic variant thereof; or a pharmaceutically acceptable salt, solvate or hydrate thereof; and
a complexing agent comprising a substituted cyclodextrin comprising a plurality of acidic functional groups that are deprotonated counter-anions for a plurality of the compound of structural Formula (I);
wherein the pharmaceutical composition is administered by subcutaneous or intramuscular injection, wherein the pharmaceutical composition has a pH from 4.5 to 7 and a reduced osmolality relative to a composition comprising a salt of the complexing agent and a salt of the compound of structural Formula (I).

18. The pharmaceutical composition of claim 2, wherein the 3 to 8 acidic functional groups comprise carboxylic acids, sulfonic acids, or both.

19. The pharmaceutical composition of claim 9, wherein the 3 to 8 acidic functional groups comprise carboxylic acids, sulfonic acids, or both.

20. The pharmaceutical composition of claim 17, wherein the cyclodextrin is substituted with 3 to 8 acidic functional groups comprising carboxylic acids, sulfonic acids, or both.

* * * * *